US011355236B2

(12) United States Patent
Bodurka et al.

(10) Patent No.: US 11,355,236 B2
(45) Date of Patent: Jun. 7, 2022

(54) PATIENT SUPPORT APPARATUS COMMUNICATION SYSTEMS

(71) Applicant: Stryker Corporation, Kalamazoo, MI (US)

(72) Inventors: Alexander Josef Bodurka, Kalamazoo, MI (US); Krishna Sandeep Bhimavarapu, Kalamazoo, MI (US); Jerald A. Trepanier, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 447 days.

(21) Appl. No.: 16/569,225

(22) Filed: Sep. 12, 2019

(65) Prior Publication Data

US 2020/0082937 A1   Mar. 12, 2020

Related U.S. Application Data

(60) Provisional application No. 62/730,217, filed on Sep. 12, 2018.

(51) Int. Cl.
*H04L 29/06* (2006.01)
*G16H 40/67* (2018.01)
*H04L 9/40* (2022.01)

(52) U.S. Cl.
CPC .......... *G16H 40/67* (2018.01); *H04L 63/061* (2013.01)

(58) Field of Classification Search
CPC .......... H04W 4/50; H04W 4/70; H04W 4/80; H04W 12/08; H04L 63/061; G16H 40/67
See application file for complete search history.

(56) References Cited

U.S. PATENT DOCUMENTS

| 3,191,196 A | 6/1965 | Holm |
| 7,472,439 B2 | 1/2009 | Karmer, Jr. et al. |

(Continued)

FOREIGN PATENT DOCUMENTS

| CA | 2122515 A1 | 10/1995 |
| CN | 1152863 A | 6/1997 |

(Continued)

OTHER PUBLICATIONS

Ellisys Bluetooth Expert Notes, Ellisys 2011.
Bluetooth Mesh Security Overview, Bluetooth Technology Website, Nov. 2017.

*Primary Examiner* — Mohammad A Siddiqi
(74) *Attorney, Agent, or Firm* — Warner Norcross + Judd LLP

(57) ABSTRACT

A patient support apparatus includes a frame, patient support surface, memory having a first key stored therein, a transceiver, and a controller. The transceiver wirelessly communicates with a medical device over a first mesh network using the first key. The controller transmits a request message over the first mesh network to the medical device via the transceiver. The request message includes an identifier identifying the patient support apparatus and a request to join a second mesh network different from the first mesh network. The controller receives a second key input over the first mesh network, uses the second key input to generate a second key, and to use the second key to communicate over the second mesh network. In some instances, the second key input originates from a cloud-based server storing a list of authorized devices for a particular healthcare facility.

17 Claims, 19 Drawing Sheets

(56) References Cited

U.S. PATENT DOCUMENTS

| | | |
|---|---|---|
| 8,284,047 B2 | 10/2012 | Collins, Jr. et al. |
| 8,776,246 B2 | 7/2014 | Allegri et al. |
| 8,856,982 B1 | 10/2014 | Kalivas |
| 8,868,768 B2 * | 10/2014 | Sokoryansky .......... H04L 63/10 709/229 |
| 8,910,329 B2 | 12/2014 | Turner et al. |
| 8,959,681 B2 | 2/2015 | Richards |
| 9,463,126 B2 | 10/2016 | Zerhusen et al. |
| 9,760,681 B2 * | 9/2017 | Douglass ............ G06F 21/6245 |
| 9,937,090 B2 * | 4/2018 | Hayes .................... A61G 7/018 |
| 10,403,401 B2 | 9/2019 | Bronsan |
| 10,898,398 B2 * | 1/2021 | Hayes .................... A61G 7/018 |
| 2011/0087113 A1 | 4/2011 | Mack et al. |
| 2011/0263950 A1 | 10/2011 | Larson et al. |
| 2012/0104818 A1 | 5/2012 | Morris |
| 2014/0090171 A1 | 4/2014 | Hyde et al. |
| 2014/0310876 A1 | 10/2014 | Roussy et al. |
| 2015/0082542 A1 | 3/2015 | Hayes et al. |
| 2015/0096815 A1 | 4/2015 | Ottenweller et al. |
| 2015/0137988 A1 | 5/2015 | Gravenstein et al. |
| 2015/0216474 A1 | 8/2015 | Riley et al. |
| 2016/0275776 A1 | 9/2016 | Shen et al. |
| 2020/0105406 A1 * | 4/2020 | Orona .................... G16H 40/63 |

FOREIGN PATENT DOCUMENTS

| | | |
|---|---|---|
| EP | 2105117 A2 | 9/2009 |
| EP | 2910226 A1 | 8/2015 |
| GB | 1486991 | 1/1974 |
| JP | 2005507267 A | 3/2005 |
| JP | 2008514301 A | 5/2008 |
| TW | 201019894 A | 6/2010 |
| WO | 9834577 A1 | 8/1998 |
| WO | 0119313 A1 | 3/2001 |
| WO | 2006023447 A2 | 3/2006 |
| WO | 2007075701 A1 | 7/2007 |
| WO | 2011113070 A1 | 9/2011 |
| WO | 2015032003 A1 | 3/2015 |

* cited by examiner

PATIENT SUPPORT APPARATUS COMMUNICATION SYSTEMS

CROSS-REFERENCE TO RELATED APPLICATIONS

This application claims priority to U.S. provisional patent application Ser. No. 62/730,217 filed Sep. 12, 2018, by inventors Alexander Bodurka et al. and entitled PATIENT SUPPORT APPARATUS COMMUNICATION SYSTEMS, the complete disclosure of which is incorporated herein by reference.

BACKGROUND

The present disclosure relates to communication systems for patient support apparatuses—such as cots, stretchers, beds, recliners, operating tables, etc.—and other medical devices that are able to communicate with the patient support apparatuses. More particularly, the present disclosure relates to systems and methods by which medical devices such as patient support apparatuses may securely communicate with each other using one or more networks, such as, but not limited to, mesh networks.

In a healthcare setting, it is often desirable for data from medical devices to be shared, either with each other and/or with one or more servers on a local area network (or in the cloud). In some instances, such data is forwarded from a medical device to a one or more remote locations, such as a nurses' station, where caregivers can review such information without the need to physically travel to each and every room in the healthcare environment (e.g. a hospital, medical center, long term care facility, or the like). Often such information is forwarded to a healthcare computer network, such as an Ethernet, where one or more servers make the information available for display on any one or more computers or mobile devices that are communicatively coupled to the healthcare computer network.

In some instances, the patient support apparatuses forward such information via a direct wireless connection to one or more wireless access points of the healthcare network. Such information may be forwarded via IEEE 802.11 standards. In other situations, such information may be forwarded via a wired connection to the healthcare network. In many instances, the forwarding of such information utilizes the existing Information Technology (IT) infrastructure incorporated into the healthcare facility by the administrators of the healthcare facility.

SUMMARY

The present disclosure provides systems and methods for communicating over one or more networks of medical devices in a manner that is secure, yet not unduly burdensome on individuals to set up and maintain. In many instances, the networks are ad-hoc networks created and maintained utilizing one or more medical devices' existing communication channels with the Internet. In some instances, configuration of only a single initial medical device enables all other authorized devices to join the network without the need for any administrative steps to be taken on the part of technicians associated with the medical devices or other IT personnel associated with the healthcare facility. By utilizing one or more networks, such as, but not limited to, mesh networks, for data communication, communication between the medical devices and one or more of the healthcare facility's IT infrastructure (e.g. a local area network) and/or cloud based servers is facilitated without requiring additional infrastructure and/or administrative tasks. These and other benefits will be apparent to those skilled in the art in light of the detailed disclosure contained herein.

According to one embodiment of the present disclosure, a patient support apparatus is provided that includes a frame, a patient support surface, a memory, a transceiver, and a controller. The patient support surface is supported on the frame and adapted to support a patient thereon. The memory includes a first key stored therein. The transceiver wirelessly communicates with a medical device over a first mesh network using the first key. The controller transmits a request message over the first mesh network to the medical device via the transceiver. The request message includes an identifier identifying the patient support apparatus and a request to join a second mesh network different from the first mesh network. The controller receives a second key input over the first mesh network, uses the second key input to generate a second key, and thereafter uses the second key to communicate over the second mesh network.

According to other aspects of the present disclosure, the controller is further adapted to receive a software update over the second mesh network but not the first mesh network.

In some embodiments, the transceiver is adapted to communicate over the first and second mesh networks using a common communication frequency and a common communication protocol.

The controller is further adapted to encrypt messages transmitted over the first mesh network using the first key and to encrypt messages transmitted over the second mesh network using the second key, in at least some embodiments.

The controller may be further adapted to receive a second request message over the first mesh network from a second medical device. In such cases, the second request message includes a second identifier identifying the second medical device and a request by the second medical device to join the second mesh network. The controller forwards the second identifier and request to a third medical device via the transceiver. This forwarding of the second identifier and request to the third medical device may utilize the second mesh network.

In some embodiments, the controller is further adapted to receive a software update over the second mesh network, wherein the software update is received from a second medical device and intended for updating software on-board a third medical device. The controller then forwards the software update to the third medical device over the second mesh network, either directly thereto or through one or more intermediaries.

The controller may further be adapted to receive a validation message from a second medical device over the second mesh network. The validation message includes data indicating that a third medical device is a valid device for joining the second mesh network and the controller forwards to the third medical device the second key input in response to the validation message. The forwarding may take place directly or through one or more intermediaries.

In some embodiments, the controller is adapted to communicate with a remote server via an Internet connection and to receive a validation message from the remote server via the Internet connection. The validation message includes data indicating that a second medical device is a valid device for joining the second mesh network, and the controller forwards to the second medical device the second key input in response to the validation message. The forwarding may take place directly or through one or more intermediary devices.

In some embodiments, the patient support apparatus further includes a base, a plurality of wheels coupled to the base, an adjustable height litter supported on base, and a plurality of siderails. The adjustable height litter is adapted to support the patient support surface and the plurality of siderails are coupled to the adjustable height litter and adapted to move between raised and lowered positions. The medical device, in some embodiments, is a second patient support apparatus.

According to another aspect of the present disclosure, a patient support apparatus is provided that includes a frame, a patient support surface, a memory, a first transceiver key, and a controller. The patient support surface is supported on the frame and is adapted to support a patient thereon. The memory includes a first key, a second key, and a second key input stored therein. The first transceiver wirelessly communicates with a set of medical devices over a first network using the first key and wirelessly communicates with a subset of the medical devices over a second network using the second key. The controller is adapted to receive a validation message via the first transceiver indicating an individual one of the medical devices in the set of medical devices has been validated for inclusion in the subset of the medical devices. The controller is further adapted to transmit the second key input to the individual one of the medical devices in response to the validation message in order to enable the individual one of the medical devices to generate the second key from the second key input and to use the second key to communicate over the second network.

According to other aspects of this disclosure, the controller receives the validation message over the second network from a medical device in the subset of the medical devices.

In some embodiments, one of the first and second networks is a mesh network and the other of the first and second networks is not a mesh network. In still other embodiments, both of the first and second networks are mesh networks.

The patient support apparatus may include a second transceiver adapted to communicate directly with an access point of a healthcare computer network. In such cases, the controller receives the validation message from a remote server in communication with the access point. The remote server may be located outside of a healthcare facility in which the patient support apparatus and set of medical devices are located.

In some embodiments, the controller is further adapted to receive a software update via the first transceiver and the second network but not via the first network. The software update may be for the patient support apparatus or for another device. In the case of another device, the controller is further adapted to transmit the software update via the first transceiver and the second network to the another device, but not transmit the software update via the first network.

The first network and the second network both use Bluetooth communications, in at least one embodiment, but do not require the patient support apparatus and medical devices to be paired with each other before communicating with each other. The different networks are defined in such embodiments by different encryption keys and/or encryption algorithms.

The controller, in some embodiments, is further adapted to encrypt messages transmitted over the first network using the first key and to encrypt messages transmitted over the second network using the second key.

In some embodiments, the controller is adapted to receive a request message from the individual one of the medical devices prior to receiving the validation message. The request message includes a request for the individual one of the medical devices to be validated for inclusion in the subset of the medical devices. The controller forwards the request message to a validation node of the second network.

According to another embodiment of the present disclosure, a patient support apparatus is provided that includes a frame, a patient support surface, a memory, a first transceiver, and a controller. The patient support surface is supported on the frame and adapted to support a patient thereon. The memory includes a first key stored therein. The first transceiver is adapted to wirelessly communicate with a set of medical devices over a first network using the first key. The controller is adapted to send a request message over the first network. The request message includes a request for a second key input enabling the patient support apparatus to generate a second key for communicating over a second network using the first transceiver. The controller receives a validation message with the second key input if a validation node on the second network approves of the request.

According to other aspects of the present disclosure, the controller is further adapted to use the second key to receive a software update over the second network. The software update may be intended for the patient support apparatus, in which case the controller implements the software update on the patient support apparatus. The software may alternatively be intended for a specific one of the set of medical devices, in which case the controller is adapted to forward the software update to the specific one of the medical devices over the second network.

In some embodiments, the patient support apparatus further comprises a second transceiver adapted to communicate directly with a hospital computer network having a plurality of nodes and access points. In such cases, the second network does not include any of the nodes or access points of the hospital computer network, and the software update is able to be delivered from the patient support apparatus to the specific one of the medical devices without using the hospital computer network.

The validation node is in communication with a remote server via the Internet, in at least some embodiments.

According to another embodiment of the present disclosure, a patient support apparatus system is provided that includes a plurality of patient support apparatuses. Each of the patient support apparatuses comprises a frame, a patient support surface, a transceiver, and a controller. The patient support surfaces are supported on their respective frame and adapted to support patients thereon. The transceivers are adapted to communicate over a first network using a first key that is factory-installed on each of the plurality of patient support apparatuses. The transceivers are further adapted to communicate over a second network after receiving a second key input. The controllers are adapted to use the second key inputs to generate second keys that enable the transceivers to communicate over the second network.

According to other aspects of the present disclosure, the controllers are adapted to use a factory-installed algorithm to generate the second key from the second key input.

In some embodiments, the plurality of patient support apparatuses are adapted to automatically join the first network without requiring a technician to input any data into the patient support apparatuses.

The patient support apparatuses may further be adapted to receive the second key input from a technician and, once a first one of the plurality of patient support apparatuses receives the second key input from the technician, the first one of the plurality of patient support apparatuses is adapted to distribute the second key input to the rest of the plurality of patient support apparatuses without requiring the technician to perform any additional steps.

The first network, in some embodiments, includes a plurality of non-patient support apparatus medical devices. Each of the non-patient support apparatus medical devices includes the first key factory-installed therein, and each of the non-patient support apparatus medical devices are adapted to receive the second key input and use the second key input to generate the second key. This enables the non-patient support apparatus medical devices to join the second network.

Each of the patient support apparatuses may also be adapted to receive a software update intended for another one of the plurality of patient support apparatuses and to forward the software update to the intended another one of the plurality of patient support apparatuses using the second network. Alternatively, or additionally, each of the plurality of patient support apparatuses may be adapted to receive a software update intended for one of the non-patient support apparatus medical devices and to forward the software update to the intended one of the non-patient support apparatus medical devices using the second network.

According to another embodiment of the present disclosure, a patient support apparatus system for a healthcare facility is provided that includes a plurality of patient support apparatuses. Each of the patient support apparatuses includes a frame, a patient support surface supported on the frame and adapted to support a patient thereon, a transceiver, and a controller. The transceivers are adapted to communicate over a first mesh network using a first key that is factory-installed on each of the plurality of patient support apparatuses. The transceivers are further adapted to communicate over a second mesh network after receiving a second key input. The controllers are adapted to use the second key input to generate a second key that enables the transceivers to communicate over the second mesh network. A first one of the patient support apparatuses is adapted to receive the second key input from a technician and to distribute the second key input to the rest of the plurality of patient support apparatuses over the first mesh network without requiring the technician to perform any additional steps.

According to other aspects, the first key is not unique to the healthcare facility and the second key is unique to the healthcare facility.

The patient support apparatuses are adapted, in at least one embodiment, to receive a software update intended for another one of the plurality of patient support apparatuses and to forward the software update to the intended another one of the plurality of patient support apparatuses using the second mesh network. Alternatively, or additionally, the patient support apparatuses are adapted to receive a software update intended for a non-patient support apparatus medical device and to forward the software update to the intended the non-patient support apparatus medical device using the second mesh network.

In some embodiments, the first mesh network and the second mesh network both use Bluetooth communications but do not require the patient support apparatuses to be paired with each other before communicating with each other.

The controller of each patient support apparatus, in some embodiments, uses a factory-installed algorithm to generate the second key from the second key input.

In some embodiments, a first one of the patient support apparatuses further comprises a second transceiver adapted to communicate directly with a hospital computer network having a plurality of nodes and access points. In such embodiments, the first mesh network does not include any of the nodes or access points of the hospital computer network, thereby allowing the first one of the patient support apparatuses to distribute the second key input to the rest of the plurality of patient support apparatuses over the first mesh network without using the hospital computer network.

In any of the embodiments, the patient support apparatus(es) can be beds, stretchers, recliners, cots, combinations thereof, or any other type of support structures used in a healthcare setting for providing support to a patient.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
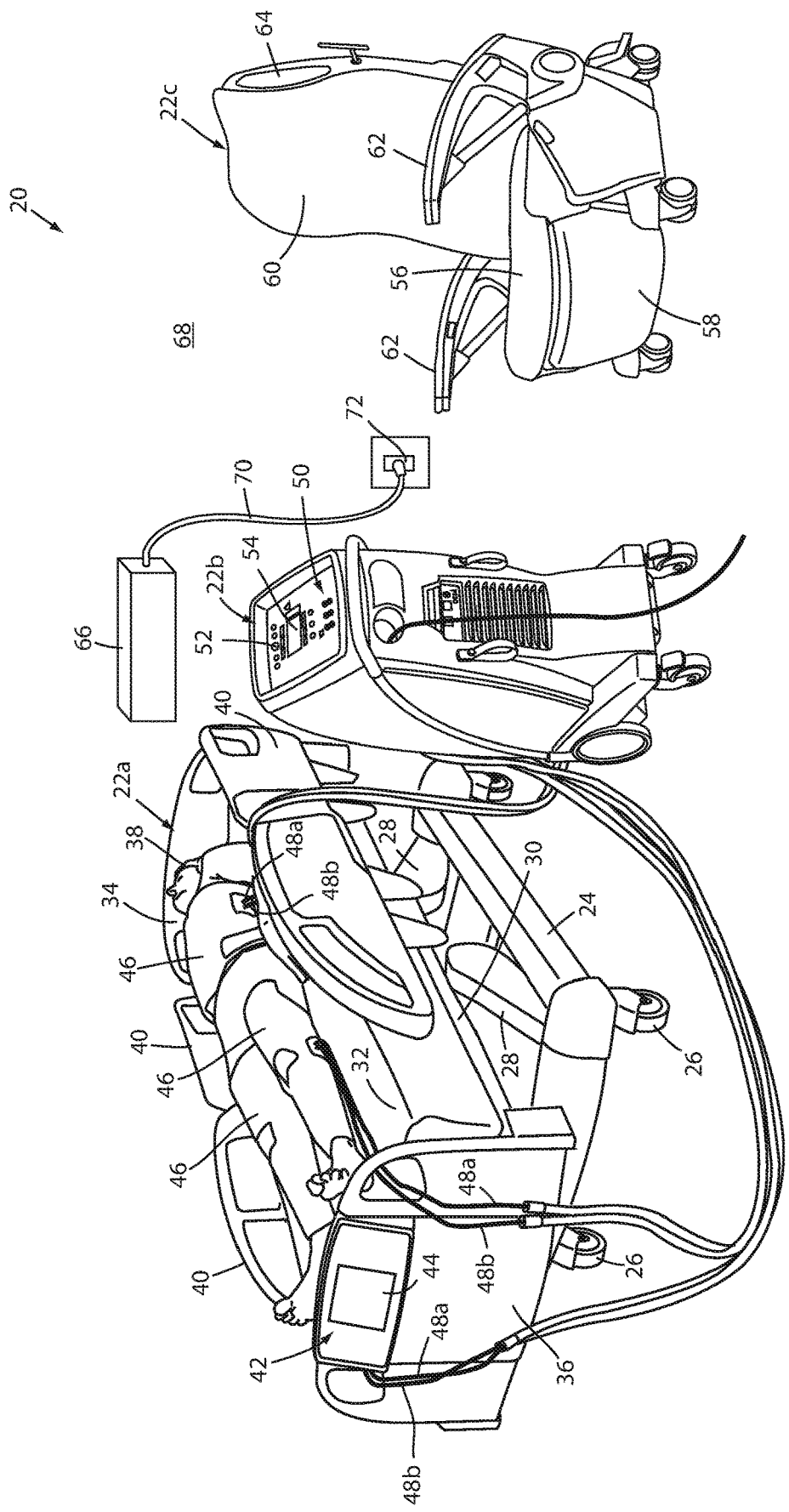
FIG. 1 is a plan view diagram of a communication system of the present disclosure showing a plurality of medical devices adapted to communicate with each other over a plurality of mesh networks.

An illustrative example of a medical device communication system 20 according to one embodiment of the present disclosure is shown in FIG. 1. In the particular configuration shown in FIG. 1, which may vary widely, communication system 20 includes a plurality of medical devices 22, such as a patient support apparatus 22a, a thermal control unit 22b, and a recliner 22c that are in wireless communication with each other. More specifically, patient support apparatus 22a, thermal control unit 22b, and recliner 22c are in communication with each other via one or more networks, as will be discussed in greater detail below. It will be understood that communication system 20 can be incorporated into more than the three particular devices (22a-c) shown in FIG. 1, and/or that communication system 20 can be incorporated into other medical devices 22 besides the three specific ones shown in FIG. 1. Thus, the network(s) of communication system 20 may vary widely in both their size and content from the one illustrated in FIG. 1, which is presented herein merely as an illustrative example suitable for explaining the principles of the present disclosure.

Still further, the topology of the network(s) of communication system 20 can vary widely. In many embodiments, at least two networks are included and one or both of them are mesh networks. Indeed, the majority of the following written description describes embodiments of communication system 20 that utilize one or more nesh networks, but it will be understood that other types of network topologies may be used. These other types of network topologies include, but are not limited to, star, ring, daisy, extended star, tree, and hybrid topologies that combine together one or more of the aforementioned topologies. It will also be understood that the term "mesh network" as used herein includes both fully connected mesh networks in which all nodes are able to communicate directly with all other nodes, as well as partially connected mesh networks in which some nodes are only able to communicate with other nodes via one or more intermediary nodes and/or some nodes are temporarily unable to communicate with other nodes. Still further, the transmission media used to connect the nodes together in the mesh or other types of networks may vary from embodiment to embodiment, and includes both wired and wireless media, as well as multiple different types of protocols used in conjunction with the transmission media.

Patient support apparatus 22a is shown in FIG. 1 as a bed, but it may alternatively be a cot, a stretcher, an operating table, or any other type of structure used to support a patient in a healthcare setting. In general, patient support apparatus 22a include a base 24 having a plurality of wheels 26, a pair of lifts 28 supported on said base, a litter frame 30 supported on said lifts, and a patient support surface 32 supported on said frame. Patient support apparatus 22a may further include a headboard 34 and a footboard 36.

Base 24 of patient support apparatus 22a may include a brake that is adapted to selectively lock and unlock wheels 26 so that, when unlocked, patient support apparatus 22a may be wheeled to different locations. Lifts 28 are adapted to raise and lower litter frame 30 with respect to base 24. Lifts 28 may be hydraulic actuators, electric actuators, or any other suitable device for raising and lowering frame 30 with respect to base 24. In some embodiments, lifts 28 may be operable independently so that the orientation of litter frame 30 with respect to base 24 may also be adjusted.

Litter frame 30 provides a structure for supporting patient support surface 32, headboard 34, and footboard 36. Patient support surface 32, which may be a mattress or other soft surface, is adapted to provide a surface on which a patient 38 may sit and/or lie. Patient support surface 32 may be supported by a deck section of litter frame 30 that includes a plurality of sections, some of which may be pivotable about generally horizontal pivot axes. In the embodiment shown in FIG. 1, litter frame 30 includes a patient support deck having a pivotable head section, which is also sometimes referred to as a Fowler section, which is pivotable between a generally horizontal orientation (shown in FIG. 1) and a plurality of raised positions (not shown in FIG. 1). Other sections, such as a thigh section and/or a foot section may also be pivotable.

A plurality of siderails 40 may also be coupled to litter frame 30. Such siderails 40 are movable between a raised position in which they block ingress and egress into and out of patient support apparatus 22a, and a lowered position in which they are not an obstacle to such ingress and egress.

A user interface 42 is provided on footboard 36 of patient support apparatus 22a and includes a display 44 (FIG. 1). User interface 42 provides a set of controls for a user to control the operation of patient support apparatus 22a, including, in some embodiments, the joining of patient support apparatus 22a into one or more mesh networks of communication system 20, as will be discussed in greater detail below. In addition to controlling its communication abilities within communication system 20, user interface 42 may include controls for allowing a user to do one or more of the following: change a height of litter frame 30, raise or various sections of the deck supported on litter frame 30, activate and deactivate a brake for wheels 26, arm and disarm an exit detection system, take a weight reading of the patient, activate and deactivate a propulsion system, and communicate with a healthcare facility computer network installed in the healthcare facility in which patient support apparatus 22a is positioned. Still other functions may be controlled via user interface 42. The controls associated with any one or more of these functions may utilize physical controls separate from display 44, or display 44 may be a touchscreen display with one or more of the controls being presented on touchscreen display 44, or a combination of the two.

Patient support apparatus 22a further includes at least one wireless transceiver adapted to allow patient support apparatus 22a to wirelessly communicate with one or more other medical devices 22 of communication system 20, such as, but not limited to, medical devices 22b and 22c of FIG. 1. The wireless transceiver allows data to be exchanged between authorized medical devices 22 via one or more mesh networks established between two or more of the medical devices 22, as well as to send and/or receive data from one or more devices that are not part of the mesh network, but which are in communication with one or more medical devices 22 that are part of the mesh network.

In some embodiments, user interface 42 includes one or more controls that are manually manipulated by a user in order to carry out one or more functions utilizing the wireless transceiver, as will be discussed in greater detail below. In other embodiments, the joining of patient support apparatus 22a to one or more mesh networks happens automatically without any user intervention, and user interface 42 may omit the one or more controls that otherwise would be included for managing such mesh network communication. These concepts are discussed in greater detail below.

The construction of any of base 24, lifts 28, litter frame 30, patient support surface 32, headboard 34, footboard 36, and/or siderails 40 may be the same as disclosed in commonly assigned, U.S. Pat. No. 7,690,059 issued to Lemire et al., and entitled HOSPITAL BED, the complete disclosure of which is incorporated herein by reference; or as disclosed in commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosure of which is also hereby incorporated herein by reference. The construction of any of these components may also take on forms different from what is disclosed in the aforementioned patent and patent publication.

Thermal control unit 22b (FIG. 1) is adapted to provide thermal therapy to a patient 38, such as by changing and/or maintaining a temperature of the patient 38. Thermal control unit 22b is coupled to a plurality of thermal pads 46, which may take on a variety of forms, such as, but not limited to, blankets, vests, patches, caps, or other structure. Thermal control unit 22b is coupled to thermal pads 46 via a plurality of hoses 48. Each thermal pad 46 includes a supply hose 48a and a return hose 48b. Thermal control unit 22b delivers temperature controlled fluid (such as, but not limited to, water) to the thermal pads 46 via the fluid supply hoses 48a. After the temperature controlled fluid has passed through thermal pads 46, thermal control unit 22b receives the temperature controlled fluid back from thermal pads 46 via the return hoses 48b. In some modified embodiments of thermal control unit 22b, one or more auxiliary lines may be coupled between the thermal control unit 22b and one or more of the thermal pads 46. Such auxiliary lines may provide thermal control unit 22b with additional data regarding the patient, the thermal pads 46, and/or other information, or such auxiliary lines may provide a conduit for supplying a different fluid (e.g. a gas) to the thermal pads. Still other purposes may be served by the auxiliary line. Examples of the types of auxiliary lines that may be used with such a modified thermal control unit are disclosed in the following commonly assigned U.S. patent applications: Ser. No. 15/675,061 filed Aug. 11, 2017, by inventors James K. Galer et al., and entitled THERMAL THERAPY DEVICES; Ser. No. 15/820,558 filed Nov. 22, 2017, by inventors Gregory S. Taylor et al. and entitled THERMAL SYSTEM; and Ser. No. 62/610,327 filed Dec. 26, 2017, by inventors Gregory S. Taylor et al. and entitled THERMAL SYSTEM WITH PATIENT SENSOR(S), the complete disclosures of all of which are incorporated herein in their entirety by reference. Still other types of auxiliary lines may be coupled between the thermal control unit 22b and thermal pads 46.

In the embodiment shown in FIG. 1, thermal control unit 22b uses three thermal pads 46 in the treatment of patient 38. A first thermal pad 46 is wrapped around a patient's torso, while second and third thermal pads 46 are wrapped, respectively, around the patient's right and left legs. Other configurations can be used and different numbers of thermal pads 46 may be used with thermal control unit 22b, depending upon the number of inlet and outlet ports that are included with thermal control unit 22b. By controlling the temperature of the fluid delivered to thermal pads 46 via supply hoses 48a, the temperature of the patient 38 can be controlled via the close contact of the pads 46 with the patient 38 and the resultant heat transfer therebetween.

Thermal control unit 22b includes a user interface 50 having a plurality of controls 52 and a display 54. Controls 52 allow a user to operate thermal control unit 22b, including setting a desired fluid target temperature and/or a desired patient target temperature, and/or to control other aspects of thermal control unit 22b. User interface 50 communicates with an internal controller and includes controls 52 enabling a user to turn thermal control unit 22b on and off, as well as one or more controls enabling the user to select a target temperature for the fluid delivered to thermal pads 46. User interface 50 may also include one or more controls 52 for controlling one or more aspects of a wireless transceiver adapted to allow thermal control unit 22b to wirelessly communicate with one or more other medical devices 22 of communication system 20, such as, but not limited to, medical devices 22a and 22c of FIG. 1. The wireless transceiver allows data to be exchanged between authorized medical devices 22 via one or more mesh networks established between two or more of the medical devices 22, as well as to send and/or receive data from one or more devices that are not part of the mesh network, but which are in communication with one or more medical devices 22 that are part of the mesh network. In other embodiments, the joining of thermal control unit 22b to one or more mesh networks happens automatically without any user intervention, and user interface 50 need not include any controls 52 for joining thermal control unit 22b to a mesh network. These concepts are discussed in greater detail below.

Further details about the non-mesh network components of thermal control unit 22b of at least one unit suitable for uses according to the present disclosure may be found in any one or more of the following commonly assigned U.S. patent applications: Ser. No. 62/638,400 filed on Mar. 5, 2018 by inventors Gregory S. Taylor et al. and entitled THERMAL CONTROL SYSTEM WITH STEP RESPONSE; Ser. No. 62/610,362 filed Dec. 26, 2017, by inventor Gregory S. Taylor and entitled THERMAL CONTROL SYSTEM WITH GRAPHICAL USER INTERFACE; Ser. No. 15/616,574 filed Jun. 7, 2017 by inventors Gregory S. Taylor et al. and entitled THERMAL CONTROL SYSTEM; and Ser. No. 14/282,383 filed May 20, 2014, by inventors Christopher Hopper et al. and entitled THERMAL CONTROL SYSTEM, the complete disclosures of all of which are incorporated herein by reference. Still other types of thermal control units may be used with communication system 20.

Recliner 22c (FIG. 1) is adapted to support patient 38 and/or another person thereon. Recliner 22c includes a seat 56, a leg rest 58, a backrest 60, a pair of armrests 62, and a pair of control panels 64. Seat 56, leg rest 58, and backrest 60 may be movable to a variety of different orientations, such as a flat orientation in which all three sections are substantially horizontal, a Trendelenburg position, and/or a stand-assist position. In some embodiments, recliner 22c is constructed in any of the manners, and/or includes any of the same functions as the recliners, disclosed in commonly assigned U.S. Pat. No. 9,713,559 issued Jul. 25, 2017, to inventors Christopher Hough et al. and entitled MEDICAL SUPPORT APPARATUS, the complete disclosure of which is incorporated herein by reference. The movement of seat 56, leg rest 58, and backrest 60, in some embodiments, is coordinated in one or more of the manners disclosed in commonly assigned U.S. Pat. No. 9,782,005 issued Oct. 10, 2017, to inventors Anish Paul et al. and entitled MEDICAL SUPPORT APPARATUS, the complete disclosure of which is incorporated herein by reference. Still other manners of constructing and/or operating recliner 22c may be utilized.

Control panel 64 includes one or more controls for controlling the movement of recliner 22c, as well as one or more controls for controlling other aspects of recliner 22c. In some embodiments, control panel 64 may also include one or more controls for controlling one or more aspects of a wireless transceiver adapted to allow recliner 22c to wirelessly communicate with one or more other medical devices 22 of communication system 20, such as, but not limited to, medical devices 22a and 22b of FIG. 1. The wireless transceiver allows data to be exchanged between authorized medical devices 22 via one or more mesh networks established between two or more of the medical devices 22, as well as to send and/or receive data from one or more devices that are not part of the mesh network, but which are in communication with one or more medical devices 22 that are part of the mesh network. In other embodiments, the joining of recliner 22c to one or more mesh networks happens automatically without any user intervention, and control panel 64 need not include any controls for joining recliner 22c to a mesh network. These concepts are discussed in greater detail below.

In some embodiments, patient support apparatus 22a is adapted to wirelessly communicate with a headwall unit 66 mounted to a headwall 68 of a room in a healthcare facility. Headwall unit 66 allows patient support apparatus 22a to wirelessly communicate with a nurse call system. As will be discussed in greater detail below, patient support apparatus 22a is equipped with a pair of wireless transceivers adapted to communicate with wireless transceivers contained with headwall unit 66. Headwall unit 66 also includes a cable 70 coupled to an outlet 72 of a nurse call system. Outlet 72 is typically coupled to a room interface board 74 (FIG. 2) that, in addition to coupling to the nurse call system, also couples to one or more environmental controls within the room, such as, but not limited to, controls for controlling a room light, a thermostat, a television, curtains, and/or other devices in the room. Headwall unit 66 relays data received from patient support apparatus 22a to the nurse call system, and vice versa. Headwall unit 66 also relays commands and data between patient support apparatus 22a and the room controls coupled to the room interface board 74, thereby allowing a patient on patient support apparatus 22a to control various aspects of the room without having to leave support surface 32.

In some embodiments, headwall unit 66 is constructed to include any of the structures and/or functionality disclosed in any of the following commonly assigned U.S. patent applications: 62/600,000 filed Dec. 18, 2017, by inventor Alexander Bodurka and entitled SMART HOSPITAL HEADWALL SYSTEM; 62/587,867 filed Nov. 11, 2017, by inventors Alexander Bodurka et al. and entitled PATIENT SUPPORT APPARATUSES WITH LOCATION/MOVEMENT DETECTION; 62/598,787 filed Dec. 14, 2017, by inventors Alexander Bodurka et al. and entitled HOSPITAL HEADWALL COMMUNICATION SYSTEM; and Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosures of which are all incorporated herein by reference in their entirety.

Figure 2:
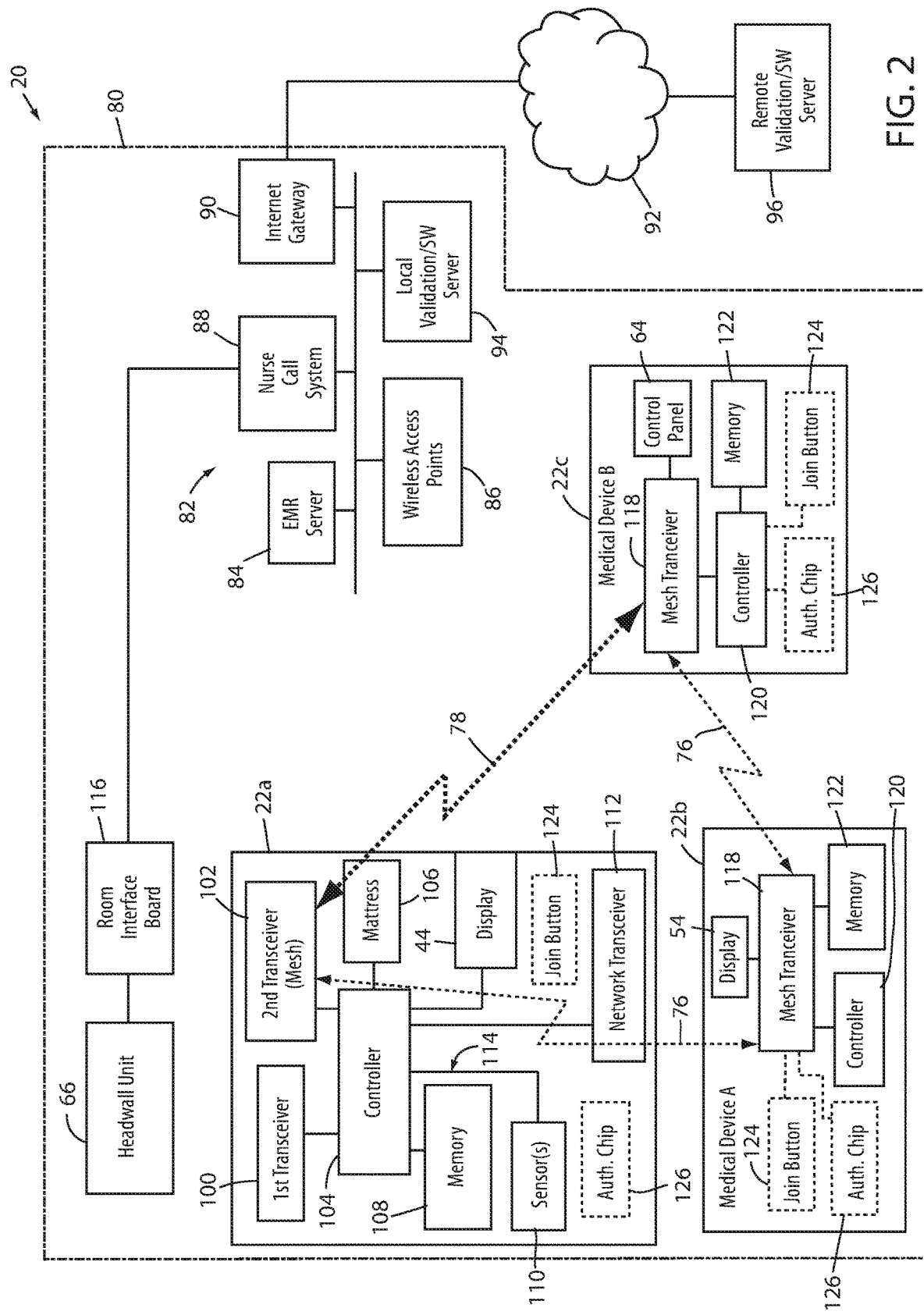
FIG. 2 is a block diagram of the communication system of FIG. 1 showing additional details of the medical devices, as well as illustrating the medical devices in an illustrative healthcare facility having a local area network coupled to the Internet.

FIG. 2 illustrates in greater detail the medical devices 22a-c of FIG. 1 shown communicating with each other over a pair of mesh networks, as well as the potential interaction of at least one of the medical devices with a local area network of the healthcare facility. More specifically, FIG. 2 illustrates patient support apparatus 22a communicating with thermal control unit 22b over a provisioning mesh network 76 and with recliner 22c over a main mesh network 78. Further, FIG. 2 shows thermal control unit 22b communicating with recliner 22c over the provisioning mesh network 76. The function and operation of the mesh networks 76 and 78 will be discussed in greater detail below.

In the example shown in FIG. 2, a portion of a healthcare facility 80 is shown and the healthcare facility 80 includes a conventional local area network 82, which may be an Ethernet or other conventional local area network. The particular structure and applications on the local area network 82 will vary from healthcare facility 80 to healthcare facility 80, but will generally include an Electronic Medical Records (EMR) server 84, a plurality of wireless access points 86 distributed throughout the facility 80, a nurse call system 88, and an Internet gateway 90 that allows applications in communication with the network 82 to communicate with the Internet 92. All of the aforementioned items (84-90) may be conventional items. In addition to these items, a validation and software server is included as part of communication system 20. The validation and software server may be a local validation and software server 94, or it may be a remote validation and software server 96. Still further, in some embodiments of communication system 20, both a local and a remote software and validation server 94 and 96 may be included.

Software and validation servers 94 and 96 perform the same functions. The difference is their location. Local software and validation server 94 is physically located on the premises of the healthcare facility 80 while remote software and validation server 96 is located remote from the healthcare facility 80, but in communication with local area network 82 via the Internet 92. For purposes of the following written description, the functions of the servers 94 and 96 will be described with a focus on local server 94, but it will be understood that this description is equally applicable to remote server 96.

Local software and validation server 94 functions to provide software updates to one or more of the medical devices 22 that are in communication with one or more of the mesh networks 76, 78. Alternatively or additionally, software and validation server 94 functions to validate medical devices 22 for inclusion in main mesh network 78. This latter function ensures that only authorized devices are added to main mesh network 78, thereby providing security against unauthorized usage of, or unauthorized intrusion into, main mesh network 78.

Before describing the functions and operations of mesh networks 76 and 78, the components of medical devices 22a-c will first be described. Patient support apparatus 22a includes a first transceiver 100, a second transceiver 102, a controller 104, a mattress 106, a memory 108, one or more sensors 110, a network transceiver 112, and display 44. Structures 44, 100, 102, 106, 108, 110, and 112 are all in communication with controller 104, which may be comprised of one or more conventional microprocessors, microcontrollers, field programmable gate arrays, systems on a chip, volatile or nonvolatile memory, discrete circuitry, and/or other hardware, software, firmware and/or combinations thereof that are capable of carrying out the functions described herein, as would be known to one of ordinary skill in the art.

Controller 104 communicates with structures 44, 100, 102, 106, 108, 110, and 112 over an internal communications network 114. Internal network 114 may be implemented in different manners. In some embodiments, network 114 is a Controller Area Network (including CANOpen, DeviceNet, and other networks having a CAN physical and data link layer), a LONWorks network, a Local Interconnect Network (LIN), a FireWire network, an I-squared-C network, an RS-485 network, and/or a combination of one or more of these communication structures or any other known communication structures for communicating messages between electronic structures on patient support apparatus 22a. In other embodiments, still other types of communication may be used.

First and second transceivers 100 and 102 of patient support apparatus 22a (FIG. 2) are adapted to wirelessly communicate with headwall unit 66. It will be understood by those skilled in the art that the use of the terms "first transceiver" and "second transceiver" herein has been done for communicative convenience, and that in no way do the "first" and "second" labels connote any significance to, or ranking of, the respective transceivers, nor are they intended to suggest a limit to the number of transceivers that may be present on a given patient support apparatus 22a.

In some embodiments, first transceiver 100 is an infrared transceiver and second transceiver 102 is a Bluetooth transceiver, although it will be understood that other types of transceivers may be used. Further, it will be understood that the communication of first and second transceivers 100 and 102 with headwall unit 66 may utilize any of the techniques, implement any of the functions, and/or be carried out in any of the manners disclosed in any of the following commonly assigned U.S. patent applications: Ser. No. 62/600,000 filed Dec. 18, 2017, by inventor Alexander Bodurka and entitled SMART HOSPITAL HEADWALL SYSTEM; Ser. No. 62/587,867 filed Nov. 11, 2017, by inventors Alexander Bodurka et al. and entitled PATIENT SUPPORT APPARATUSES WITH LOCATION/MOVEMENT DETECTION; Ser. No. 62/598,787 filed Dec. 14, 2017, by inventors Alexander Bodurka et al. and entitled HOSPITAL HEADWALL COMMUNICATION SYSTEM; and Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosures of which are all incorporated herein by reference. As discussed in more detail in any of these patent applications, headwall unit 66 communicates with a room interface board 116 that is in communication with nurse call system 88 and, in most cases, one or more environmental controls for controlling various aspects of the room in which patient support apparatus 22a is located (e.g. television, thermostat, etc.).

In addition to communicating with wireless headwall unit 66, second transceiver 102 of patient support apparatus 22a is, in the embodiment illustrated in FIG. 2, also configured to communicate via mesh networks 76 and 78 with one or more other authorized medical devices 22, such as thermal control unit 22b and/or recliner 22c. As noted, in some embodiments, second transceiver 102 is a Bluetooth transceiver that is able to communicate using any of the conventional Bluetooth mesh network communication protocols (e.g. the Mesh Profile Specification and Mesh Model Specification of Bluetooth Low Energy). In other embodiments, second transceiver 102 utilizes another type of mesh networking communications, such as, but not limited to, any communications meeting the standards set forth in the Institute of Electrical and Electronics Engineers (IEEE) 802.11s. Still other types of mesh network communication protocols may be used.

In the particular embodiment shown in FIG. 2, patient support apparatus 22a also includes a network transceiver 112 that is adapted to communicate with the wireless access points 86 of local area network 82. In some embodiments, network transceiver 112 is adapted to transmit and receive wireless electrical signals using the Wi-Fi protocol, or any of the many non-mesh IEEE 802.11 protocols (e.g. 802.11g, 802.11n, etc.). Network transceiver 112 thereby allows patient support apparatus 22a to communicate with local area network 82, including, but not limited to, one or both of software and validation servers 94 and 96. It will be appreciated by those skilled in the art that patient support apparatus 22a may be modified to combine the functions of second transceiver 102 and network transceiver 112 into a single transceiver that carries out both mesh network communication and communication with local area network 82.

Regardless of the specific communications format used, second transceiver 102 is designed to communicate via one or both of mesh networks 76 and 78 with one or more nearby (those within range) authorized medical devices 22. In addition to thermal control units 22b and/or recliners 22c, such authorized medical devices 22 include, but are not limited to, ventilators, vital sign monitors, respirators, infusion pumps, IV pumps, temperature sensors, surgical equipment, room cleaning equipment, handwashing stations, blood oxygen saturation monitors, and/or other authorized medical devices used in the healthcare facility 80 for caring for patients. In addition, such authorized medical devices 22 may include any of the mesh-network enabled devices disclosed in commonly assigned U.S. Pat. No. 9,937,090 issued Apr. 10, 2018, by inventors Michael Hayes et al. and entitled PATIENT SUPPORT APPARATUS COMMUNICATION SYSTEMS, the complete disclosure of which (including references incorporated therein) is incorporated herein by reference. Still further, such authorized medical devices 22 may include any of the medical devices disclosed in commonly assigned PCT patent application serial number PCT/US2017/041681 filed Jul. 12, 2017, by applicant Stryker Corporation and entitled EQUIPMENT MANAGEMENT SYSTEM, the complete disclosure of which is incorporated herein by reference.

Main mesh network 78 is adapted to transport a variety of different types of data and message that originate from any one of the medical devices 22a and that are destined to either another one of the medical devices 22a, a server on local area network 82, and/or a remote server accessible via the Internet 92 (e.g. server 96). Such data includes, in the case of patient support apparatuses 22a, data from one of more of the sensors 110 positioned on board, such as, but not limited to, information indicating whether the siderails 40 of a patient support apparatus 22a are up or down; whether a brake for wheels 26 is locked or unlocked; the height of the litter frame 30 above base 24 (in those apparatuses where this height can be changed by a user); the angle of one or more deck sections supported on the litter frame 30 (such as a Fowler section); the output from a bed exit system that is incorporated into patient support apparatus 22a (such as, but not limited to, the bed exit system disclosed in commonly-assigned U.S. Pat. No. 5,276,432 issued to Travis and entitled PATIENT EXIT DETECTION MECHANISM FOR HOSPITAL BED, the complete disclosure of which is hereby incorporated herein by reference); information indicating whether a bed exit system is armed or disarmed; the output from a patient movement detection system that is incorporated into patient support apparatus 22a (such as, but not limited to, the patient movement detection system disclosed in commonly-assigned U.S. Pat. No. 6,822,571 issued to Conway and entitled PATIENT MOVEMENT DETECTION SYSTEM FOR A BED INCLUDING A LOAD CELL MOUNTING ASSEMBLY, the complete disclosure of which is also incorporated herein by reference); the output from a patent interface pressure detection system (such as, but not limited to, that disclosed in commonly-assigned U.S. patent application Ser. No. 14/003,157 filed Oct. 14, 2013, by inventors Joshua Mix et al. and entitled SENSING SYSTEM FOR PATIENT SUPPORTS, the complete disclosure of which is incorporated herein by reference); data from one or more medical devices 22 that are either supported on patient support apparatus 22a, or in communication with patient support apparatus 22a (such as via first transceiver 100); information from a video monitoring system (such as that disclosed in commonly assigned U.S. patent application Ser. No. 15/808,465 filed Nov. 9, 2017, by inventors Richard Derenne et al. and entitled VIDEO MONITORING SYSTEM, the complete disclosure of which is incorporated herein by reference); and information from other devices or structures in the room that have wireless communication abilities (such as, but not limited to, the devices disclosed in commonly assigned U.S. Pat. No. 8,320,662 issued Apr. 26, 2016, to inventors Michael Hayes et al. and entitled PATIENT SUPPORT APPARATUS WITH IN-ROOM DEVICE COMMUNICATION, the complete disclosure of which is incorporated herein by reference).

By forwarding information through main mesh network 78 to an access point 86 and/or another medical device 22, the information may be able to avoid bottlenecks, route around weak communication channels, and in some cases avoid areas where communication with an access point 86 is not possible. That is, the data is able to be relayed around bottlenecks, weak communication channels, and/or other areas having poor or non-existent non-mesh communication abilities. The data can also be relayed through separate mesh network channels that are independent of local area network 82, thereby avoiding adding additional burden to the already existent communication load of network 82.

In some embodiments of communication system 20, not only can communication between medical devices 22 themselves be carried out without utilizing local area network 82 or access points 86 (via main mesh network 78), but also communication between medical devices 22 and one or both of local and remote servers 94 and 96 can be carried out without utilizing local area network 82 or access points 86. Such LAN-independent communications can be accomplished by adding an enterprise receiver to servers 94 and/or 96, such as, but not limited to, an enterprise receiver of the type disclosed in commonly assigned U.S. patent application Ser. No. 15/831,466 filed Dec. 5, 2017, by inventor Michael Hayes and entitled NETWORK COMMUNICATION FOR PATIENT SUPPORT APPARATUSES, the complete disclosure of which is incorporated herein by reference. When such an enterprise receiver is added to communication system 20, one or more medical devices 22 are able to communicate directly with the enterprise receiver which is, in turn, in direct communication with server 94 and/or the Internet 92. Medical device to medical device communication is therefore able to take place independent of the IT infrastructure of the healthcare facility 80 (via main mesh network 78), and medical device to server 94, 96, and vice versa, is also able to take place independent of the IT infrastructure of the healthcare facility 80.

In general, mesh network 78 may utilize any of the routing techniques, carry any of the data, and/or serve any of the purposes of the mesh networks disclosed in commonly assigned U.S. Pat. No. 9,937,090 issued Apr. 10, 2018, to inventors Michael Hayes et al. and entitled PATIENT SUPPORT APPARATUS COMMUNICATION SYSTEMS, the complete disclosure of which is incorporated herein by reference.

Each of the medical devices 22 that are part of a particular mesh network 76 and/or 78 at a particular time include a mesh network transceiver 118 (FIG. 2). The mesh network transceiver 118 may be the same type of transceiver as second transceiver 102 of patient support apparatus 22a mentioned above. In general, mesh network transceivers 118 are able to communicate with each other using mesh networking communication principles, and the particular protocols used to carry out those mesh networking principles may vary from embodiment to embodiment.

Each mesh network transceiver 118 is coupled to a controller 120. Controller 120, like controller 104 of patient support apparatus 22a, may include one or more microcontrollers, microprocessors, field programmable gate arrays, systems on a chip, volatile or nonvolatile memory, discrete circuitry, and/or other hardware, software, firmware and/or combinations thereof that are capable of carrying out the mesh network functions described herein, as would be known to one of ordinary skill in the art. Additionally, in some embodiments, controllers 104 may also control other aspects of the medical devices 22 besides the mesh networking communications (e.g. controller 104 may also, for example, control the temperature of the circulating fluid and/or the user interface 50 in the case of thermal control unit 22b). Each controller 104 is in communication with a memory 122, which is preferably a non-volatile memory (e.g. flash) that is used to store, among other items, messages relayed between medical devices 22 on the mesh networks 76, 78.

In some embodiments of communication system 20, each medical device 22 further includes a join button 124 and/or an authenticator chip 126 (FIG. 2). The join button 124, as will be discussed in greater detail below, is pressed by a user when the user wishes the corresponding medical device 22 to join the main mesh network 78. It will be understood that the join button 124 does not literally need to be a button, but can take on other forms, such as an icon on a touch screen, a switch, a knob, or any other type of control that can be selectively activated by a user. The authenticator chip 126, as will be discussed in greater detail below, is used by the corresponding medical device 22 to establish the necessary credentials of the medical device 22 for joining main mesh network 78. In other words, authenticator chips 126 allow their corresponding medical devices 22 to join main mesh network 78, and unauthorized medical devices 22 that do not have such a chip are not allowed to join main mesh network 78. As noted, both the join button 124 and the authenticator chip 126 are optional components that need not be present in every embodiment of communication system 20. Their use in some specific embodiments is described in further detail below.

Figure 3:
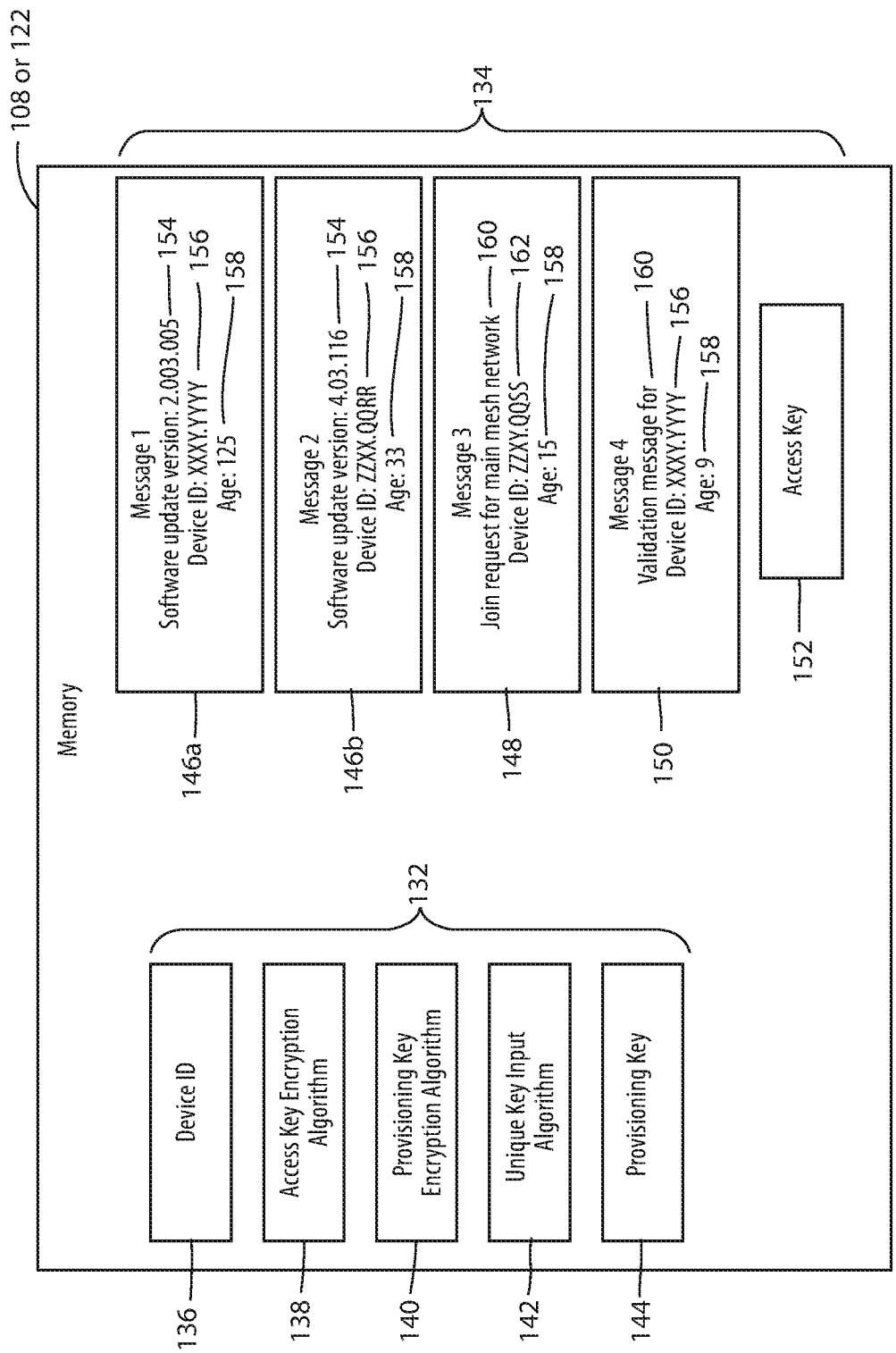
FIG. 3 is a block diagram of an illustrative set of mesh network data stored in the memories of the medical devices that use one of the communication systems disclosed herein.

As shown in FIG. 2, every authorized medical device 22 of communication system 20 is equipped with a mesh transceiver 118 (or 102), a corresponding controller 120 (or 104), and a memory 122 (or 108). As shown in FIG. 3, each memory 108, 122 contains a set of factory-installed data 132 and a plurality of mesh network usage data 134 that is generated and stored during the operation of communication system 20 within a healthcare facility. The factory-installed data includes a device ID 136, an access-key encryption algorithm 138, a provisioning key encryption algorithm 140, a unique key input algorithm 142, and a provisioning key 144. The mesh network usage data 134 will vary with time during usage of the mesh networks, will vary depending upon the particular embodiment of communication system 20 that is installed in a particular healthcare facility, and will vary depending upon the particular data gathered and/or needed by the medical devices 22.

FIG. 3 depicts an example of several different types of usage data 134 that may appear at an arbitrarily selected node of communication system 20. This data includes a first software message 146a, a second software message 146b, a join request message 148, a validation message 150, and an access key 152. As noted, additional data, or less data, may be stored within network usage data 134, depending upon the conditions mentioned above. For example, access key 152 will only be saved on those medical devices 22 that have been authorized and granted access to main mesh network 78, as will be discussed in greater detail below.

Device ID 136 is a unique identifier that uniquely identifies the medical device 22 in whose memory 108 (or 122) it is stored. It may be a serial number, an alphanumeric character string, or any other suitable identifier that distinguishes a particular medical device 22 from other medical devices 22. The device ID 136 may be implemented in some embodiments such that classes of medical devices share some portion of the device ID 136 with each other, thereby enabling identification of what class a particular device belongs to based on the device ID 136. For example, all beds (or particular models of beds) may include a common initial digit, or a common set of initial digits, or some other common characteristic within their device IDs 136. Apart from this common portion of the ID, the rest of the device ID 136 will be unique to each individual bed. Similar types of common characteristics of device IDs may be incorporated into different types of medical devices 22 (e.g. thermal control units, such as thermal control unit 22b, may have common aspects of their device IDs 136; recliners, such as recliner 22c, may common aspects of their device IDs, etc.). As will be discussed in greater detail below, device IDs are used in some embodiments of communication system 20 to determine whether a medical device 22 is authorized to join main mesh network 78 or not.

Access key encryption algorithm 138 (FIG. 3) is used by the corresponding controller 120 (or 104) of a medical device 22 to encrypt and decrypt messages that are transmitted over main mesh network 78. As noted previously, access key encryption algorithm 138 is part of the factory-installed data 132, and it therefore present on all medical devices 22 that are intended by their manufacturer to be able to communicate using main mesh network 78. Provisioning key algorithm 140 is used by the corresponding controller 120 (or 104) of a medical device 22 to encrypt and decrypt messages that are transmitted over provisioning mesh network 76. Unique key input algorithm 142 is used by the corresponding controller 120 if that particular medical device 22 is used as the validation node of a particular main mesh network 78, as will be discussed in greater detail below. Provisioning key 144 is used as an input into the provisioning key encryption algorithm 140. In some embodiments, provisioning key 144 may be an integrated into provisioning key encryption algorithm 140, rather than separately stored.

First software update message 146a (FIG. 3) is an example of a type of message that a medical device 22 coupled to main mesh network 78 may receive and temporarily store in memory. Software update messages 146 are used to update the software used by one or more medical devices 22 that are part of main mesh network 78. Each software update message 146 includes a version identifier 154, a recipient identifier 156, and an age identifier 158. Although not shown, each software update message 146 also includes a payload, which contains all or a portion of the new software that is to be installed on the medical device 22 identified by the recipient indicator 156. The version identifier 154 identifies the version of software, or software portion, stored in the payload of the message 146. This enables the recipient to determine whether it has already received that particular software update (from, for example, another device on main mesh network 78). The version identifier 154 is also stored by the recipient so as to be able to determine whether and/or when future software updates are necessary.

The recipient identifier 156 of a software update message 146 identifies the intended recipient of the message 146. In the example shown in FIG. 3, the device ID 136 of a medical device 22 is used as the recipient identifier 156. That is, when a message is to be transmitted to a particular medical device 22 on main mesh network 78, such as, for example, a medical device 22 having a device ID of XXXY.YYYY (see message 146a of FIG. 3), the message contains the device ID XXXX.YYYY within the recipient indicator field 156 of the message. Each intermediate recipient of the message checks this device ID with its own device ID 136 and, if it matches, processes the message 146. If it does not match, the message 146 is relayed onto another medical device 22 that is part of main mesh network 78. The use of main mesh network 78 for updating the software of medical devices 22 that are part of main mesh network 78 is discussed in greater detail below with respect to FIGS. 17-21.

The age indicator 158 (FIG. 3) is a data field that indicates how old a particular message is that is contained within the mesh network usage data 134 of memory 108 or 122. Although FIG. 3 indicates age indicator 158 as being part of messages 146a and 146b, it is to be understood that age indicator 158 is not actually transmitted between medical devices 22. Instead, age indicator 158 correspond to data that a medical device 22 associates with a particular message after receiving the message and thereafter uses to keep track of how long ago that particular message was received. In some embodiments, age indicator 158 is stored as the time at which a particular message was received. In other embodiments, age indicator 158 may simple be a count value corresponding to an internal clock contained within medical device 22. Still other manners of measuring the age of a message may be used.

Regardless of the specific manner in which the age of the message is recorded, controller 104, 120 uses the age field to determine how long to maintain the message within its memory 108, 122. That is, once a message has remained within memory 108, 122 for more than a threshold amount of time, controller 104, 120 deletes it. Age indicator 158 therefore provides a manner for controller 104, 120 to manage the contents of memory 108, 122 and prevent it from being overloaded with too much data. Indeed, age indicator 158 may also be used to determine the order in which messages are deleted before they have reached their expiration threshold in situations where a particular medical device 22 is receiving more messages at a particular time than it has room to store within memory 108, 122.

FIG. 3 illustrate another example of a software update message 146b. Software update message 146b, like message 146a, includes a version identifier 154, a recipient identifier 156, and an age indicator 158. Software update message 146b differs from software update message 146a in that it contains different software (or a portion of software) than message 146a, is intended for a different recipient, and was received more recently than software message 146a (e.g. it has a lower age value). Controller 104, 120, however, treats software messages 146b in the same manner as software update message 146a. That is, it relays the message 146 onto one or more other medical device 22 that are within range and part of main mesh network 78 (and different from the medical device 22 it originally received the messages 146 from).

FIG. 3 also illustrates a join message 148 contained within usage data 134. Join messages 148 are sent by medical devices 22 that have not yet joined main mesh network 78, but wish to do so. That is, a medical devices 22 are programmed to send out a join request message 148 after they have established communication with provisioning mesh network 76. The join request message 148 requests that the particular medical device 22 be granted access to main mesh network 78. As will be discussed in greater detail below, a medical device 22 is only able to join main mesh network 78 after it has received an access key 152 from a validation node (discussed more below) of main mesh network 78. Join messages 148 are therefore requests for access keys 152 from a validation node of main mesh network 78.

As shown in FIG. 3, join messages 148 include a message identifier field 160 that contains data identifying the message as a join request. The particular data and/or data structures used to form this identification may vary from embodiment to embodiment. Indeed, in some embodiments, all messages of main mesh network 78 may include a message identifier field 160 that identifies what type of message they are (e.g. a software update message, join message, validation message, heartbeat message, etc.). Join request message 148 also includes a sender identifier 162 and an age identifier 158. Sender identifier 162, unlike recipient identifier 156, identifies the medical device 22 that sent the join request message, rather than the intended recipient of message 148. Join request messages 148, in some embodiments of communication system 20, do not include a recipient identifier 156 because the intended recipient of the join request message—the validation node (discussed more below)—may not be known to the sender of message 148. Age identifier 158 identifies how long ago medical device 22 received the join message 148.

Validation message 150 also includes a message identifier field 160 that contains data identifying the message as a validation message (FIG. 3). The particular data and/or data structures used to form this identification may vary from embodiment to embodiment. Validation message 150 also includes a recipient identifier 156 and an age identifier 158. Recipient identifier 156 and age identifier 158 operate in the same manners previously described with respect to messages 146 and/or 148. As will be discussed in greater detail below, validation messages 150 are sent after a medical device 22 has requested (via a join request message 148) to join main mesh network 78 and a validation node of the main mesh network 78 has determined that the requesting medical device 22 is authorized to join main mesh network 78.

It will be understood that additional data and/or indicators may be included within any of messages 146a, 146b, 148, and/or 150 beyond what is shown in FIG. 3 and what has been discussed so far herein. Such additional data may include, but is not limited to, a portion identifier that identifies the particular portion of software contained within messages 146, and/or a sequence identifier that identifies the sequence in which the software messages 146 are to be interpreted and/or assembled by the recipient, and/or still other data. Such additional data may also, or alternatively, include a unique message identifier that uniquely identifies each message. Such a unique message identifier, if included, is used in some embodiments by controllers 104, 120 to maintain a log of which messages it has already received and which messages it has already transmitted (as well as the recipients of the transmitted messages). Such a log assists the controllers 104, 120 in avoiding the retransmission of the same message to the same recipient. Still other data may be included in one or more of these messages.

Messages 146, 148, and 150 in FIG. 3 are examples of messages that are temporarily stored in memory 108 or 122 in order to be relayed to another node on main mesh network 78. If any of these message were intended for the particular medical device 22 in whose memory they are shown as being stored in FIG. 3, the corresponding controller 104, 120 would decipher the message and act accordingly, rather than merely store the message for re-transmittal. More detailed discussions of how each of these messages are deciphered by their intended recipients are discussed below.

ments; whether at least one server is used; whether all of the authorized medical devices 22 need to be added to main mesh network 78 manually; whether the first medical device 22 (initial) of the main mesh network 78 is manually configured; whether the main mesh network 78 uses encryption (and/or other security measures) that are unique to the specific healthcare facility 80 in which the main mesh network 78 is installed; and the level of security provided by each of the embodiments of communication systems 20-20f.

TABLE 1

| Ref. | General Provisioning | Specific Provisioning | FIGS. | # | Server access? | All manual? | Initial Manual? | Facility Specific? | Security |
|---|---|---|---|---|---|---|---|---|---|
| 20 | Separate Provisioning Mesh 76 | Valid IDs | 4-6 | 2 | Yes | No | Yes | Yes | High |
| 20a | | Authenticator Chips | 7-8 | 2 | No | No | Yes | Yes | High |
| 20b | | Manual | 9-10 | 2 | No | Yes | Yes | Yes | Med |
| 20c | Valid ID Range | Manual Entry | 11-13 | 1 | No | Yes | Yes | Yes | Med |
| 20d | Static Keys | Facility-specific encryption | 14-15 | 1 | No | Yes | Yes | Yes | Med |
| 20e | | none | none | 1 | No | No | No | No | Low |
| 20f | Manual | None | 16 | 1 | No | Yes | No | No | Low |

It will be understood that, in some embodiments, controller 104, 120, may retain messages within memory 108, 122 even after having relayed the messages to another medical device 22 on main mesh network 78. By retaining the messages after relaying them to one or more recipients, controller 104 preserves the ability to re-transmit the messages to still other medical devices 22 that are part of main mesh network, but weren't within range at the time the messages were originally relayed. In other words, if a medical device 22, such as medical device 22a of FIG. 4, receives a message from medical device A and relays it to medical device C over main mesh network 78, it may retain the message for a threshold amount of time in case another medical device (not shown in FIG. 4) that is part of main mesh network 78 comes within range of medical device A.

It will also be understood that the threshold length of time in which messages to be relayed are stored in memory 108, 122 may vary. In some embodiments, threshold storage time may depend upon the physical location of the medical device in relation to other medical devices on the main mesh network 78, the number of medical devices 22 that the message has already been relayed to, and/or the type of message. With respect to this last category, the threshold time storage may vary according to the type of message such that some types of messages are retained in memory 108, 122 for longer time periods and other types of messages are retained in memory 108, 122 for short time periods.

Figure 4:
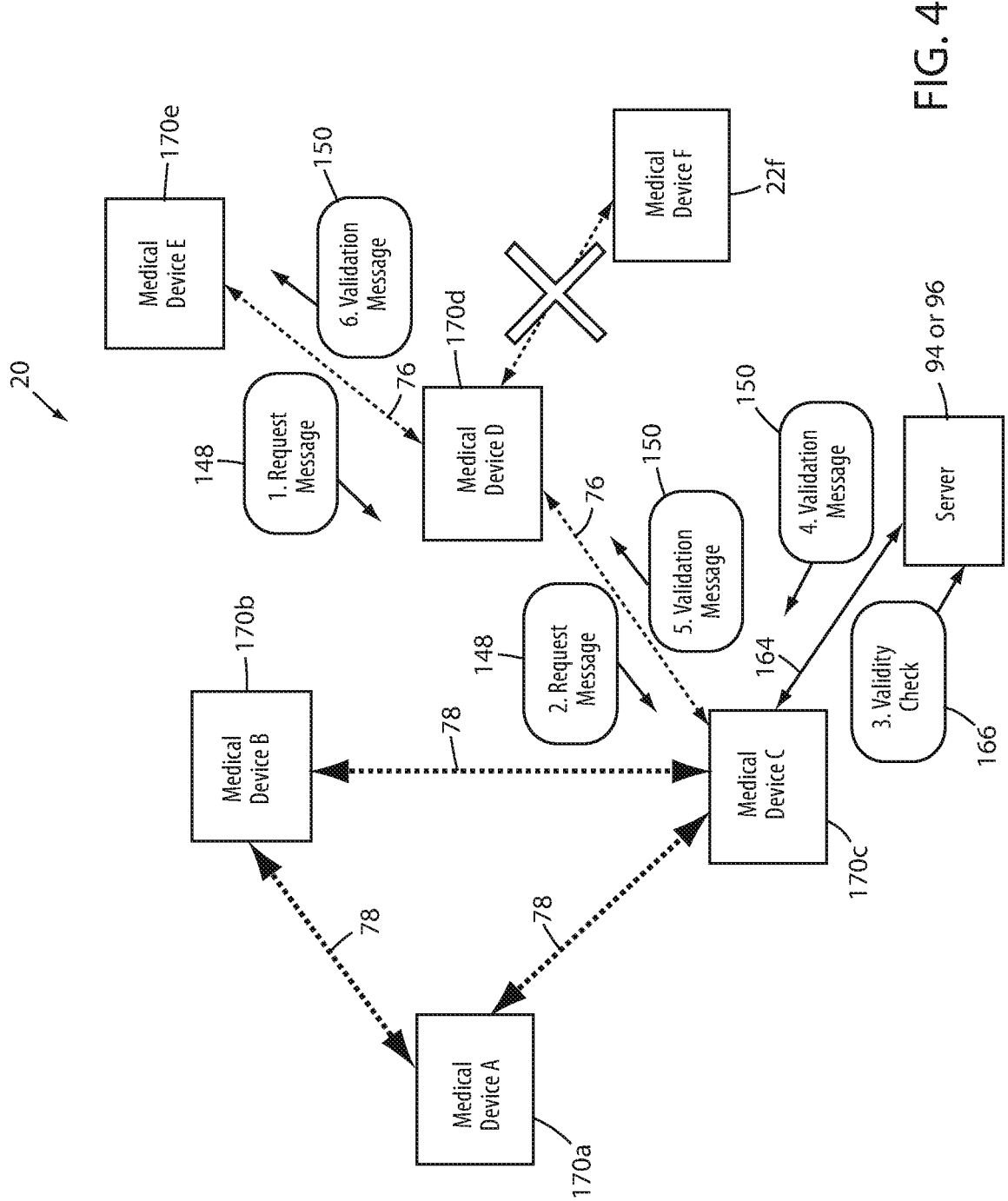
FIG. 4 is a block diagram of a plurality of medical devices illustrating a method of adding devices to a main mesh network according to a first embodiment of the communication system.

Communication system 20 may be implemented in a number of different embodiments. These embodiments differ from each other primarily in how main mesh network 78 is established and/or accessed. Table 1 below identifies seven different communication system embodiments 20, 20a, 20b, 20c, 20d, 20e, and 20f, along with several characteristics of each of the different embodiments. These characteristics are listed in the columns of Table 1 and include, starting in the second column to the left and proceeding rightward, the following: a general manner in which the provisioning of main mesh network 78 takes place; a more specific manner in which the provisioning of main mesh network 78 takes place; the figures that corresponds to each of these embodiments 20-20f; the number of mesh networks (e.g. 76 and/or 78) in each of these embodi- FIG. 4 shows an arbitrary layout of communication system 20 and illustrates one manner in which authorized medical devices 22 are configured to join main mesh network 78. A medical device 22 is an authorized medical device 22 if it has an authorized device ID 136 and is programmed with the proper instructions and data for the controller 120 to be able to form a node 170 of one or both of mesh networks 76 and 78 (FIG. 3). Such programming and data includes, as discussed above, algorithms 138, 140, and 142 and keys 144 and 152. By restricting access to mesh networks 76 and 78 to only medical devices 22 having the proper keys 144 and 152, security for the mesh networks 76, 78 is provided against unauthorized usage of the mesh networks 76, 78, as well as unauthorized reading of the contents of messages transmitted over these networks 76, 78. In the example of FIG. 4, medical device 22f is not an authorized medical device 22 and therefore is not able to join either provisioning mesh network 76 or main mesh network 78.

Devices 22 are authorized by the provider of communication system 20, which may be the manufacturer of medical devices 22 or an entity licensed, or otherwise permitted, by the provider of communication system 20 to use the mesh networks 76, 78. In order to authorize a particular medical device 22, as will be discussed in more detail below, the device ID 136 of the medical device 22 must be added to a list of device IDs 136 that are authorized for a particular healthcare facility 80. This list is maintained on local server 94 and/or remote server 96. Authorized medical devices 22 must also include the programming and data discussed above that enable it to communicate over the mesh networks 76, 78. For purposes of brevity, each authorized medical device 22 of mesh networks 76 and/or 78 will be referred to as a node 170 of these networks and medical devices 22 that are not authorized will not be referred to as nodes of these networks 76, 78.

Each of the nodes 170 of mesh networks 76 or 78 is able to communicate with other nodes 170 that are within communication range. Each node 170 is therefore able to not only disseminate data that originates from its own internal sensors (e.g. sensors 110), but also to serve as a relay for forwarding information it receives from other nodes 170 to still other nodes 170, or to one of servers 94, 96 (or to another application/server on healthcare network 82). Because the positions of the nodes 170 will likely change over time, the mesh networks formed by the nodes 170 may be dynamic such that the data paths change with changing locations and/or other conditions.

Main mesh network 78 of communication system 20 is used for communicating data between individual nodes 170 and/or for communicating data from server 94 (or 96) to nodes 170 or vice versa. Provisioning mesh network 76 is used to control the access of medical devices 22 to main mesh network 78. That is, provisioning mesh network 76 provides the provisions to the authorized devices 22 necessary for them to join main mesh network 78. These provisions include an access key 152 (FIG. 3) that is used by medical devices 22 to communicate over main mesh network 78. Access key 152 is used by the medical devices 22 to encrypt and decrypt their messages, thereby only allowing medical devices 22 having such a key to communicate over main mesh network 78.

The dissemination of the access keys 152 to authorized medical devices 22 is carried out by provisioning mesh network 76. Provisioning mesh network 76 therefore controls which medical devices 22 are able to join main mesh network 78 and, in some embodiments, carries out the process for joining nodes to main mesh network 78 automatically, thereby relieving any technicians or other personnel from having to take any manual steps to allow a device 22 to join main mesh network 78.

In the example of communication system 20 shown in FIG. 4, a plurality of nodes 170a-c have joined main mesh network 78, a plurality of nodes 170d and 170e are part of provisioning mesh network 76, and an unauthorized medical device 22f is not part of either main mesh network 78 or provisioning mesh network 76. In communication systems 20, 20a, and 20b, the nodes 170 use provisioning mesh network 76 to join main mesh network 78. An example of this process is shown with respect to node 170e of FIG. 4. Node 170e uses provisioning network 76 to join main mesh network 78 by sending a join request message 148 to whatever nodes 170 that are within range. In this particular example, the only node 170 within range of this join request message 148 is node 170d. The join request message 148, as discussed above, includes a request to join main mesh network 78, as well as the data discussed above with respect to FIG. 3.

As noted previously, the join request message 148 may not include an intended recipient because node 170e may not know the identity of the intended recipient. The intended recipient of all join request messages 148 in communication system 20 is a validation node. The validation node in the particular example of FIG. 4 is node 170c. Node 170c is the validation node because it is in direct communication with server 94 and/or 96 via communication channel 164. In a given installation of communication system 20, there may be more than one validation node within main mesh network 78—each with its own communication channel 164 to server 94 and/or 96—but only one such validation node is shown in the example of FIG. 4.

Communication channel 164 is, in some embodiments, a wired connection between the validation node 170c and local area network 82. In other embodiments, communication channel 164 is a wireless connection between the validation node 170c and local area network 82. When implemented as a wireless connection, channel 164 may include WiFi communications between node 170c and one or more wireless access points 86 of network 82. If node 170c happens to a be a patient support apparatus, such as patient support apparatus 22a of FIG. 2, communication channel 164 would be established by network transceiver 112 communicating with one or more wireless access points 86, which are, in turn, in communication with server 94 and/or server 96 (via the Internet 92).

Because node 170d is not a validation node in the example of FIG. 4, it relays the request message 148 to one or more medical devices 22 that are within its range. In this case, validation node 170c is the only device positioned within range and therefore is the only medical device that receives the join request message 148 from node 170d. Validation node 170 sends a validity check message 166 to server 94 or 96 over communication channel 164. The validity check message 166 includes the device ID contained within the join request message 148 to server 94. The recipient of validity check message 166 (server 94 or 96) compares the device ID contained within that message to an authorized list of devices that is maintains in its memory (or a memory accessible to it). The authorized list of medical devices identifies each medical device that has been approved to join the mesh network 78 within a particular healthcare facility 80. In some embodiments, this list is maintained by the administrators of the healthcare facility, while in other embodiments, this list is maintained by the manufacturer or seller of the authorized medical devices 22. Still other entities may be involved in maintaining this list.

If server 94 or 96 matches the device ID 136 contained within the validity check message 166 to a device ID maintained on the list of authorized devices, it determines that that particular medical device (in this example, medical device E) is an authorized medical device. If server 94 or 96 does not find the device ID 136 contained within the validity check message 166 in the list of authorized devices, it determines that that particular medical device (e.g. medical device E) is not an authorized medical device. In either case, server 94, 96 sends a validation message 150 back to validation node 170c indicating whether the requesting medical device (e.g. medical device E) is or is not authorized to join main mesh network 78 or not.

Validation node 170c forwards the validation message 150 to one or more nodes 170 that are positioned within its range. Although FIG. 4 only shows the validation message 150 being forwarded to medical device D (node 170d), validation node 170c would also forward validation message 150 to nodes 170a and 170b, assuming they are both within range of node 170c. After receiving the validation message 150, node 170d forwards the validation message to node 170e. If the validation message indicates that node 170e is an authorized medical device, then the validation message 150 will also include access key 152. As noted previously, the access key 152 may be originally included within message 150 by server 94 or 96, or it may be added by any of the intervening nodes 170 that are part of main mesh network 78 (e.g. node 170c in this case).

Node 170e joins the main mesh network 78 by using the received access key 152 (assuming it was an authorized medical device) with its access key encryption algorithm 138 to encrypt and decrypt messages transmitted over main mesh network 78. In some embodiments, a node 170 that recently joins main mesh network 78 begins periodically transmitting heartbeat type messages indicating its presence and the fact that it is part of main mesh network (using encryption enabled by access key 152). In other embodiments, a node 170 that recently joins main mesh network 78 begins listening for message transmitted over the main mesh network 78 and responds if/when one is detected. In still other embodiments, a node 170 that recently joins main mesh network 78 does both: listens and transmits messages using the encryption enabled by the access key 152 and encryption algorithm 138.

It will be understood that the process for joining main mesh network 78 is the process by which an authorized node 170 gains an access key that is necessary to encrypt and decrypt messages over main mesh network 78. That is, any device (whether authorized or not authorized) that includes RF communication abilities capable of listening at the frequency(ies) used by main mesh network 78 can detect the messages being transmitted back and forth over the main mesh network 78. However, only authorized devices will have the access key 152 necessary to decrypt, and thus understand, the transmitted messages. The phrase "joining main mesh network" and the like, as used herein, therefore refers to the process by which a node gains the required access key 152 necessary to encrypt and decrypt messages that travel over main mesh network 78.

Access to provisioning mesh network 76 is ensured prior to the medical device 22 being installed within a healthcare facility. That is, each authorized medical device 22, either at the time of manufacture, or prior to delivery to a healthcare facility 80, has a provisioning key 144 and provisioning key algorithm 140 installed within its memory 108 or 122. The medical device's controller (104 or 120) uses the provisioning key 144 and provisioning key algorithm 140 to encrypt and decrypt messages that are transmitted over provisioning mesh network 76. Because provisioning key 144 is installed in the memory of the medical devices 22 prior to the device being installed in a healthcare facility 80, unlike access key 152 which is added to a medical device's memory after being installed within a healthcare facility 80, authorized medical devices 22 are able to communicate over provisioning mesh network 76 immediately upon installation at a medical facility 80. This ability to communicate over provisioning mesh network 76 requires no additional steps on the part of any users, technicians, etc. (at least for communications system 20 and 20*a*).

None of the medical devices 22, however, have the ability to communicate over main mesh network 78 when they are first installed in a medical facility 80. Instead, they must be given an access key 152 (or an input to algorithm 142, as discussed below). In the communication system 20 of FIGS. 4-6, the access key 152 for the main mesh network 78 of a particular healthcare facility 80 is generated by having a user manually input a unique key into one of the authorized medical devices 22. Once this unique key is input into one of the medical devices 22, the medical device uses unique key input algorithm 142 to generate the access key 152 for that particular main mesh network 78. The medical device 22 that generated the key 152 then shares this key with all medical devices 22 that wish to join main mesh network 78 and that have been validated via server 94 or 96. Thus, in order to institute communication system 20 within a particular healthcare facility 80, only two steps need to be taken by a technician (or other appropriate personnel). First, the unique key has to be input into one of the medical devices 22 (any of the authorized medical devices 22 can be selected by the technician for this purpose), and second, the list of authorized medical devices 22 for that particular healthcare facility 80 has to be generated and stored on either server 94 or 96.

The method by which an authorized medical device 22 generates the access key for a particular healthcare facility will now be described with respect to FIG. 5. Before turning to the details of FIG. 5, an explanation is provided regarding some of the terminology used in FIG. 5, as well as in FIGS. 6-16. In all of these drawings, the term "tech" refers to a technician or other individual who is authorized to set up communication system 20 (or any of the other communication system embodiments 20*a-f*) in a particular healthcare facility. The term "new device" refers to an authorized medical device 22 that has not yet joined main mesh network 78. The term "device in range" refers to an authorized medical device 22 that is within range of the transmitting authorized medical device 22. The term "server" refers to either server 94 or 96.

The term "device connected to the Internet" in FIGS. 6-16 refers to the validation node (e.g. validation node 170*c* of FIG. 4), and, as noted above, this validation node does not necessarily have to be connected to the Internet, but instead can be merely coupled to local area network 82 and local server 94 if local server 94 contains the list of authorized medical devices 22. If local server 94 does not contain this list, then the term "device connected to the Internet" refers to a medical device 22 that is indeed coupled the Internet. Regardless of whether the validation node is connected to local server 94 or to remote server 96, the connection of the validation node to one or both of these servers is a connection that does not utilize any nodes of the mesh networks 76 or 78. In other words, a validation node is not a node that requires either mesh network 76 or 78 to relay its messages to or from server 94 or 96, but instead is a node that can communicate with server 94 or 96 independently of mesh networks 76 and 78.

Figure 5:
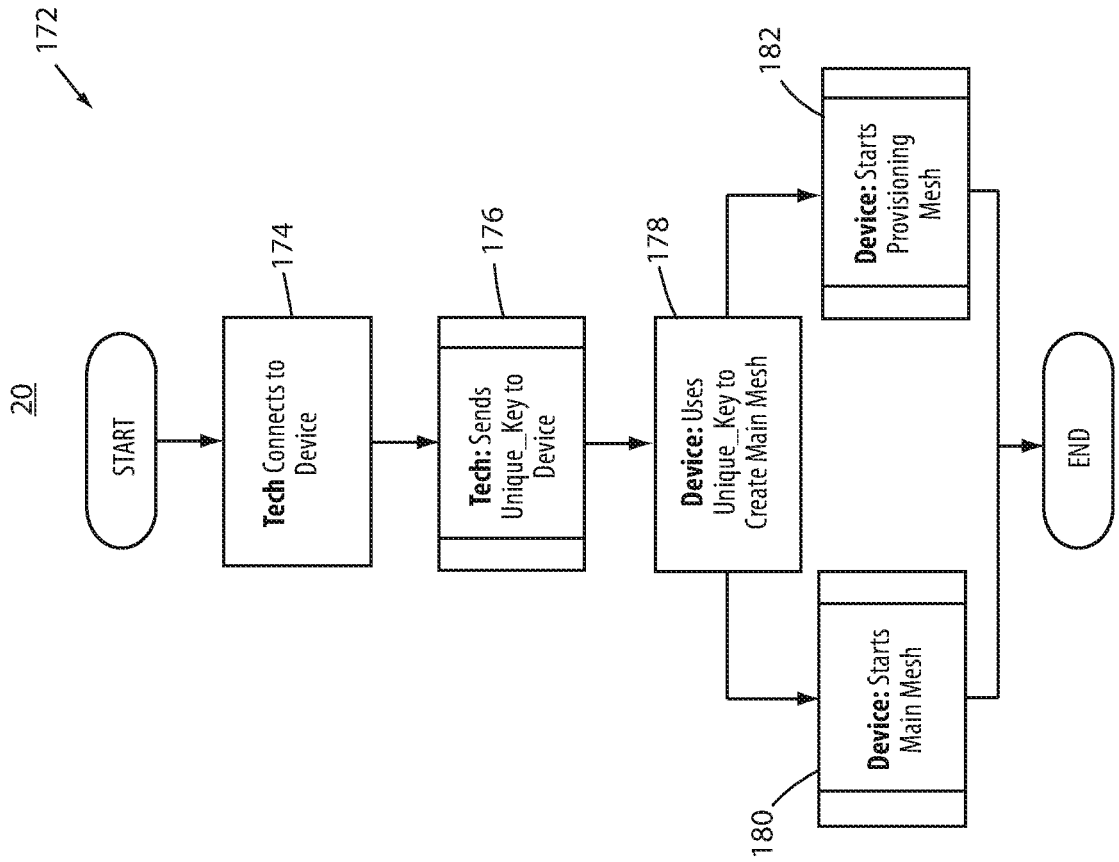
FIG. 5 is a flow diagram of a method for installing a main mesh network key on a first medical device according to the first embodiment of FIG. 4.

FIG. 5 illustrates one method of setting up the first node 170 of a main mesh network 78 in communication system 20. More specifically, FIG. 5 illustrates a first node initialization method 172 that is used with communication system 20. First node initialization method 172 begins at step 174 when a technician connects to an authorized medical device 22 that will become the first node of a main mesh network 78 within that particular healthcare facility 80. In other words, method 172 begins before main mesh network 78 is configured and before any nodes 170 are able to communicate over main mesh network. 78. The particular node selected by the technician for carrying out step 174 of method 172 is selected at the discretion of the technician. In theory, the node selected at step 174 can be any authorized medical device 22 within healthcare facility 80. In practice, the technician may select a particular medical device 22 to connect to at step 174 (and thus be the first medical device 22 of main mesh network 78) based on whether or not the medical device 22 is currently in use, whether the medical device 22 is within range of other authorized medical devices 22, and/or whether the medical device has a non-mesh network connection to local area network 82 and/or the Internet 92 (e.g. whether the medical device 22 is coupled to a communication channel 164).

Once the technician selects a medical device 22 to connect to at step 174, the technician connects to the selected medical device 22 and sends a unique key to that selected medical device. The process of connecting to that medical device 22 and sending the unique key can vary. Depending upon the particular medical device 22 selected, the process may involve any of the following: inserting a thumb drive into a port of the selected medical device 22, such as, but not limited to, a Universal Serial Bus (USB) port, wherein the thumb drive has the unique key stored thereon that is then read by the selected medical device 22; pressing and/or otherwise manipulating one or more buttons or other controls on a user interface of the selected medical device 22 in order to manually input the unique key into the selected medical device 22; or sending a message, file, or other data structure to the selected medical device 22 that contains the unique key. In this last case, the message, file, or other data structure can be sent from the technician's smart phone, laptop, or other computer and can be transmitted via a wired connection (e.g. Ethernet cable, USB cable, etc.) or a wireless connection (e.g. Bluetooth, ZigBee, WiFi, etc.). Whether using a wired connection or a wireless connection, the unique key is transmitted directly to the selected medical device 22 in some cases, while in other cases, the transmission may traverse one or more computer networks (e.g. local area network 82).

Regardless of the specific manner used to communicate the unique key to the selected medical device 22, the unique key is a key that is unique to a particular healthcare facility 80. In some embodiments, the unique key is an alphanumeric string of characters that is based on one or more characteristics of the healthcare facility 80 it is used in, such as a street address, a postal code, a customer number, geographic coordinates, a date of installation of system 20, a name or initials of an installer, a combination of one or more of these items, or still other items. Alternatively, the unique key may be selected at random with no connection to any characteristics of the healthcare facility 80 it is used in. As yet another alternative, the unique key may be a combination of a random component mixed with a component based on one or more characteristics of the healthcare facility 80 it is to be used in. One of more of the inputs into the random number generator are based on the outputs from one or more sensors onboard the selected medical device 22, in at least some embodiments, such as, but not limited to, force sensors, temperature sensors, sound sensors, light sensors, pressure sensors, etc.

The precise manner of generating the unique key can vary widely. In at least some embodiments, the unique key is unique to a particular healthcare facility 80. Thus, healthcare facility A will have a different unique key than healthcare facility B and healthcare facility C and so on. In some cases, a healthcare facility 80 can be further subdivided according to wings, floors, buildings, and/or other structures such that each subdivision has its own unique key and its own separate main mesh network 78. In such cases, each subdivision includes its own access key and initialization method 172 must be performed at least once for each subdivision. Still further, in some embodiments, the unique key is implemented as a rolling or dynamic unique key in which a variable offset from the key is calculated by each of the authorized nodes on a periodic basis. The periodic basis may vary widely, but in some embodiments has a frequency on the order of once per minute. Each authorized node includes an algorithm for calculating the offsets from the key so that all authorized nodes are able to update the key in substantial synchronicity.

Regardless of how granular main mesh network 78 is or is not subdivided for a particular healthcare facility 80, the unique key (or keys) transferred to the selected medical device 22 at step 176 (FIG. 5) is subsequently used at step 178 to create the access key 152 for that particular main mesh network 78. At step 178, the initial medical device 22 that received the unique key at step 176 utilizes its on-board unique key input algorithm 142 to generate the access key 152 for main mesh network 78. That is, the unique key received at step 176 is used as an input into algorithm 142 to generate the access key 152 for main mesh network 78. Algorithm 142 may involve a hash function, a hash table, or any other known algorithm for converting the unique input key into an access key 152.

Once the access key is created at step 178, the selected medical device starts the main mesh network 78 at step 180 and/or starts the provisioning mesh network 76 at step 182. The manner in which the selected medical device 22 starts main mesh network 78 and/or the provisioning mesh network 76 may vary. In some embodiments, the controller 104 or 120 of the medical device 22 starts either or both of these mesh networks by periodically broadcasting messages using the corresponding encryption of each of the mesh networks 76, 78. In essence, the controller 104, 120 and its associated transceiver begin acting as a beacon and announcing the presence of mesh network 76 and/or 78. In other embodiments, the controller 104 or 120 of the medical device 22 starts listening for messages broadcast by other medical devices using the encryption of mesh network 76 or 78 (although, if the medical device 22 is the first to be installed with the unique key and has not yet shared it with other medical devices, no other medical devices 22 will yet have the access key for sending a message over main mesh network 78). In still other embodiments, controller 104, 120 executes steps 180 and 182 (FIG. 5) by a combination of transmitting periodic messages over mesh networks 76, 78 and listening for messages transmitted by other medical devices 22 over either of these networks.

Figure 6:
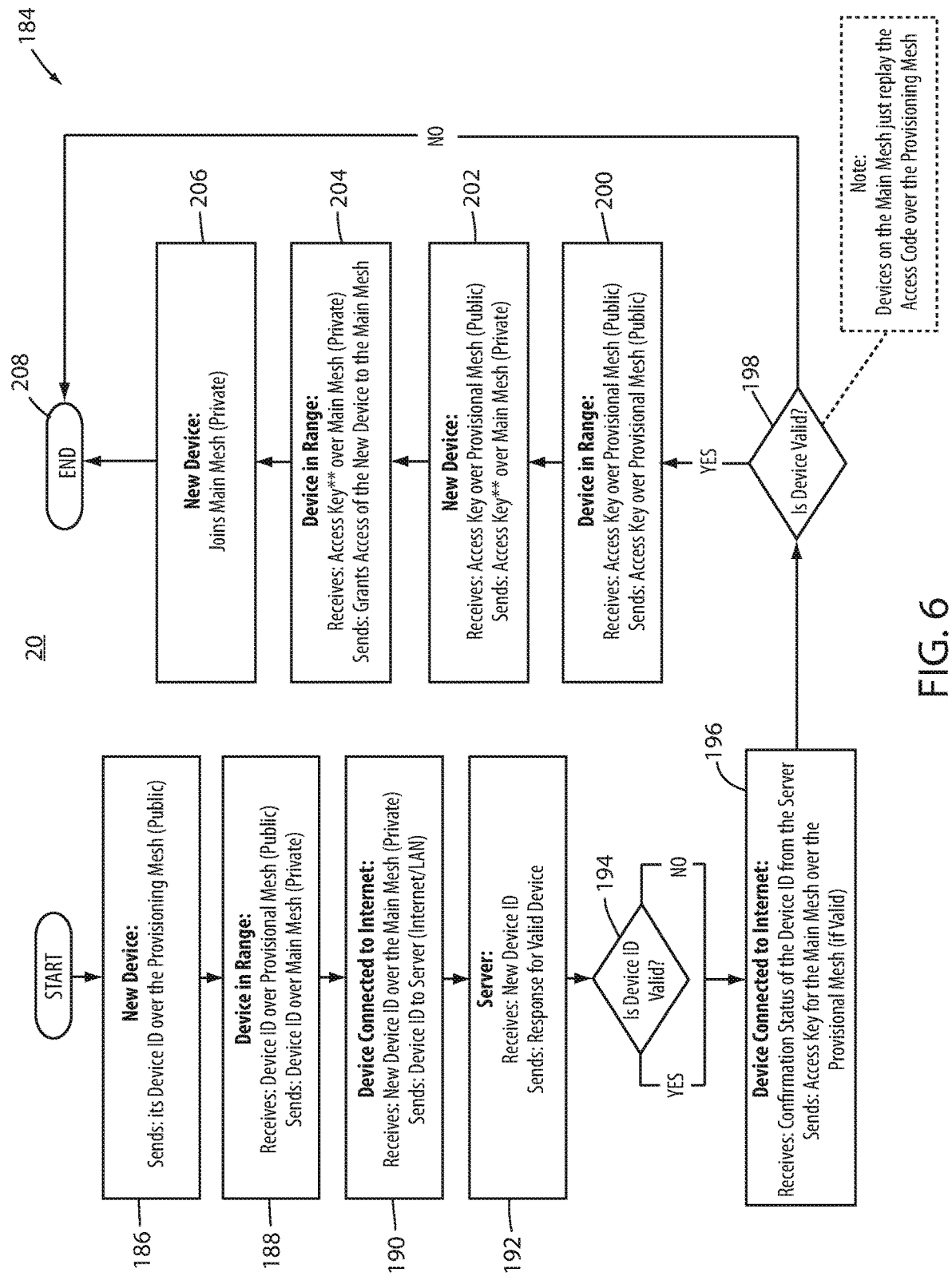
FIG. 6 is a flow diagram of a method for subsequently installing the main mesh network key of FIG. 5 on additional medical devices according to the first embodiment of FIG. 4.

FIG. 6 depicts one method of setting up the subsequent nodes 170 of main mesh network 78 with the access key 152 after the first node has been set up using first mode initialization method 172 of FIG. 5. That is, FIG. 6 illustrates a subsequent node initialization method 184 that is used with communication system 20 for setting up all of the rest of the nodes 170 in main mesh network 78 after first initial method 172 has been executed. Method 184 distributes access key 152 to all of the nodes that are authorized to receive it. As will be explained further below, method 184 includes checking to see that each node 170 is on the previously discussed master list of authorized nodes maintained by server 94 and/or 96. Method 184 therefore not only distributes access key 152 to all nodes 170 after the initial node is set up using method 172, it also verifies that those nodes are on the authorized list and, if they are not, does not distribute the access key 152 to them. Method 184 therefore ensures that only authorized nodes 170 receive the access key 152 to main mesh network 78.

Method 182 begins at step 186 when a new device sends a request to join main mesh network 78. The term "new device" in FIG. 6 refers to an authorized medical device 22 that has not yet received access key 152 for the healthcare facility 80 it is positioned within and is therefore unable to communicate over main mesh network 78. Step 186 therefore refers to a medical device 22 sending a join request message 148 over provisioning mesh network 76. The join request message 148 includes the device ID 136 of the medical device 22 that is sending the message 148 (the "new device"). All medical devices 22 are programmed to send out such a join request message 148 whenever they turn on, or at other designated times, after they detect another medical device 22 within range via the provisioning mesh network 76. No human intervention is therefore required for any subsequent device 22 (after the initial medical device of method 172 of FIG. 5) to join main mesh network 78.

At step 188 (FIG. 6), any medical devices 22 that are positioned within range of the new device receive the join request message 148. For those medical devices 22 that receive the join request message 148 at step 188 and that are not the validation node, they relay the join request message 148 to other medical devices 22 that are within range. They relay message 148 using main mesh network 78 if they are able to and, if not, they relay message 148 using provisioning mesh network 76. Such relaying of the join request message repeats itself over and over again as many times as necessary until the join request message 148 reaches, at step 190, a medical device 22 that functions as the validation node. In some embodiments, the validation node is a medical device 22 coupled to the Internet (and thus server 96) while in other embodiments, the validation node is a medical device 22 coupled to local network 82 (and thus server 94) but not able to communicate over the Internet. In still other embodiments, the validation node may be able to communicate with both server 94 and 96. As noted previously, such communication is independent of mesh networks 76, 78 and may utilize communication channel 164, wireless access point 86, and/or the infrastructure of local area network 82.

At step 190 (FIG. 6), the validation node transmits the join request message 148 to server 94 or server 96 (depending upon where the master validation list is stored for that particular healthcare facility 80). The server 94 or 96 receives the join request message 148 at step 192 and determines at step 194 whether the device ID 136 contained within the join request message 148 is a valid device ID or not. Server 94 or 96 performs this task by comparing the device ID contained within the join request message 148 to the authorized devices listed on its list of authorized medical devices 22. If the device ID matches an entry on this list, the server 94 or 96 concludes that the join request message 148 came from an authorized medical device 22 and should receive access key 152. If the device ID 136 does not match an entry on this list, the server 94 or 96 concludes that the join request message 148 did not come from an authorized medical device 22 and therefore should not receive access key 152.

The authorized list of medical device 22 maintained on server 94 or 96 may be generated in a variety of different manners. In one embodiment, the authorized list is generated and/or maintained by the entity that sells the medical devices 22 to the healthcare facility 80. In such a case, the entity simply records the device IDs 136 of the medical devices 22 that is sells to that particular healthcare facility 80. In another embodiment, the authorized list is generated and/or maintained by personnel of the healthcare facility 80 (e.g. by recording the device IDs 136 of the medical devices 22 it purchases). In still other embodiments, a third party may oversee the generation and/or maintenance of this list by coordinating with personnel of the healthcare facility 80 and/or the manufacturers/sellers of the medical devices 22.

At step 192, server 94 or 96 sends a validation message 150 back to the validation node of main mesh network 78. The validation message 150 includes data indicating whether or not the medical device 22 that sent the join request message 148 is an authorized medical device 22 or not. The validation node 170 reads the contents of the validation message 150 at step 196 and determines at step 198 whether to forward access key 152 to the requesting medical device 22 or not. If the requesting medical device 22 is not on the authorized list of medical devices and thus not an authorized medical device 22, the validation node skips from step 198 to step 208 where it terminates method 184. If the requesting medical device 22 is on the authorized list of medical devices, and therefore authorized to join main mesh network 78, the validation node sends access key 152 to one or more medical devices 22 that are positioned within range of the validation node. The validation node sends the access key 152 over main mesh network 78 to those devices within range (if any) that have already been granted access to main mesh network 78, or alternatively sends an instruction for the main mesh node closest to the requesting medical device to share the access key 152 with the requesting medical device 22. If no medical devices 22 are positioned within range that have already been granted access to main mesh network 78, the validation node sends the access key 152 to those devices positioned within range over provisioning mesh network 76.

The one or more medical devices 22 positioned within range of the validation node receive the validation message 150 at step 200. Each device receiving the validation message 150 forwards it to one or more additional medical devices 22 that are positioned in range. This relaying of the validation message 150 continues for as long as necessary until the validation message finally reaches the medical device 22 that originally sent the join request message 148 (the "new device"). This receipt of the validation message 150 by the original sender of message 148 is indicated in method 184 in step 202.

After step 202 (FIG. 6), in at least some embodiments, the new device proceeds immediately to step 206 and joins the main mesh network. In the embodiment illustrated in FIG. 6, however, the new device uses the access key 152 to encrypt a message and send it to medical devices 22 positioned within range over main mesh network 78. Those medical devices 22 that receive the message respond with a message that grants the new device access to main mesh network 78 at step 204. The new device receives this access-granting message at step 206 and thereafter joins main mesh network 78. Once the new device 22 has joined main mesh network 78, it sends data and messages thereafter, to the extent possible, over main mesh network 78. Such data and messages include any of the data and message mentioned previously, and may be sent for any of the purposes previously mentioned.

From the foregoing discussion of first node initialization method 172 (FIG. 5) and subsequent node initialization method 184 (FIG. 6), it can be seen that communication system 20 utilizes two mesh networks 76 and 78. The provisioning mesh network 76 is used for setting up the main mesh network 78 by transmitting join requests 148, validation messages 150, and, where appropriate, the access key 152 for joining main mesh network 78. All authorized medical devices 22 are programmed to automatically send out requests to join main mesh network 78 over provisioning network 76 after they are powered on, or at other programmed times. All medical devices 22 will therefore eventually join the main mesh network 78 and the provisioning network 76 will thereafter only be used when a new device is added to the medical devices 22 at that particular healthcare facility 80 and the new device requests to join the main mesh network 78.

In most embodiments of communication system 20 (e.g. 20, 20a, 20b, etc.), mesh networks 76 and 78 utilize the same physical layers (e.g. same frequencies, same transceivers, and same hardware), but differentiate themselves from each other by the encryption that they use. Thus, for example, mesh network 76 may be a first Bluetooth mesh network that encrypts its message contents using algorithm 140 and mesh network 78 may be a second Bluetooth mesh network that encrypts its message contents using algorithm 138. Other types of RF technology beside Bluetooth can, of course be used. Still further, in some embodiments, one or more of the mesh networks are able to use multiple different protocols. For example, in some embodiments, the medical devices 22 are configured to be able to communicate over a mesh network utilizing multiple protocols such that, for example, a medical device 22 communicates with one node the mesh network using Bluetooth, another node of the mesh network using Zigbee, and still another node using Wi-Fi, or some other protocol. In such embodiments, one or more of the medical devices 22 act as protocol translators in order to join a mesh network that comprises devices configured to use different communication protocols.

When using Bluetooth or other conventional RF technology, the encryption discussed herein and used by mesh networks 76 and 78 sits on top of the layers of the underlying RF technology that is used for carrying out the mesh communications. Thus, if Bluetooth is used, the encryption of each mesh network 76, 78 sits on top of whatever encryption Bluetooth may inherently use, as well as the underlying Bluetooth protocols, including the Bluetooth protocols used to establish a mesh. Consequently, although two devices may be able to communicate using Bluetooth mesh protocols, they cannot join provisioning mesh 76 until they are in possession of the provisioning key 144 and encryption algorithm 140 that enables them to encrypt their messages in the specific manner used by provisioning mesh network 76. Similarly, although two devices may be able to communicate using Bluetooth mesh protocols, they cannot communicate over main mesh network 78 until they are in possession of the access key 152 and the encryption algorithm 138 that enables them to encrypt their messages in the specific manner used by main mesh network 78. Indeed, in some instances, both provisioning mesh network 76 and main mesh network 78 may be the same Bluetooth mesh network as far as the underlying Bluetooth protocols are concerned.

Table 1 summarizes many of the characteristics of communication system 20 and methods 172 and 184. For example, the fact that communication system 20 uses two mesh networks 76 and 78 is indicated in the fifth column from the left of Table 1 (first row underneath the heading row). In the next column to the right, it can be seen that communication system 20 utilizes a server (94 or 96) in order to operate. Specifically, as discussed above, first node initialization method 172 utilizes the server to confirm that the first node added to main mesh network 78 is an authorized medical device 22, and subsequent node initialization method 184 utilizes the server to confirm that all of the subsequently added nodes 170 to main mesh network 78 are authorized medical devices 22.

The seventh column of Table 1 indicates whether or not all of the nodes of the main mesh network 78 need to be added manually or not, for each of the various communication system embodiments shown in Table 1. As can be seen for communication system 20, only the first node 170 used with communication system 20 is manually configured. This manual configuration process corresponds to first node initialization method 172, which has been described above and illustrated in FIG. 6. The rest of the nodes 170 are automatically added to the main mesh network 78 using provisioning mesh network 76 and the master list of authorized devices maintained on server 94 and/or 96.

The eighth column of Table 1 indicates whether the access key 152 of a communication system 20 that is used within a particular healthcare facility 80 is an access key 152 that is unique to that healthcare facility 80, or whether it is common to multiple healthcare facilities. As can be seen from the first row (under the headings), communication system 20 uses an access key 152 that is unique to each healthcare facility in which communication system 20 is installed. This was described above with respect to the unique key that is input into the first medical device 22 according to first node initialization method 172. As a result of being facility-specific, communication system 20 offers higher security against intruders because any hacker, or other unauthorized individual, who gains knowledge of the access key 152 for a particular healthcare facility 80 will not be able to use that access key 152 to break into (e.g. join) the main mesh network 78 of another healthcare facility 80.

The last column of Table 1 indicates the relative level of security for each of the different communication system embodiments 20-20f. As shown in the first row, communication system 20 offer a high level of security. This is not only because access key 152 is unique to each healthcare facility 80, as mentioned previously, but also because the sharing of access key 152 takes place over an encrypted provisioning mesh network 76, and access to provisioning mesh network 76 is restricted. That is, although many of the accompanying figures indicate that provisioning mesh network 76 is "public," it is not public in the sense that anyone with an RF-compatible mesh network-capable device can join provisioning mesh network 76. As explained previously, only devices having the provisioning key 144 and/or provisioning key encryption algorithm 140 can access provisioning mesh network 78, and both of these are maintained confidentially by the manufacturer and/or seller of medical devices 22.

As an additional layer of security, the unique key input algorithm 142 is programmed, in at least some embodiments, to vary based on time and/or information not generally known to the public and/or the technician. As a result, if the unique key used at step 176 (FIG. 5) is stolen or attempted to be used in an unauthorized manner after the technician has input it into the first device at step 176, the access key created by unique key input algorithm 142 will be different from the one previously generated. In other words, any access key 152 generated by input algorithm 142 will vary with time, the manner in which it varies with time is not public knowledge. Consequently, if a unique key is entered into a medical device 22 in a healthcare facility 80 after the initial medical device 22 of step 176 has received the unique key, the unauthorized entry of the unique key will result in the medical device 22 creating an access key 152 different from the previously created access key 152. This means that the medical device 22 will not be able to join the originally created main mesh network 78 because it will not have the access key 152 for that network 78. Any failure to secure the contents of the unique key after the main mesh network 78 has been set up will therefore not result in compromising the security of the main mesh network 78 because the unique key cannot be used twice to gain access to the same main mesh network 78.

In some embodiments, as a further layer of security, each medical device 22 is programmed such that, once it has been granted access to a main mesh network 78, it will not accept a unique key that is input into it, or it will ignore such a unique key that is input into it. As a result, once a medical device 22 has become part of main mesh network 78, it cannot be used to create an access key 152 for creating another main mesh network 78. Additionally, or alternatively, in some embodiments, each medical device 22 is programmed to only connect to and/or send data over the first main mesh network 78 that is set up, thereby restricting unauthorized personnel from creating a second main mesh network 78 to extract data from the medical devices 22.

In still other embodiments, the unique key may be selected by the manufacturer of the medical devices 22 and/or another person/entity who is not associated with the healthcare facility 80 in which the unique key will be used, and installed on one of the medical devices 22 prior to delivery to the healthcare facility 80. In this manner, there is no need for a technician to manually install the unique key via method 172, and there is little risk of the unique key being utilized by unauthorized individuals before the authorized main mesh network 78 is created.

Figure 7:
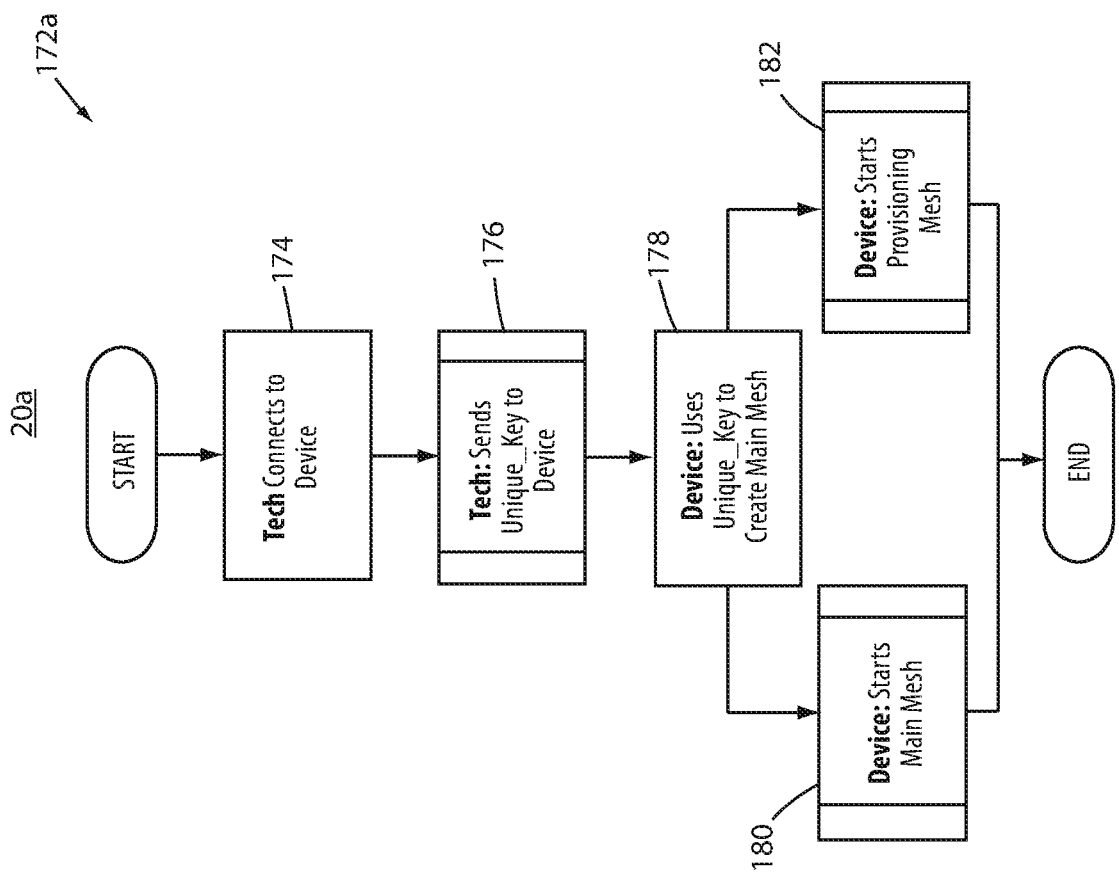
FIG. 7 is a flow diagram of a method for installing a main mesh network key on a first medical device according to a second embodiment of the communication system.
Figure 8:
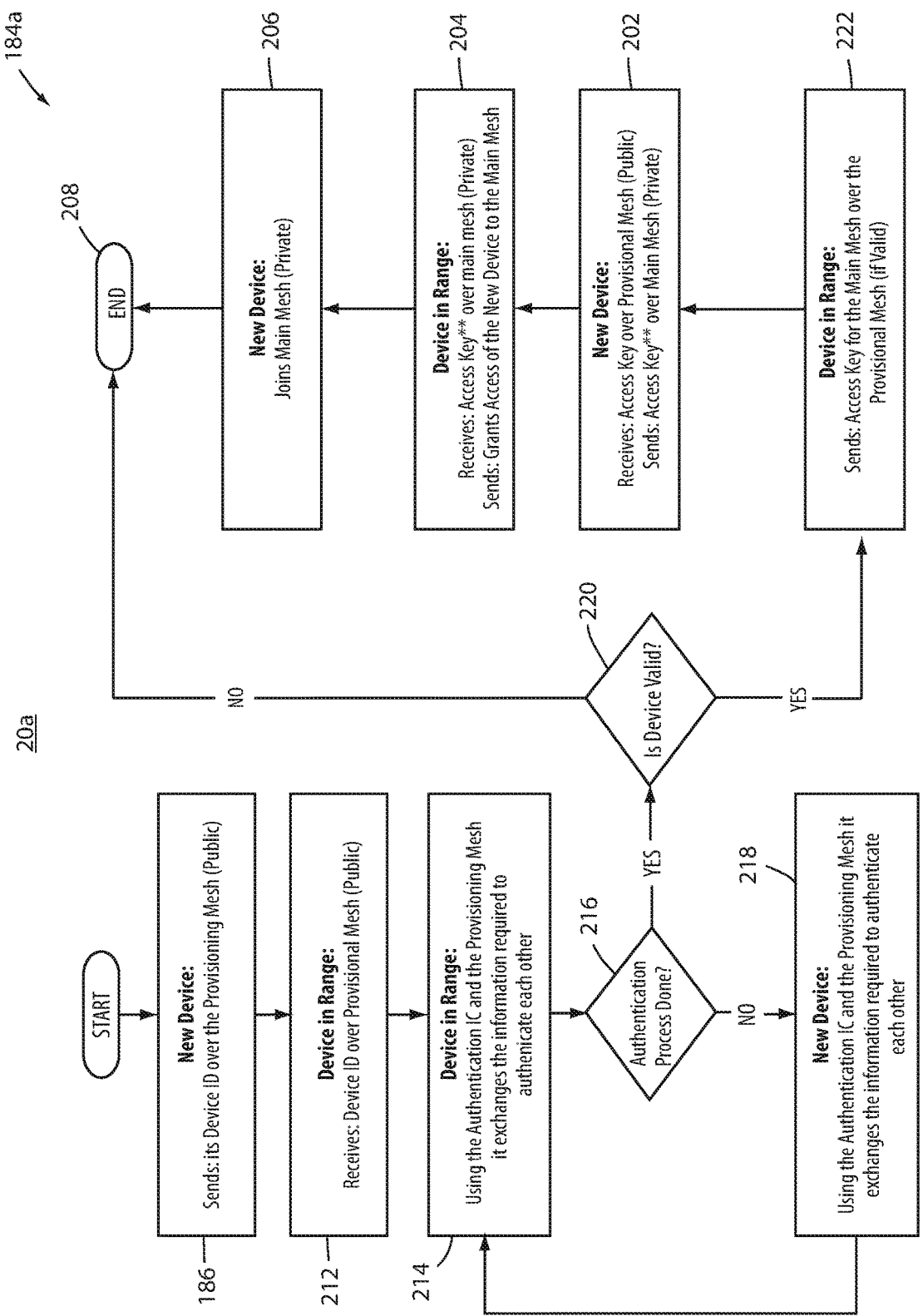
FIG. 8 is a flow diagram of a method for subsequently installing the main mesh network key of FIG. 7 on additional medical devices according to the second embodiment of the communication system.

FIGS. 7 and 8 illustrate alternative methods for setting up main mesh network 78 on an initial medical device 22 (FIG. 7) and for setting up main mesh network 78 on all of the subsequent medical devices 22 (FIG. 8). More specifically, FIG. 7 illustrates an alternative first node initialization method 172*a* and FIG. 8 illustrates an alternative subsequent node initialization method 184*a*. These methods are used in another embodiment of communication system 20; namely, communication system 20*a*. Communication system 20*a* differs from communication system 20 primarily in the manner in which medical devices 22 are determined to be authorized or not. As will be discussed in greater detail below, communication system 20*a* does not utilize a master list of authorized devices stored on server 94 or 96 (as in communication system 20), but instead relies on authenticator chips 126 (FIG. 2) built into each authorized medical device 22 in order to determine whether or not a medical device 22 is authorized or not.

Methods 172*a* and 184*a* of communication system 20*a* utilize a number of steps that are common to methods 172 and 184, respectively, of communication system 20. Those common steps have been assigned the same reference number. Steps which are different have been assigned a new reference number.

As can be seen from FIG. 7, first node initialization method 172*a* of communication system 20*a* is the same as first node initialization method 172 of communication system 20. That is, it includes all of the same steps 174, 176, 178, 180, and 182 previously described for method 172. Accordingly, the previous description of these steps with respect to method 172 is applicable here and method 172*a* does not need to be described any further.

After the first node of main mesh network 78 of communication system 20*a* has been set up in accordance with method 172*a*, subsequent nodes 170 are automatically added to main mesh network in accordance with subsequent node initialization method 184*a* (FIG. 8). Subsequent node initialization method 184*a* begins at step 186, which is the same as step 186 of method 184. At step 186, a new medical device 22 (e.g. a medical device 22 not yet part of main mesh network 78) sends out a join request message 148 over provisioning mesh network 76. The join request message 148 includes the device ID 136 of the new medical device 22. At step 212, a medical device 22 within range of the new medical device 22 receives the join request message 148.

In response to the join request message 148, the medical device 22 within range initiates a set of authentication communications with the new medical device 22 at steps 214, 216, and 218. The authentication communications are generated by authenticator chip 126 on board the medical device 22 within range and transmitted to the new medical device. The new medical device 22 forwards the communications to its own authenticator chip 126 which determines the appropriate response(s). The new medical device 22 then sends one or responses to the medical device 22 positioned within range based on the instructions from its authenticator chip 126. The new medical device 22 and medical device 22 positioned within range continue to send authentication messages back and forth using their respective authentication chips 126 until the medical device 22 positioned within range concludes that the new medical device 22 is an authorized medical device 22, or until the medical device 22 positioned within range concludes that the new medical device 22 is not an authorized medical device 22. The medical device 22 positioned within range makes this conclusion at step 220. If the medical device 22 positioned within range decides the new medical device 22 is not an authorized medical device, it proceeds to step 208 where method 184*a* terminates. If the medical device 22 positioned within range decides the new medical device 22 is an authorized medical device 22, it proceeds to step 222, as will be discussed more below.

The authentication messages sent back and forth between the new medical device 22 and the medical device 22 positioned within range during steps 214-218 may take on the form of a series of challenge questions that require specific responses. The questions and responses, in some embodiments, vary in such a manner that each time a medical device 22 is subjected to the authentication process, different challenges and/or answers are required, thereby preventing another unauthorized device that is sniffing the questions and answers from simply repeating those questions and/or answers in order to gain unauthorized access to main mesh network 78. Authenticator chips 126 may be conventional, commercially available authentication chips. One example of such a chip is an Atmel AT88SA102S CryptoAuthentication Product Authentication Chip available from Atmel Corporation of San Jose, Calif. A wide variety of other types of authenticator chips may be used.

After the medical device 22 positioned within range of the new medical device 22 determines at step 220 that the new medical device 22 is an authorized medical device 22, it proceeds to step 222 (FIG. 8) where it sends the access key 152 to the new medical device 22. The access key 152 is received at step 202, which is the same step 202 of method 184 of FIG. 6. Indeed, steps 202, 204, and 206 of method 184*a* are the same as steps 202, 204, and 206 of method 184 and need not be described again. In general, once a medical device 22 has been authenticated, it is sent the access key 152 and added to the main mesh network 78 via steps 222, 202, 204, and 206.

Table 1 provides a general summary of some of the aspects of communication system 20*a*, including first and subsequent node initialization methods 172*a* and 184*a*. As shown in the fifth column from the left, communication system 20*a* uses two mesh networks 76 and 78. The provisioning mesh network 76 is used to send join request messages 148 and authentication messages generated by authenticator chips 126. It is also used to distribute access key 152 to medical devices 22 after they have been authenticated.

As can be seen from the sixth column from the right in Table 1, communication system 20*a* does not rely upon, or otherwise utilize, server 94 or 96. This is because communication system 20*a* uses authenticator chips 126 to determine whether a medical device 22 is an authorized medical device 22 or not, rather than using a master list maintained on server 94 or 96, as communication system 20 does.

The seventh and eighth columns of Table 1 indicate that communication system 20*a* does not require all of the nodes 170 to be manually configured (seventh column), but instead only requires the first node of main mesh network 78 to be manually configured (eighth column). This manual configuration of the first node is carried out in accordance with method 172*a*.

The ninth column of Table 1 indicates that the encryption used by main mesh network 78 is specific to the particular healthcare facility 80 in which the main mesh network 78 is installed. This facility-specific encryption is created through the use of a facility-specific input key during first node initialization method 172a. The tenth column of Table 1 indicates that communication system 20a creates a relatively high level of security, just as with communication system 20. The high level of security comes from the encryption of both provisioning mesh network 76 and main mesh network 78, as well as the use of authenticator chips 126.

Figure 9:
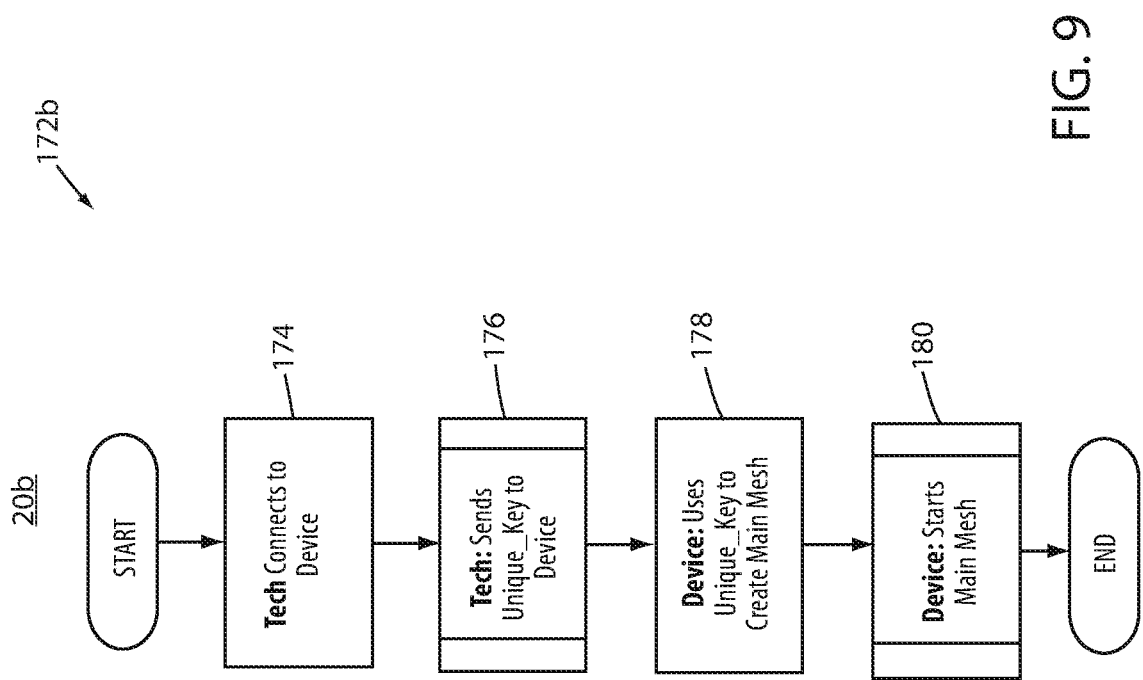
FIG. 9 is a flow diagram of a method for installing a main mesh network key on a first medical device according to a third embodiment of the communication system.
Figure 10:
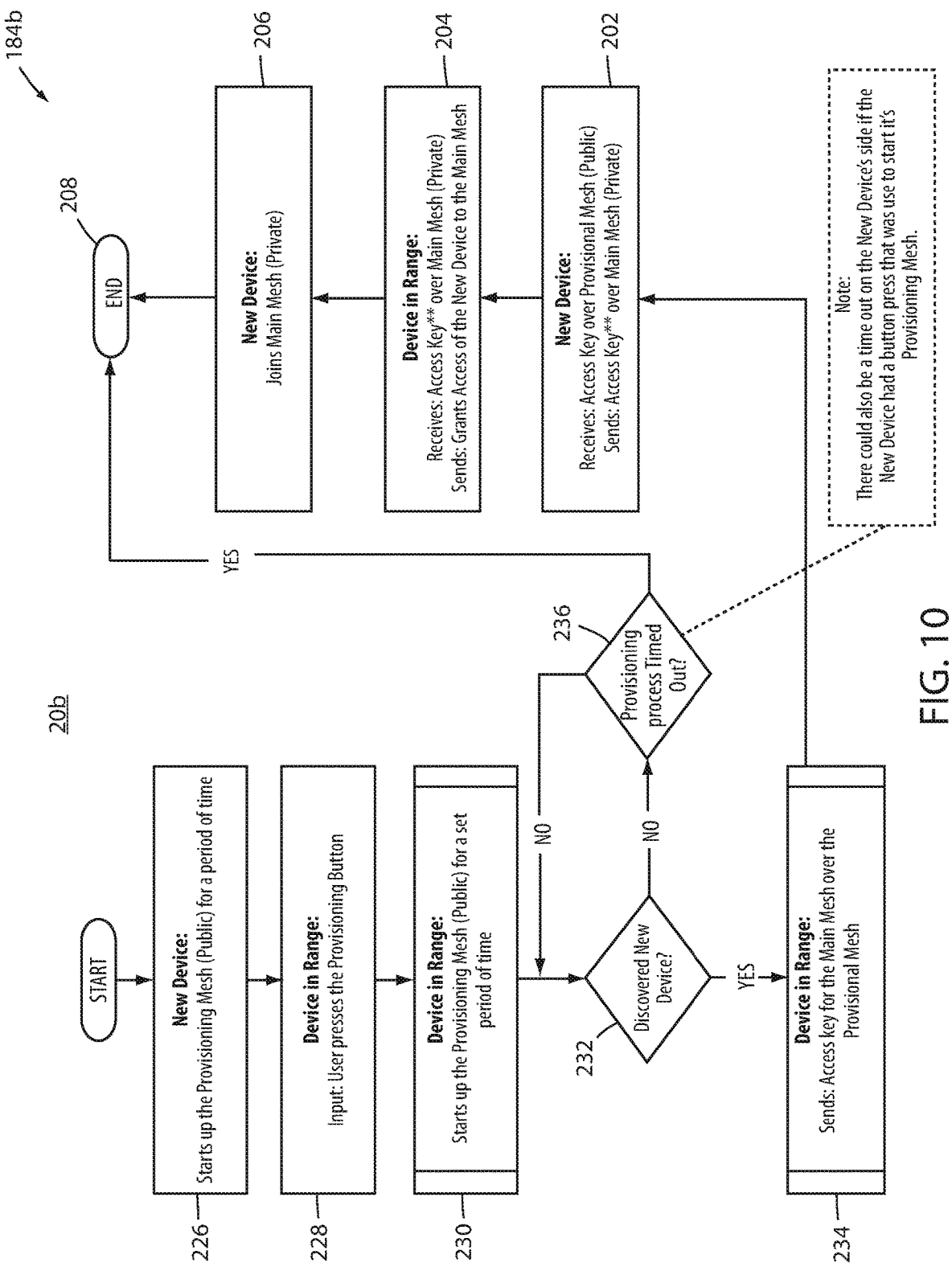
FIG. 10 is a flow diagram of a method for subsequently installing the main mesh network key of FIG. 9 on additional medical devices according to the third embodiment of the communication system.

FIGS. 9 and 10 illustrate alternative methods for setting up main mesh network 78 on an initial medical device 22 (FIG. 9) and for setting up main mesh network 78 on all of the subsequent medical devices 22 (FIG. 10). More specifically, FIG. 9 illustrates a second alternative first node initialization method 172b and FIG. 10 illustrates a second alternative subsequent node initialization method 184b. These methods are used in another embodiment of communication system 20; namely, communication system 20b. Communication system 20b differs from communication systems 20 and 20a primarily in the manner in which medical devices 22 are determined to be authorized or not. As will be discussed in greater detail below, communication system 20b does not utilize either a master list of authorized devices stored on server 94 or 96 (as in communication system 20) nor does it utilize any authenticator chips (as in communication system 20a). Instead, communication system 20 utilizes the manual pressing of a button (or other user manipulation of one or more controls physically mounted on the medical devices 22) as an indication that the medical device 22 is an authorized medical device. This is discussed in greater detail below.

Methods 172b and 184b of communication system 20b utilize a number of steps that are common to methods 172 and 184, respectively, of communication system 20. Those common steps have been assigned the same reference number. Steps which are different have been assigned a new reference number.

First node initialization method 172b (FIG. 9) is the same as first node initialization method 172 (and 172a) with one exception: it omits step 182. That is, it omits starting provisioning network 76. Thus, method 172b includes steps 174, 176, 178, and 180, which have all been described previously. The result of these steps is the creation of a main mesh network 78 having an access key 152 that is unique to the particular healthcare facility 80 in which the initial medical device 22 of method 172b is installed. The starting of provisioning mesh network 76, however, does not start until subsequent node initialization method 184b starts, which will now be described.

Subsequent node initialization method 184b begins at step 226 when a new medical device 22 is to be added to main mesh network 78 (FIG. 10). Specifically, the new medical device 22 starts up provisioning mesh network 76 for a period of time at step 226. This start up of provisioning mesh network 76 may occur in a variety of different ways. In some embodiments, the startup of provisioning mesh network 76 occurs when a user inserts a dongle into a compatible port on the medical device 22, such as a USB dongle into a USB port. The dongle is coupled to a program or other data that, when read by medical device 22, causes the controller 104, 120 of the medical device 22 to start provisioning mesh network 76. In other embodiments, the user connects to the medical device 22 using a laptop, smart phone, or other portable electronic device, and the laptop, smart phone, or other portable electronic device includes the aforementioned program or other data. In still other embodiments, the user starts up the provisioning mesh network by pressing a button or a series of buttons on the medical device 22, or otherwise activating one or more controls on the medical device 22.

Regardless of how step 226 (FIG. 10) is specifically carried out by the new medical device 22, the new medical device 22 begins provisioning mesh network 76 at step 226. The starting of provisioning mesh network 76 includes, in some embodiments, the periodic transmission of messages over provisioning mesh network 76 announcing the presence of the new medical device 22. At step 228, a medical device 22 positioned within range of the new medical device 22 is prompted by a user to also start up provisioning mesh network 76. This medical device 22 is a medical device 22 that is already part of main mesh network 78. In at least one embodiment, the prompting involves pressing (or otherwise activating) the join button 124 of the medical device 22 positioned within range. In other embodiments, this may involve any technique similar to those mentioned above with respect to step 226 (e.g. inserting a dongle into the device 22, connecting a laptop, phone, etc. to the device . . . ).

Regardless of the specific technique used in step 228 to start provisioning mesh network 76 by the medical device 22 positioned in range, that medical device 22 begins provisioning mesh network 76 for a set period of time at step 230. This may involve transmitting a message using the provisioning mesh network encryption algorithm that announces the presence of the medical device 22 positioned within range. This occurs for a minimum period of time. After both the new medical device 22 and the nearby medical device 22 have started communicating using provisioning mesh network 76, they will receive each other's messages (unless they are out of range, or some sort of malfunction occurs). After receiving each other's messages, the two medical devices 22 discover each other at step 232 and the medical device within range sends the new medical device 22 the access key 152 at step 234.

If the medical devices 22 do not discover each other within a specified time period after starting their respective provisioning mesh network 76, the medical device 22 stops transmitting over provisioning mesh network 76 and terminates initialization method 184 without adding the new device 22 to the main mesh network 78. This is indicated in FIG. 10 by step 236. If either medical device 22 has not discovered the other by the specific time period, which is checked at step 236, method 184 terminates (step 208). On the other hand, if the medical devices 22 do discover each other, the medical device 22 positioned within range sends the access key 152 to the new medical device at step 234. From step 234, method 184b proceeds to steps 202, 204, and 206, which are the same as steps 202, 204, 206 in methods 184 and 184a, and therefore do not need to be described again. The result of steps 202, 204, and 206 is that the new medical device has joined main mesh network 78.

Table 1 provides a general summary of some of the aspects of communication system 20b, including first and subsequent node initialization methods 172b and 184b. As shown in the fifth column from the left, communication system 20b uses two mesh networks 76 and 78. Provisioning mesh network 76 is used to share access key 152, as in the previous communication systems 20 and 20b. However, unlike with communication systems 20 and 20a, the provisioning mesh network 76 of communication system 20b is set up only intermittently and controlled manually by a user. By limiting the times at which provisioning mesh network 76 is set up, unauthorized individuals are likewise limited to in their efforts to hack into provisioning mesh network 76. Further, by limiting the times to relatively short periods (e.g. ten to fifteen seconds, although other time periods can be used), the window for unauthorized entry into provisioning mesh network 76 is further closed.

As can be seen from the sixth column from the right in Table 1, communication system 20b does not rely upon, or otherwise utilize, server 94 or 96. This is because communication system 20b uses the manual activation of join button 124, and/or the manual starting of provisioning mesh network 76 on a new device 22, as a proxy for authentication. That is, communication system 20b relies upon authorized users manually adding only authorized medical devices 22 to the main mesh network 78. Further, it relies upon relatively short time windows for allowing authorized users to add a medical device 22 to the main mesh network 78 to further protect against unauthorized usage.

Table 1 also indicates in the seventh and eighth columns that all nodes 170 (e.g. authorized medical devices 22) of main mesh network 78 have to be installed manually. In the ninth column, Table 1 shows that main mesh network 78 uses encryption that is specific to the healthcare facility 80 in which it is installed. Finally, the tenth and last column of Table 1 indicates that communication system 20b provides a medium level of security. One or more steps may be added in certain embodiments in order to improve this security, including, but not limited to, obscuring join button 124 such that it is not apparent to unauthorized user how to utilize join button 124. This may include, among other aspects, not labeling join button 124, implementing join button 124 as a predetermined sequence of button presses (or other actions besides "pressing"), using a dongle whose possession is restricted, using a program on a portable electronic device whose distribution is limited to only authorized individuals, and/or programming medical devices 22 to only join a main mesh network 78 once and to ignore further presses of the join button after the medical device 22 has joined a main mesh network 78. Still other steps may be taken to enhance the security of communication system 20b.

Figures 11, 12:
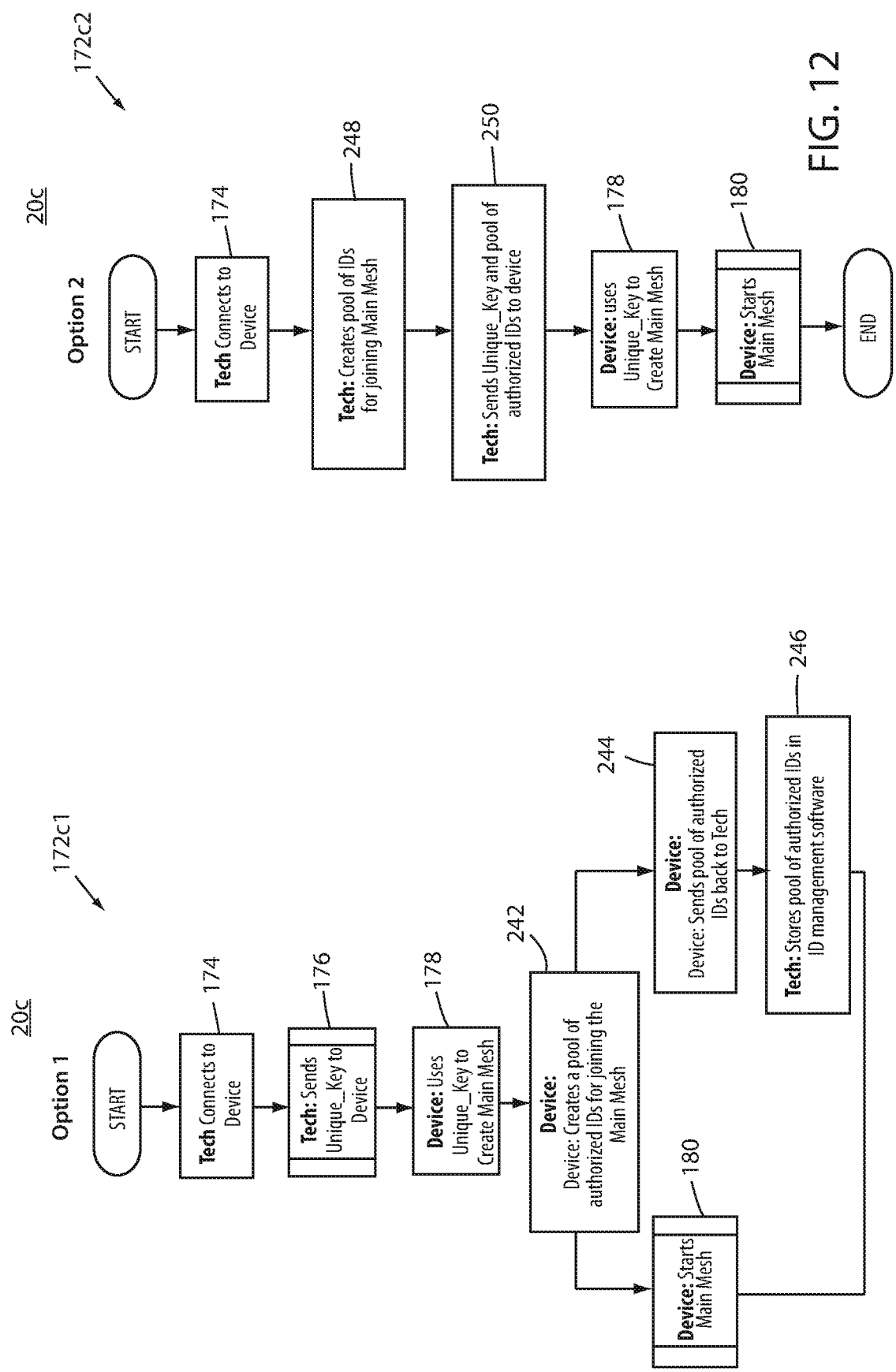
FIG. 11 is a flow diagram of a method for installing a main mesh network key on a first medical device according to a fourth embodiment of the communication system.
FIG. 12 is a flow diagram of an alternative method for installing a main mesh network key on first medical device according to the fourth embodiment of the communication system.
Figure 13:
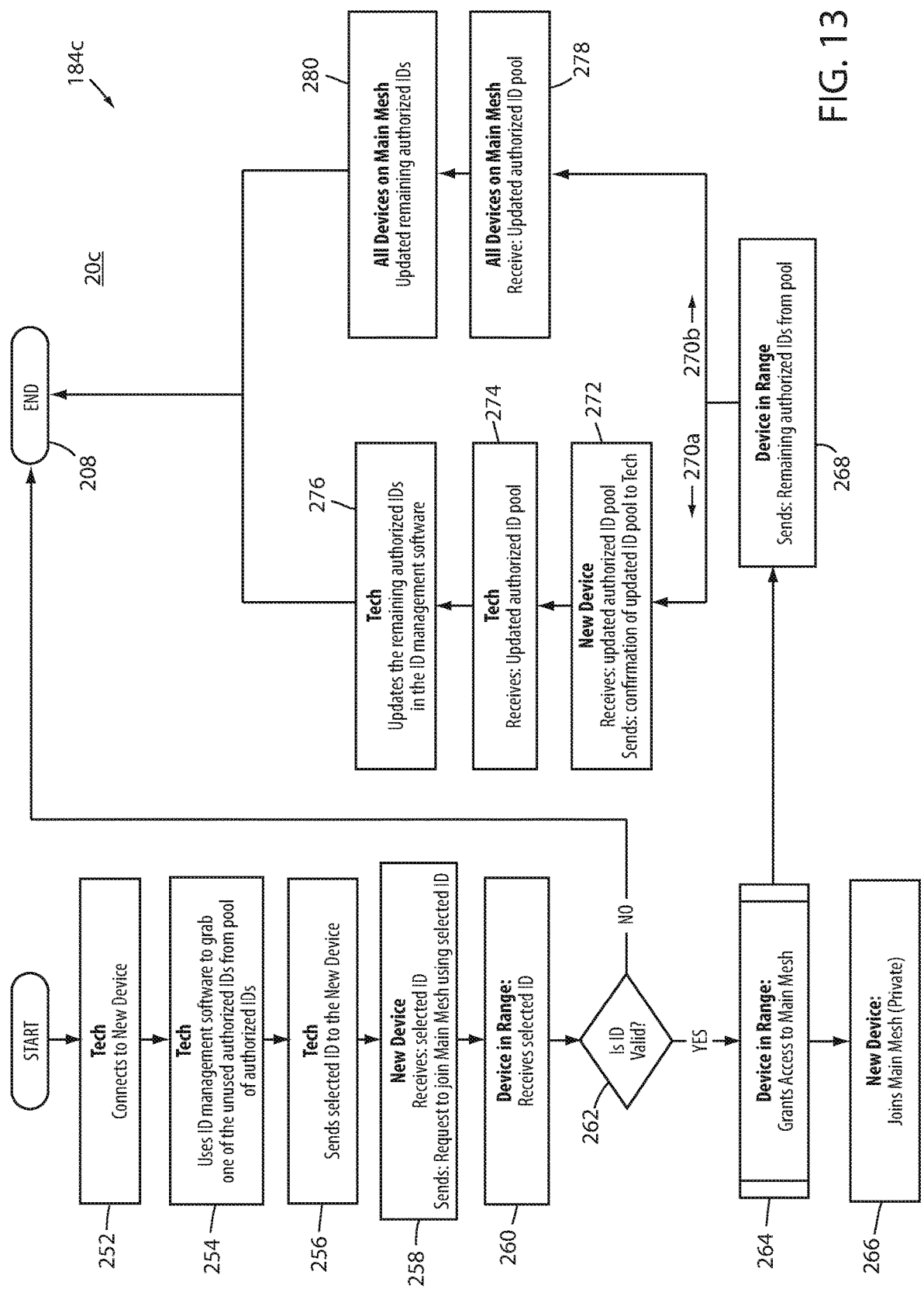
FIG. 13 is a flow diagram of a method for subsequently installing the main mesh network key of FIGS. 11 and 12 on additional medical devices according to the fourth embodiment of the communication system.

FIGS. 11-13 illustrate yet another alternative set of methods for setting up main mesh network 78 on an initial medical device 22 (FIGS. 11-12) and for setting up main mesh network 78 on all of the subsequent medical devices 22 (FIG. 12). More specifically, FIG. 11 illustrates a first option for a third alternative first node initialization method 172c1; FIG. 12 illustrates a second option for a third alternative first node initialization method 172c2; and FIG. 13 illustrates a third alternative subsequent node initialization method 184b. These methods are used in communication system 20c. Communication system 20c differs from communication systems 20, 20a, and 20b in several respects. First, communication system 20c includes no provisioning mesh network 76, and instead only includes a single mesh network: main mesh network 78. Second, communication system 20c determines which medical devices 22 are authorized or not based upon a pool of authorized access keys. And third, communication system 20c, unlike communication systems 20 and 20a (but similar to communication system 20b) relies upon the manual integration of all nodes 170 into main mesh network 78. These differences and similarities are discussed in greater detail below.

Communication system 20c, as with communication systems 20, 20a, and 20b, utilizes two methods for initializing nodes: a first node initialization method for initializing the first node of main mesh network 78 and a subsequent node initialization method for initializing all of the nodes after the first node of main mesh network 78 has been initialized. Communication system 20c utilizes one of two different methods for its first node initialization method: a first method 172c1 that is illustrated in FIG. 11 and a second method 172c2 that is illustrated in FIG. 12. Variations to either of these methods, as well as combinations of one or more of these steps, may be implemented.

Methods 172c1 and 172c2 of communication system 20c utilize a number of steps that are common to first node initialization methods 172, 172a, and/or 172b. Those common steps have been assigned the same reference number. Steps which are different have been assigned a new reference number.

First node initialization method 172c1 (FIG. 11) begins at step 174 when a technician connects to whichever medical device 22 he or she wishes to be the first device 22 in the main mesh network 78. As noted, the choice of this first medical device 22 is up to the technician. Step 174 of method 172c1 is the same as step 174 in the previously described first node initialization methods 172, 172a, and 172b. After step 174, the technician proceeds to send a unique key to the selected medical device 22 at step 176. Step 176 of method 172c1 is also the same as step 176 in methods 172, 172a, and 172b. After sending a unique key to the selected medical device 22 at step 176, the medical device 22 is programmed to use the unique key to create an access key 152 and set up main mesh network 78. This is done at step 178, which has been previously described with respect to methods 172, 172a, and 172b.

The medical device 22 to which the technician connects during method 172c1 (FIG. 11) is programmed to include an authorized ID pool generation algorithm. Although not shown in FIG. 3, this authorized ID pool generation algorithm is stored in memory 108 and/or 122. The authorized ID pool generation algorithm may use the input key that was input at step 176 to create a set, or pool, of authorized IDs, or it may use random number generating techniques to generate the pool of authorized IDs, or it may use a combination of both. The ID generation techniques may be conventional and the authorized IDs may be strings of alphanumeric characters of a specified length. Each authorized ID serves a similar purpose to the device IDs 136 used in communication system 20, but the authorized IDs are created by the ID pool generation algorithm, rather than by medical device manufacturer. Further, the authorized IDs are independent of the device IDs 136 such that an authorized medical device 22 may include both a device ID 136 and an authorized ID, or it may include only an authorized ID.

After creating the set of authorized IDs at step 242 (FIG. 11), the medical device 22 is programmed to start the main mesh network at step 180. Step 180 of method 172c1 is the same as step 180 in the previously described methods 172, 172a, and 172b. The medical device 22 is also programmed to send the pool of authorized IDs created during step 242 to the technician at step 244. This is done using the same communication channel that the technician uses to connect to the medical device 22 at step 174. The medical device 22 also saves the pool of authorized IDs locally in its memory 108 (or 122) for purposes described more below with respect to subsequent node initialization method 184c.

The information sent by the medical device 22 to the technician includes not only the entire pool of authorized IDs created at step 242, but also an identification of the one of those authorized IDs that the medical device 22 has assigned to itself for use with main mesh network 78. In other words, in addition to creating the pool of authorized IDs, the medical device 22 is also programmed to select one of the created IDs and assign it to itself. The particular ID that the medical device 22 selects and assigns to itself is identified to the technician (and/or his or her laptop, or other electronic device) so that the technician (and/or his or her laptop, or other electronic device) knows not to assign that particular ID to another medical device 22. The medical device 22 also stores in its memory the ID it has assigned itself so that, as will be explained later, it will not recognize or allow another medical device 22 to join main mesh network 78 that is attempting to use that same ID.

At step 246 (FIG. 11), the authorized IDs generated by the first medical device 22 and sent to the technician (and/or his or her laptop, or other electronic device) are stored in the memory of an electronic device having authorized ID management software installed thereon. The authorized ID management software maintains a list of all of the authorized IDs that were generated at step 242 of method 172c1, and also keeps track of which ones of those authorized IDs have been assigned and which ones have not been assigned. The software also keeps track of which devices have been assigned which authorized IDs. As will be discussed more below, the technician uses this software to manually add new medical devices 22 to the main mesh network 78 using subsequent node initialization method 184c, which will be discussed in more detail below with respect to FIG. 13.

Before turning to FIG. 13, however, communication system 20c may alternatively utilize a first node initialization method that is different from the one illustrated in FIG. 11, such as the alternative first node initialization method 172c2 illustrated in FIG. 12. Alternative first node initialization method 172c2 starts at step 174 with the technician connecting to a selected medical device 22 that will be the first one to create main mesh network 78. After connecting to the medical device at step 174, the technician utilizes authorized ID management software maintained on his or her laptop, cell phone, or other electronic device to create a pool of authorized IDs at step 248. This creation of a pool of authorized IDs takes place in the same manner as described above except that, rather than the medical device 22 creating the pool of authorized IDs, the authorized ID pool management software used by the technician creates the IDs. Thus, the laptop, cell phone, or other electronic device used by the technician has the authorized ID pool generation algorithm stored on it, rather than the medical device 22.

After creating the pool of authorized IDs at step 248 (FIG. 12), the authorized ID pool management software sends the pool of authorized IDs to the medical device 22 at step 250. At step 250, the authorized ID pool management software also assigns one of the authorized IDs from the pool to the medical device 22 and shares this assignment with the medical device 22. At step 250, the technician also sends the unique key to the device in the same manner previously described with respect to step 176. After receiving the pool of authorized IDs, its assigned authorized ID, and the unique key at step 250, the medical device proceeds to step 178 where it uses the unique key to create an access key 152 and set up main mesh network 78, as has been described previously. The medical device 22 then proceeds to step 180, which has also been previously described, and sets up main mesh network 78.

As will be apparent from a comparison of FIGS. 11 and 12, the difference between methods 172c1 and 172c2 is that location of the authorized ID pool generation algorithm. In the first method 172c1, the authorized ID pool generation algorithm is maintained on the medical device 22. In the second method 172c2, the authorized ID pool generation algorithm is maintained on the technician's computer (e.g. laptop, cell phone, desktop, etc.) and is combined with the authorized ID pool management software maintained thereon. It will also be apparent from a study FIG. 11 that the only difference between the medical devices 22 of method 172c1 and those previously described is that the medical devices 22 of method 172c1 include the authorized ID pool generation algorithm stored in their memories 108 or 122 (or at least one of the medical devices 22 of method 172c1 includes this algorithm—it is not necessary for every medical device 22 of method 172c1 to include this algorithm in its memory, only the one connected to during step 174 of method 172c1). From a study of FIG. 12, it can be seen that the medical devices 22 of method 172c2 may be the same as the medical devices 22 previously described with respect to communication systems 20, 20a, and/or 20b.

After the initial node of main mesh network 78 has been set up in communication system 20c (using either method 172c1 or method 172c2), the rest of the main mesh network 78 is set up using subsequent node initialization method 184c, which is illustrated in FIG. 13. Subsequent node initialization method 184c starts at step 252 when a technician connects to a medical device 22 that is not yet part of main mesh network 78 (referred to as the "new device" in FIG. 13), but which the technician wants to add to main mesh network 78. This connection takes place in any of the same manners that the technician connects to the initial medical device 22 of main mesh network 78, and such manners have been previously described with respect to step 174 and need not repeated.

After connecting to the medical device 22 to be added to main mesh network 78 at step 252 (FIG. 13), method 184c proceeds to step 254 where the technician uses the authorized ID management software maintained on his or her computer (e.g. laptop, cell phone, desk top, etc.) to select one of the unused authorized IDs from the pool of authorized IDs. The manner used to select the ID may be random, sequential, or any other conventional technique provided that the technique only selects from those authorized IDs that have not yet been assigned to a medical device 22. After selecting one of the unused authorized IDs, the technician (or the authorized ID management software) sends the selected authorized ID to the medical device 22 at step 256. In some embodiments, the technician also sends at step 256 the access key 152 created the initial medical device 22 at step 178 to the new medical device 22.

At step 258 (FIG. 13), the medical device 22 receives the selected ID and sends out a request to join the main mesh network 78. In those embodiments where the new medical device 22 also receives the access key 152 at step 256, the new medical device 22 uses the access key 152 to encrypt the request to join the main mesh network it sends out at step 258. In those embodiments where the access key 152 is not sent to the new medical device 22 at step 256, the request to join the main mesh network sent out at step 258 may utilize encryption that all authorized medical devices 22 are preprogrammed to understand, such as, but not limited to, the type of encryption used with provisioning mesh network 76 of communication system 20.

Regardless of the encryption used to send the request to join main mesh network 78 at step 258, the request is sent out to any medical devices 22 that are within range and that are already part of main mesh network 78. If there is such a medical device 22 within range (referred to in FIG. 13 as "device in range"), the medical device 22 receives the request at step 260. The request includes the authorized ID assigned to the medical device 22 that sent the request. At step 262, the device receiving the request determines if the authorized ID contained within the request is valid or not. The determination of whether or not it is valid is done by comparing the received authorized ID to the list of authorized IDs that is maintained on the medical device 22. That is, each medical device 22 that has been granted access to main mesh network 78 in communication system 20*c* maintains the list of authorized device IDs that was generated at either step 242 (method 172*c*1) or step 248 (method 172*c*2). At step 262, the medical device compares the received authorized ID to this list and determines two items: (1) is the received authorized ID (received at step 260) on the list, and (2) if so, has it been assigned already to a medical device 22 that is already part of main mesh network 78? If the answer to the first question is yes and the answer to the second question is no, then the medical device 22 concludes at step 262 that the authorized ID is valid and that the medical device 22 is authorized to join main mesh network 78. Method 184*c* then proceeds to step 264.

If the medical device 22 ("device in range") determines at step 262 (FIG. 13) that the received ID is not on the list of authorized IDs it maintains, or the medical device 22 determines that the received ID has already been assigned to a medical device 22 that is part of main mesh network 78, the medical device 22 concludes at step 262 that the received ID is not valid. In such a case, the medical device 22 does not grant the new medical device 22 access to the main mesh network, but instead proceeds to step 208 where method 184*c* terminates.

If the medical device 22 ("device in range") determines at step 262 (FIG. 13) that the received ID is valid, it proceeds to grant the new medical device 22 access to main mesh network 78. In those embodiments of communication system 20*c* wherein the new device 22 has not already received an access key 152 from the technician (such as at step 256), the granting of access to main mesh network 78 at step 264 includes sending the access key 152 to the new medical device 22. In those embodiments of communication system 20*c* wherein the new medical device 22 has already received the access key 152 from the technician, the granting of access to main mesh network 78 at step 264 may involve sending one or more confirmation messages, sending a new key used by all authorized medical devices 22 to communicate over main mesh network 78, a combination of these, and/or other actions. Regardless of the specific actions undertaken with step 264, the new medical device 22 then joins the main mesh network 78 at step 266.

After granting access to main mesh network 78 at step 264, the "device in range" medical device 22 (FIG. 13) also proceeds to update the list of authorized and available IDs maintained both by the technician's authorized ID management software and by the other medical devices 22 that are already part of main mesh network 78 (if any). This process starts at step 268 where the "device in range" medical device 22 sends out an updated list of available IDs to all medical devices 22 that are already part of main mesh network 78. This updated list is updated to indicate that the particular ID received at step 260 has now been assigned to the "new device." The other medical devices 22 that are part of main mesh network 78 use this updated list to determine whether or not future medical devices 22 attempting to join main mesh network 78 are valid or not. In other words, the other medical devices 22 use this updated list if they are ever tasked with performing step 262 at a future time and/or when they are tasked with determining whether a message has been sent by an authorized medical device 22 of main mesh network 78.

The transmission of the updated list of available IDs includes sending the list to both the "new device" that just joined the main mesh network at step 266, as well as to all of the medical devices 22 that were previously part of main mesh network 78. These two tasks are shown by the divided branches 270*a* and 270*b* in FIG. 13. Branch 270*a* relates to the steps undertaken to update the new medical device 22 and the technician, while branch 270*b* relates to the steps undertaken to update the medical devices 22 that were previously part of main mesh network 78.

Turning first to branch 270*a* (FIG. 13), the "new device" receives at step 272 the updated list of assigned (and unassigned) authorized IDs. The new medical device 22 also sends out a confirmation message to the technician at step 272 that includes the updated list of authorized IDs. The technician receives this updated list at step 274. Then, either the technician manually updates the authorized list of IDs at step 276 or the ID management software automatically updates the authorized list of IDs at step 276. Branch 270*a* of method 184*c* then ends.

Turning to branch 270*b* (FIG. 13), the other medical devices 22 that are already part of main mesh network 78 (referred to as "all devices on main mesh network" in FIG. 13) receive the updated list of assigned (and unassigned) authorized IDs at step 278. Once a medical device 22 that is already part of main mesh network 78 receives the updated list, it proceeds at step 280 to update its own internally stored list of assigned and unassigned authorized IDs. After all of the medical devices 22 that are already part of main mesh network 78 complete this internal update, branch 270*b* terminates and method 184*c* comes to an end at step 208. It will be appreciated that steps 278 and 280 may, in some cases, involve relaying the updated list through multiple medical devices 22 before all medical devices 22 that are part of main mesh network 78 receive the updated list. This will happen in those cases where main mesh network 78 includes one or more nodes 170 that are not within range of the medical device 22 that initially transmits the updated list at step 268. In such cases, the medical device 22 (or medical devices 22) that receive the updated list at step 278 will relay the updated list to one or more additional medical devices 22 at step 278 that may be beyond the range of the medical device 22 that sent the updated list at step 268.

From the foregoing description of methods 172*c*1, 172*c*3, and 184*c*, it will be appreciated that communication system 20*c* maintains a master list (pool) of identifiers (IDs) that identify medical devices 22 that are authorized to join main mesh network 78. Communication system 20*c* maintains this list both on a technician's computer and within each medical devices 22 that is already part of main mesh network 78. As new medical devices 22 join the main mesh network, the master list is updated to reflect the assignment of IDs to the new medical devices 22. The updated master list is used to decide whether to grant access to the main mesh network 78. Thus, communication system 20*c* limits access to main mesh network to only those medical devices 22 that are in possession of an authorized ID, and such authorized IDs are manually shared with new medical devices via a technician connecting to the medical device 22. Additional security may also be built into the medical devices 22, such as the use of access keys 152 in one or more of the manners previously described above with respect to communication system 20.

Communication system 20*c* is, in some respects, similar to a modified form of communication system 20 in which, instead of maintaining a master list of authorized device IDs 136 on a server (94 or 96), a master list of authorized IDs are maintained on a technician's computer and in each medical device 22 that is already part of main mesh network 78. The master list is updated as new medical devices 22 are added to main mesh network 78.

As with the other communication systems disclosed herein, Table 1 summarizes several of the characteristics of communication system 20c and methods 172c1, 172c2, and 184c. For example, the fact that communication system 20c uses only a single mesh network 78 (rather than two mesh networks) is indicated in the fifth column from the left of Table 1 (fourth row underneath the heading row). In the next column to the right, it can be seen that communication system 20c does not utilizes a server (e.g. 94 or 96) in order to operate. Specifically, as discussed above, methods 172c1, 172c2, and 184c utilize a pool of authorized IDs that are maintained on the medical device 22 themselves, as well as on the computer used by a technician, rather than on a dedicated server. It will be understood, however, that in some embodiments, the technician's computer may be a computer coupled to LAN 82 that connects to medical devices 22. In such embodiments, communication system 20c utilizes a server, but not for the same purposes as server 94 of 96 of communication system 20.

The seventh column of Table 1 indicates whether or not all of the nodes of the main mesh network 78 need to be added manually or not, and the eighth column indicates whether the initial node of main mesh network 78 needs to be manually added or not. As can be seen for communication system 20c, all of the nodes 170 need to be manually configured (including the initial node) by having a technician connect to each medical device 22 in order for it to gain access to main mesh network 78.

The ninth column of Table 1 indicates that the encryption used with communication system 20c, which utilizes access keys 152, is unique to the particular healthcare facility 80. The uniqueness stems from the use of a unique key that is input into the medical device 22 to generate a unique access key 152 using unique key input algorithm 142.

Finally, the tenth column indicates that the level of security of communication system 20c is medium relative to the other communication system embodiments discussed herein. From the foregoing description, it can be seen that unauthorized medical devices 22 are prevented from joining main mesh network 78 because such unauthorized medical devices 22 do not possess an unassigned authorized ID that appears on the master list, or pool, of authorized medical devices 22. Further, if an unauthorized medical device 22 gains access to an already assigned authorized ID, such as by sniffing and decrypting the communications of an authorized device 22 that is part of main mesh network 78 (including the access key 152), the unauthorized will still not be able to join main mesh network 78 using the sniffed authorized ID of the already authorized medical device 22 because that authorized ID has been assigned. In some instances, the storage of the master pool of authorized IDs includes storing a unique identifier of the authorized medical device 22 for all of the IDs that have already been assigned. For example, the master list of authorized IDs may include the MAC addresses of all the medical devices 22 that have been assigned an authorized ID, along with a correlation of which ID goes with which MAC address, thereby preventing another medical device with another MAC address from using the assigned authorized ID. Still other security measures may be utilized, including additional layers of encryption and/or additional keys beyond the ones described herein.

Figures 14, 15:
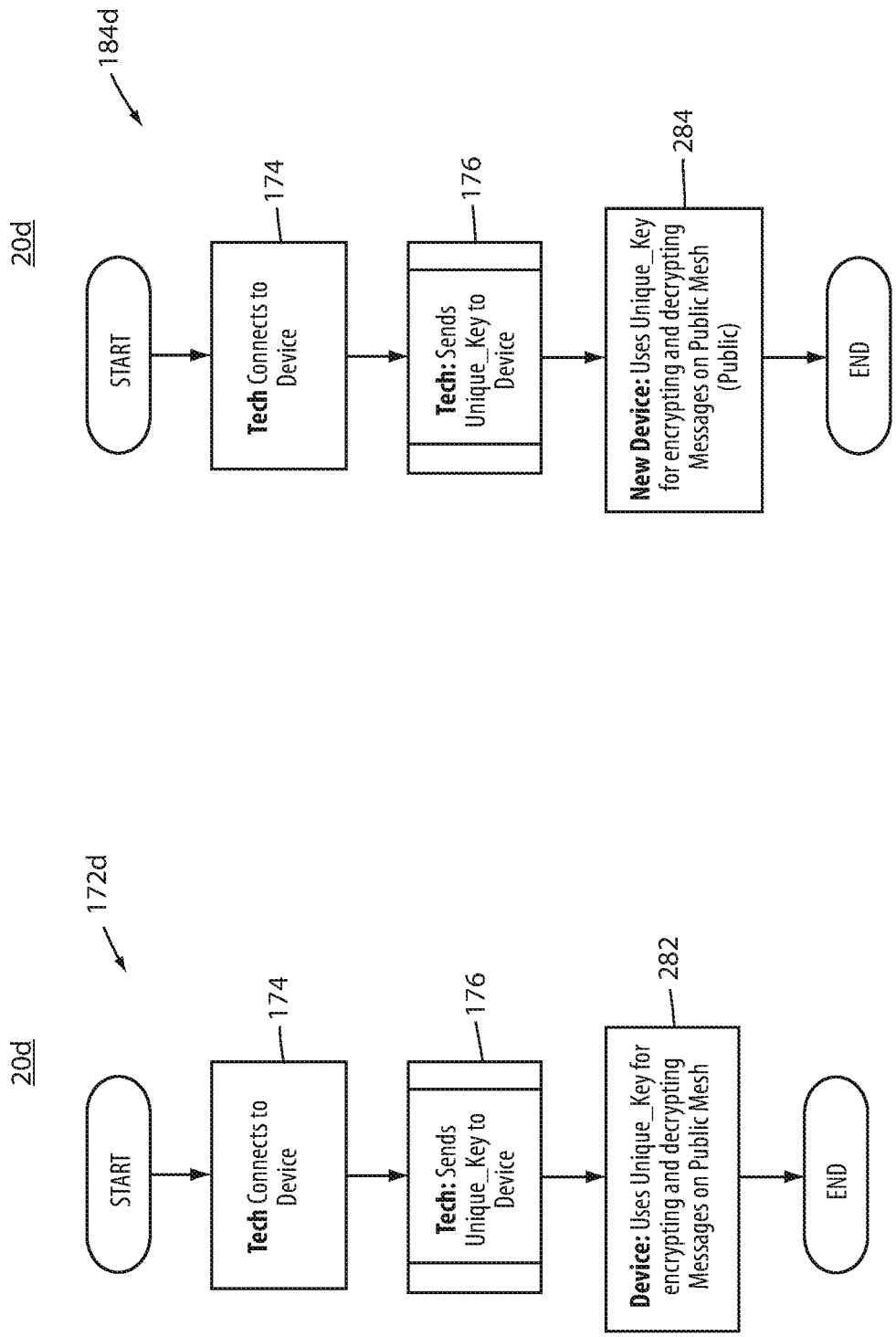
FIG. 14 is a flow diagram of a method for installing a main mesh network key on a first medical device according to a fifth embodiment of the communication system.
FIG. 15 is a flow diagram of a method for subsequently installing the main mesh network key of FIG. 14 on additional medical devices according to the fifth embodiment of the communication system.

FIGS. 14-15 illustrate yet another alternative set of methods for setting up main mesh network 78 on an initial medical device 22 (FIG. 14) and for setting up main mesh network 78 on all of the subsequent medical devices 22 (FIG. 15). These methods are used in communication system 20d. Communication system 20d differs from one or more of the previously described communication systems in one or more respects. First, communication system 20d, like communication system 20c, includes no provisioning mesh network 76, and instead only includes a single mesh network: main mesh network 78. Second, communication system 20d determines which medical devices 22 are authorized or not based upon a technician deciding what devices 22 are authorized and manually activating those devices 22 using a computer. Communication system 20d also differs from communication systems 20, 20a, 20b, and 20c in that it does not transmit any access keys 152 between nodes 170, but instead shares the healthcare facility access key 152 via the manual steps of the technician. These and other differences and similarities are discussed in greater detail below.

Communication system 20d, as with communication systems 20, 20a, 20b, and 20c, utilizes two methods for initializing nodes: a first node initialization method 172d for initializing the first node of main mesh network 78 and a subsequent node initialization method 184d for initializing all of the nodes after the first node of main mesh network 78 has been initialized. First node initialization method 172d is illustrated in FIG. 14 and subsequent node initialization method 184d is illustrated in FIG. 15. Variations from what is shown in these drawings may be implemented.

Method 172d of communication system 20d (FIG. 14) utilizes a number of steps that are common to the previously described first node initialization methods 172, 172a, 172b, etc. Those common steps have been assigned the same reference number. Steps which are different have been assigned a new reference number.

Method 172d of communication system 20d begins at step 174 when a technician connects his or her computer to the first medical device 22 that is to be part of main mesh network 78. After proceeding to connect to this first medical device 22, the technician sends a unique key to the medical device 22 at step 176. Both steps 174 and 176 have been previously described and need not be further described again.

After sending the unique key to the medical device 22 at step 176 (FIG. 14), the medical device 22 proceeds to step 282 where it uses the unique key to encrypt and decrypt messages that are transmitted over the main mesh network. This usage of the unique key, in at least some embodiments, involves utilizing the unique key input algorithm 142 to generate an access key 152, as has been previously described. The access key 152 is then used as an encryption key for encrypting and decrypting messages sent over the main mesh network 78. After completing step 282, the medical device 22 is ready and able to communicate over main mesh network 78 and method 172d terminates.

To add further medical devices 22 to the main mesh network 78 of communication system 20d, subsequent node initialization method 184d is used (FIG. 15). Subsequent node initialization method 184d begins at step 176 with a technician connecting to the medical device to be added to main mesh network 78 and proceeds to step 178 where a technician transfer the unique key to the medical device. Both steps 176 and 178 have been previously described.

After steps 176 and 178 have been completed, method 178d proceeds to step 284 where the medical device 22 to be added to main mesh network 78 begins using the unique key to encrypt and decrypt messages sent over the main mesh network 78. Step 284 may be performed in the same manner as step 282 of method 172d with the sole exception being that step 282 is performed on the first device to be added to main mesh network 78 and step 284 is performed on all of the medical devices 22 that are to be added to the main mesh network 78 after the first one has been added. After completing step 284, the new medical device 22 is ready and able to communicate over main mesh network 78 and method 184 terminates.

Table 1 summarizes several of the characteristics of communication system 20d. As shown in the fifth column (fifth row underneath the heading row), communication system 20d only uses a single mesh network (main mesh network 78). Communication system 20d also does not need access to a server (sixth column). Both the initialization of the first node of main mesh network 78 of communication system 20d and the initialization of all of the subsequent nodes communication system 20d are performed manually, as indicated in the seventh and eighth columns. Due to the use of the unique key, which, as noted previously, can be individually tailored to a particular healthcare facility 80, or a portion of a healthcare facility 80, the encryption used by main mesh network 78 of communication system 20d is unique to that particular healthcare facility 80, thereby preventing someone who gains illicit access to the access key 152 of that healthcare facility 80 from using the same access key 152 to join the main mesh network 78 of a different healthcare facility 80. Finally, the security of communication system 20d is of a medium strength relative to the other communication system embodiments disclosed herein.

Communication system 20e, which is shown in Table 1, but not illustrated with any drawings, provides yet another alternative manner of implementing a communication system according to the present disclosure. Communication system 20e utilizes a single main mesh network 78 and there is no initial or subsequent initialization methods (e.g. 172 or 184) used in order to set up the main mesh network. Instead, each medical device 22 is manufactured with an encryption key and/or encryption programming that is compatible with other medical devices 22 that are intended to join main mesh network 78. After the medical devices 22 are installed within a healthcare facility, they use their factory-installed keys and/or programming to send out the appropriate discovery and beacon messages to automatically set up a main mesh network 78. Any medical device 22 that includes the appropriate encryption and decryption algorithms can join the main mesh network 78, thereby providing a relatively low level of security, as indicated in the last column of Table 1.

Further characteristics of communication system 20e can be seen in Table 1, such as the fact that it uses only a single mesh network 78 (fifth column). It also does not require access to a server (sixth column), and there is no manual work required to initialize either the first medical device 22 (seventh column) or the subsequent medical devices 22 (eighth column). The ninth column indicates that the encryption used by the main mesh network 78 of a particular healthcare facility 80 is the same encryption used by other main mesh networks 78 at other healthcare facilities 80. This is because the encryption and decryption programming of each medical device 22 is installed during manufacture and is the same for all devices, regardless of which customer purchases the medical devices 22 and regardless of their final destination. As a result, the level of security of communication system 20e is low in comparison to the previously described communication systems, as indicated in the last column of Table 1.

Figure 16:
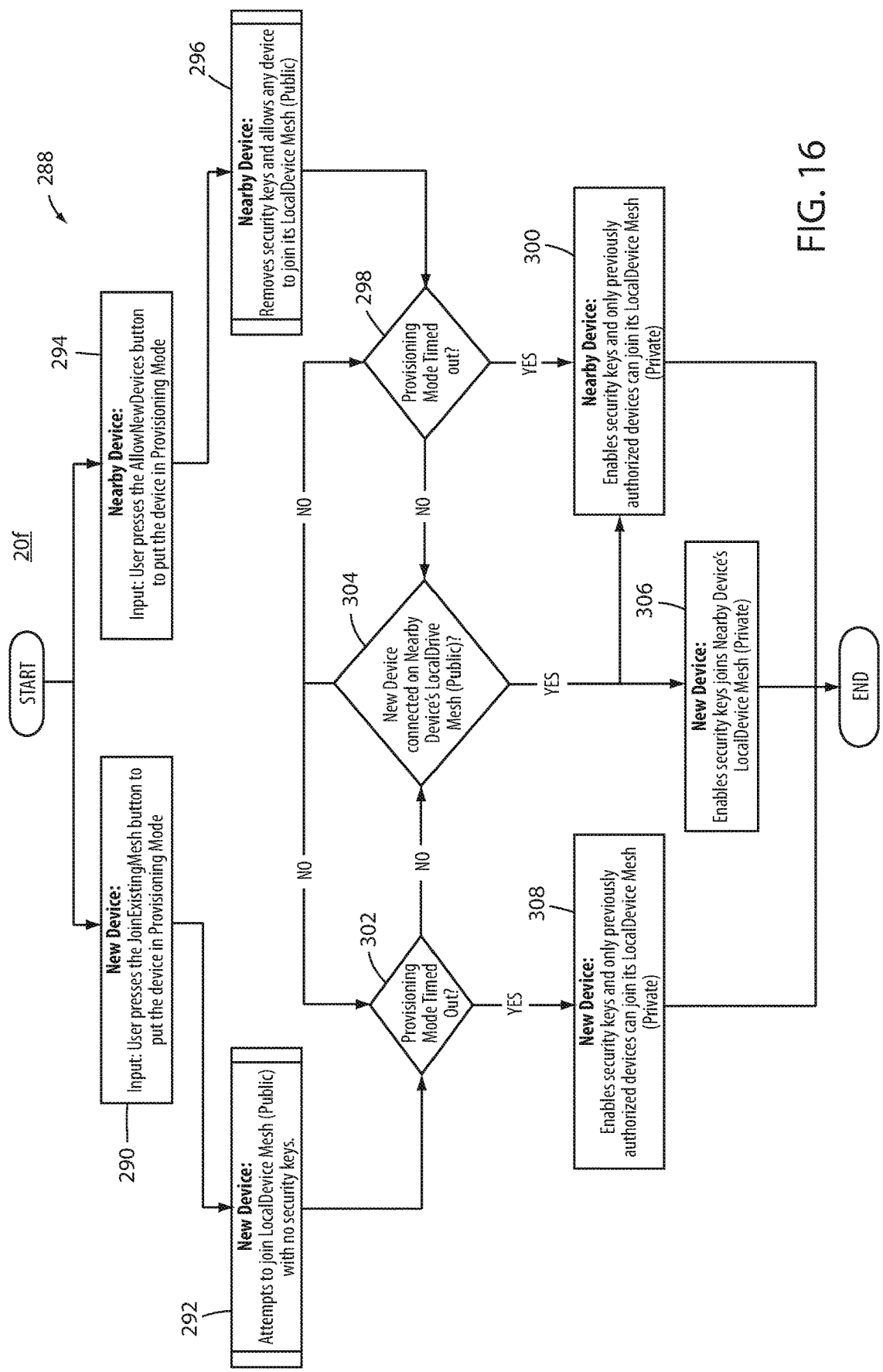
FIG. 16 is a flow diagram of a method for installing a main mesh network key on medical devices according to a sixth embodiment of the communication system.

FIG. 16 illustrates yet another alternative communication system 20f according to the present disclosure. More particularly, FIG. 16 illustrates a method for setting up main mesh network 78 according to communication system 20f. Communication system 20f differs from the previously described embodiments in that there is no separate method used to initialize the first node of main mesh network 78. That is, there is no first initialization method, such as methods 172, 172a, 172b, etc., used with communication system 20f. Instead, all of the medical devices 22 of communication system 20 come with factory installed encryption and decryption algorithms enabling them to be the first node (or subsequent node) of a main mesh network 78. The medical devices 22 of communication system 20f also differ from the medical devices 22 of other communication systems 20 described herein in that they include a join button (or other type of control) and an allow button (or other type of control). These differences are discussed more below.

Communication system 20f does not require a first node 170 (e.g. medical device 22) to be initialized before subsequent nodes 170 are added to a main mesh network 78. Instead, communication system 20 follows an all node initialization method 288 which is illustrated in FIG. 16. All node initialization method 288 requires that at least two medical devices 22 are positioned within communication range of each other. One of the medical devices 22 may already be part of main mesh network 78, or if main mesh network 78 has not yet been set up, neither of the medical devices 22 are part of the main mesh network 78. Regardless of whether or not main mesh network 78 has yet been set up with one of the medical devices 22 or not, once the two medical devices are positioned within range of each other, the "allow" button on the first one of the medical devices 22 is activated (e.g. pushed) and the "join" button on the second one of the medical devices 22 is activated (e.g. pushed). The pushing of each of these buttons starts a limited timed period during which the two medical devices 22 are able to join together and communicate over main mesh network 78. If the two are unable to join together during the limited time period, the main mesh network 78 is not created (or extended) between the two and the method terminates. This is explained in greater detail below with reference to the individual steps of FIG. 16

All node provisioning method 288 (FIG. 16) begins at step 290 when a user manually presses a join button on a medical device 22 that he or she wishes to add to main mesh network 78. For purposes of the following description, and as shown in FIG. 16, this medical device will be referred to herein as the "new device." The controller 104 or 120 of the new device is programmed to attempt to communicate with a "nearby device" at step 292 in response to the pressing of the join button at step 290. The "nearby device" refers to a medical device 22 that is positioned within communication range of the new device and that is already part of main mesh network 78. (In the situation where main mesh network 78 has not yet been set up, the "nearby device" refers to any medical device 22 that is positioned within range of the new device, as will be discussed more below). The controller 104 or 120 is programmed to attempt to communicate with the nearby device only for a first predefined window of time, as discussed more below.

In order for the communication attempt at step 292 to be successful, the user also has to push an allow button at step 294 on the nearby device (FIG. 16) within the first predefined window of time. The pushing of the allow button on the nearby device causes the controller 104 or 120 of that medical device 22 to attempt to communicate with the new device at step 296. Controller 104 or 120 of the nearby device is programmed to carry out this attempt to communicate only for a second predefined window of time. At step 298, the controller 104 or 120 of the nearby device determines if this second predefined time window has expired or not. If it has, the controller 104 or 120 proceeds to step 300 where it takes actions described below. If it has not, the controller 104 or 120 proceeds to step 304, which is also discussed in more detail below.

During the first predefined window, the controller 104 or 120 of the new device is programmed to attempt to communicate with the nearby device using a reduced set of restrictions. In many cases, this involves attempting to communicate using encryption (and/or an encryption key) that all medical devices 22 are preprogrammed with. In some embodiments, this may involve communicating without any encryption at all, although this technique is not preferred. During the second predefined window, the controller 104 or 120 of the nearby device is also programmed to attempt to communicate with the new device using the same reduced set of restrictions, which may involve using factory installed encryption (and/or a factory installed encryption key) or no encryption at all.

At step 302, the controller 104 or 120 of the new device determines whether the first time window has expired or not (FIG. 16). If it has not, controller 104 or 120 of the new device proceeds to step 304. At step 304, both of the controllers 104 or 120 of both the new device and the nearby device check to see if they have successfully established communications with each other using the reduced set of restriction. If they have, method 288 proceeds to step 306 and the new device joins main mesh network 78. This joining of the new device to the main mesh network at step 306 may involve the nearby device sending data to the new device that enables the new device to communicate over main mesh network 78 using a greater set of restrictions. Such data includes, in some embodiments, an access key similar to access key 152, and the new device uses the access key, or data derived from the access key, to encrypt communications over main mesh network. In other embodiments, other data may be sent. After the data is sent, the new device uses the received data to start communicating using the greater set of security restrictions over main mesh network 78.

If the controllers 104 or 120 of both the new device and the nearby device are able successfully establish communications with each other at step 304 (FIG. 16), method 288 also proceeds to step 304 where the nearby device stops communicating using the reduced set of restrictions and instead returns to using the greater set of restrictions required by main mesh network 78. In other words, during the second predefined time window, the nearby device stops using the security restrictions of main mesh network 78 (e.g. encryption) and instead switches to communicating using a lower set of security restrictions. At step 300, the controller 104 or 120 reverts back to communicating over main mesh network 78 with its greater set of security restrictions.

During the first predefined time window, controller 104 or 120 of the new device likewise communicates using the reduced set of restriction requirements (indeed, the new device does not even yet have the data necessary to communicate using the greater set of restriction requirements, in some embodiments). If the new device is unable to establish communications with the nearby device during this first predefined time window, the controller 104 or 120 of the new device proceeds to step 308 of method 288 where it terminates its attempts to communicate with the nearby device. Thus, if the new device and nearby device are unable to establish communications with each other during the period of time when the first and second predefined time windows overlap, both devices will stop attempting such communication at steps 300 and 308 and method 288 will terminate.

It will be understood that, although method 288 has been described above with respect to a "nearby device" that has already joined main mesh network 78, method 288 and FIG. 16 are equally applicable to situations where no main mesh network 78 has yet been set up. In such situations, the user can select any two medical devices 22 that are within communication range of each other and press the join button on one and the allow button on the other. It does not matter which medical device 22 the user selects to correspond to the "new device" or which medical device 22 the user selects to correspond to the "nearby device" of FIG. 16. Whichever medical device 22 the user presses the join button on follows steps 292, 302, 304, and 308. Whichever medical device 22 the user presses the allow button on follows the steps 296, 298, 304, and 300. One of the medical devices 22 may be programmed to generate a random key (comparable to access key 152) and share it with the other after they connect to each other at step 304. The random key is then used for encrypting communications over the newly created main mesh network 78 (and shared with new devices 22 that subsequently join main mesh network 78). The random key thus enables the higher level of security restrictions of the main mesh network 78. Method 288 comes to an end when the two medical devices 22 are either joined together via a newly created main mesh network 78, or the two medical devices 22 were not able to join together via a main mesh network 78.

In some embodiments, the communication that takes place by any medical device 22 during the first or second predefined time windows is carried out over a local device network. That is, each medical device 22 is factory configured to be able to communicate using a local device network. The local device network, in some embodiments, requires some level of encryption and/or other security technology that is installed during the manufacture of the device. After the medical devices 22 have joined together in communication using their local device networks (step 304), the devices exchange a key (which may be random or otherwise comparable to access key 152) that enables the devices to communicate using the higher level of security of main mesh network 78.

A summary of several characteristics of communication system 20f are provided in Table 1. As shown therein, communication system 20f uses only a single mesh network 78 (fifth column), does not require access to a server (sixth column), and manual intervention is required for setting up both the first node of main mesh network 78 (seventh column) and all subsequent nodes of main mesh network (eighth column). The ninth column indicates that the encryption used by the main mesh network 78 of a particular healthcare facility 80 may be the same encryption used by other main mesh networks 78 at other healthcare facilities 80 (although this may be modified to facility specific encryption if a random encryption key is generated by one of the medical devices 22). The level of security of communication system 20f is low in comparison to the previously described communication systems, as indicated in the last column of Table 1.

As was described previously, main mesh network 78 can be used to communicate a wide range of data, regardless of whether it is implemented in communication system 20, 20a, 20b, 20c, 20d, 20e, 20f, or a modification of one or more of these systems. Such data may include performance checks of medical devices 22, usage metrics, health status information of both the device's health and the patient's health, analytics, utilization data, etc. In addition to such data, main mesh network 78 can be utilized to distribute software updates to any of the medical devices 22 that are part of main mesh network 78. Such distribution of software updates over main mesh network 78 can take place using any of the communication systems described herein (e.g. 20, 20a, 20b, etc.).

It will be understood that any of communication system embodiments described herein (e.g. 20, 20a, 20b, 20c, 20d, 20e, 20f, and modifications thereof) may additionally include a unique key refresh algorithm that is programmed into one or more of the medical devices 22. The unique key refresh algorithm may be utilized when the unique key is breached, or when there are other reasons to switch the unique key throughout the main mesh network 78. In some embodiments, the unique key refresh is carried out in the same manner as discussed above for generating the unique key. That is, a technician or other authorized user connects to a selected device, such as performed in step 174, and sends a refreshed unique key to the device, similar to the sending of the original unique key at step 176. The medical device thereafter uses the refreshed unique key to re-create the main mesh network 78 in any of the same manners previously described.

It will further be understood that, as mentioned above, one or more of main and provisioning mesh networks 78 and 76 may be replaced by a non-mesh network in any of the communication system embodiments disclosed herein (e.g. 20, 20a, 20b, 20c, 20d, 20e, 20f, and modifications thereof). Such non-mesh networks may have any of the alternative topologies mentioned previously (e.g. star, ring, daisy, extended star, tree, and hybrid combinations of these topologies.

FIGS. 17-21 illustrate several different methods for distributing a software update for a particular medical device 22 over main mesh network 78. Although all of the methods illustrated in FIGS. 17-21 refer to the software update coming from a server, such as server 94 or 96, it will be understood that these methods are not limited for use with communication system 20 (which is the only communication system described above that relies upon server 94 or 96). In other words, FIGS. 5-16 describe different ways of setting up main mesh network 78, while FIGS. 17-21 describe different ways of using the main mesh network 78 for distributing a software update. Further, although only one of the embodiments of FIGS. 5-16 uses a server (communication system 20 with servers 94 and/or 96), this does not mean that the use of a server in the methods shown in FIGS. 17-21 is limited to use with only this one communication system embodiment (20). Instead, as noted, the methods of FIGS. 17-21 can be used with any of the communication system embodiments discussed herein.

All of the methods of FIGS. 17-21 utilize a server, which may refer to server 94 and/or 96. In all of the methods, the server 94 or 96 receives a software update for one or more of the medical devices 22 and the software update is distributed to the target medical device 22 (i.e. the one whose software is to be updated) using main mesh network 78. The server 94 or 96 may receive the software update in a variety of different manners. For local server 94, the software update may be communicated over the Internet to local server 94, or it may be uploaded to server 94 via a technician that connects his or her computer to server 94 (either directly or via local area network 82). For remote server 96, the software update may be communicated thereto from another location on the Internet, or, in the case where remote server 96 is operated by the entity producing the software update, the software update may be directly loaded to remote server 96 by a representative of that entity. Still other manners of communicating the software update to server 94 or 96 are possible.

All of the methods of FIGS. 17-21 also use what is referred to in the drawings as a "main node." The main node, which has been assigned the reference number 170m in the drawings, is a medical device 22 on the main mesh network 78 that is in direct communication with the server 94 or 96. Such direct communication refers to communication that does not utilize main mesh network 78 or provisioning mesh network 76. In other words, the main node is a medical device 22 that is part of main mesh network 78 and is able to communicate with the server 94 or 96 without using main mesh network 78 (or provisioning mesh network 76 in those embodiments where provisioning mesh network 76 exists). This direct communication of the main node with server 94 or 96 may take place via a communication channel 164 (see FIG. 4), or another type of communication channel.

Figure 19:
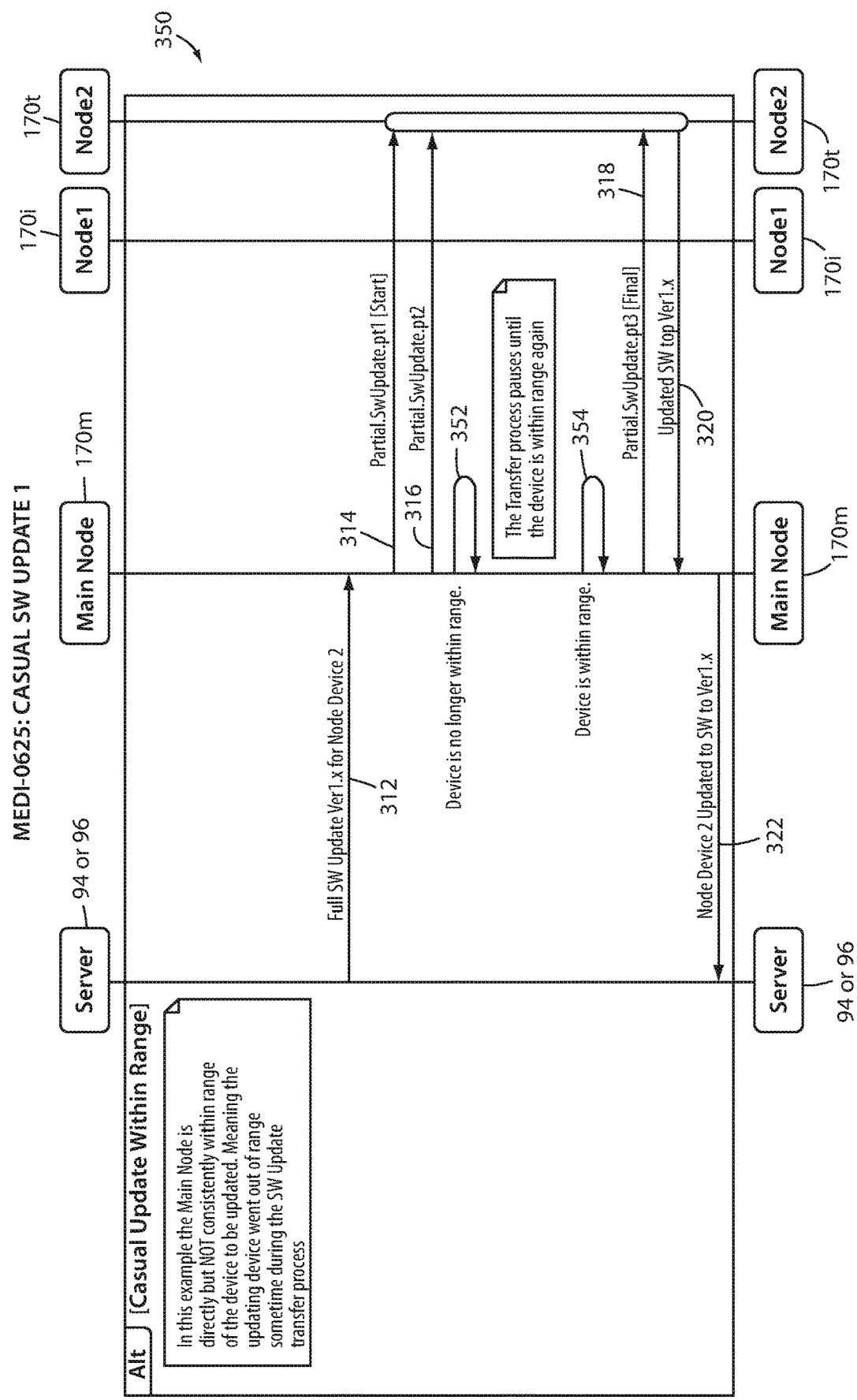
FIG. 19 is a flow diagram of a third method of using one of the communication systems disclosed herein for communicating a software update from a server to a medical device wherein the medical device is intermittently positioned within range of the main node.
Figure 20:
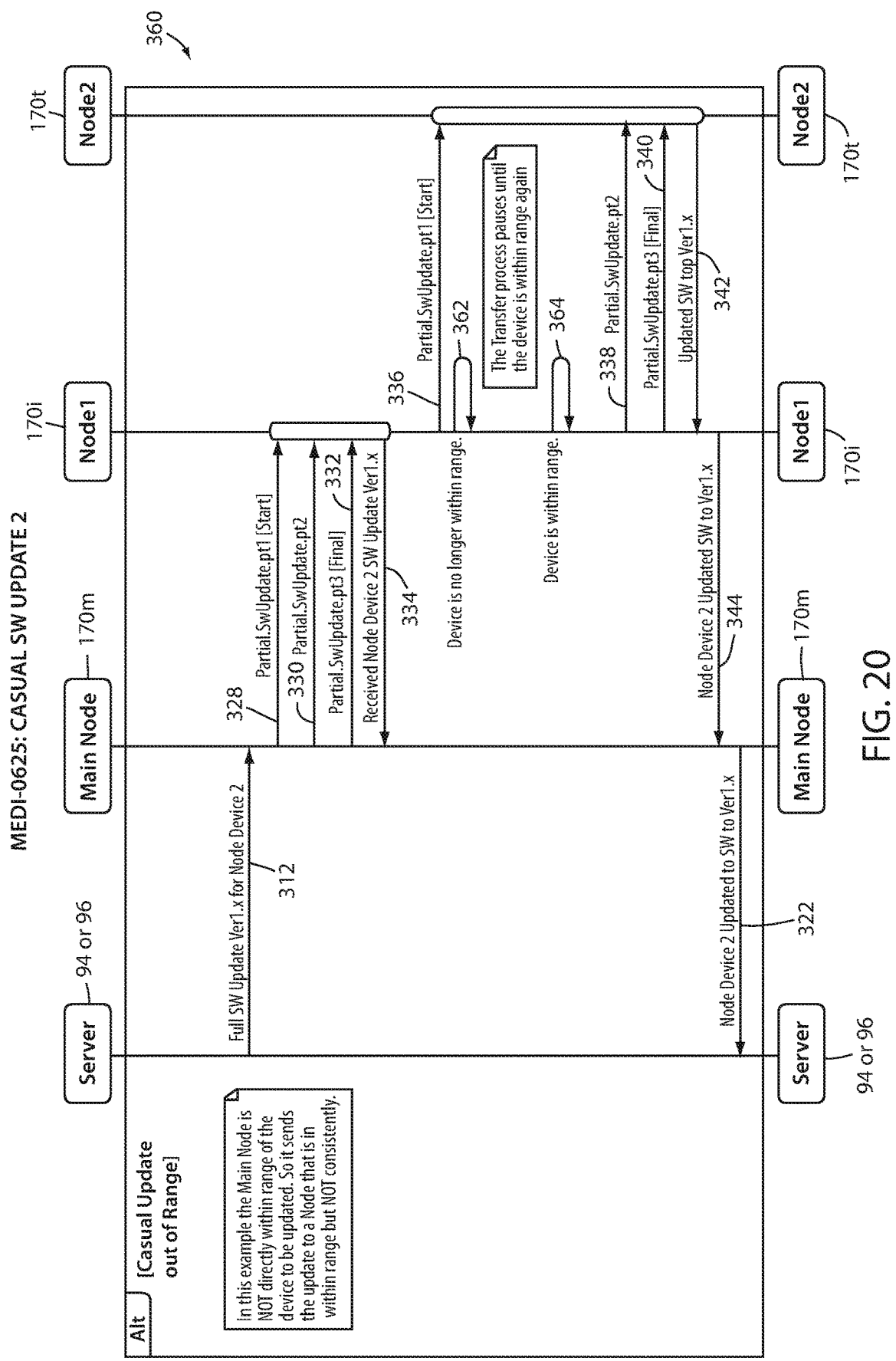
FIG. 20 is a flow diagram of a fourth method of using one of the communication systems disclosed herein for communicating a software update from a server to a medical device wherein the medical device is positioned out of range of the main node, but intermittently within range of another node on a mesh network.
Figure 21:
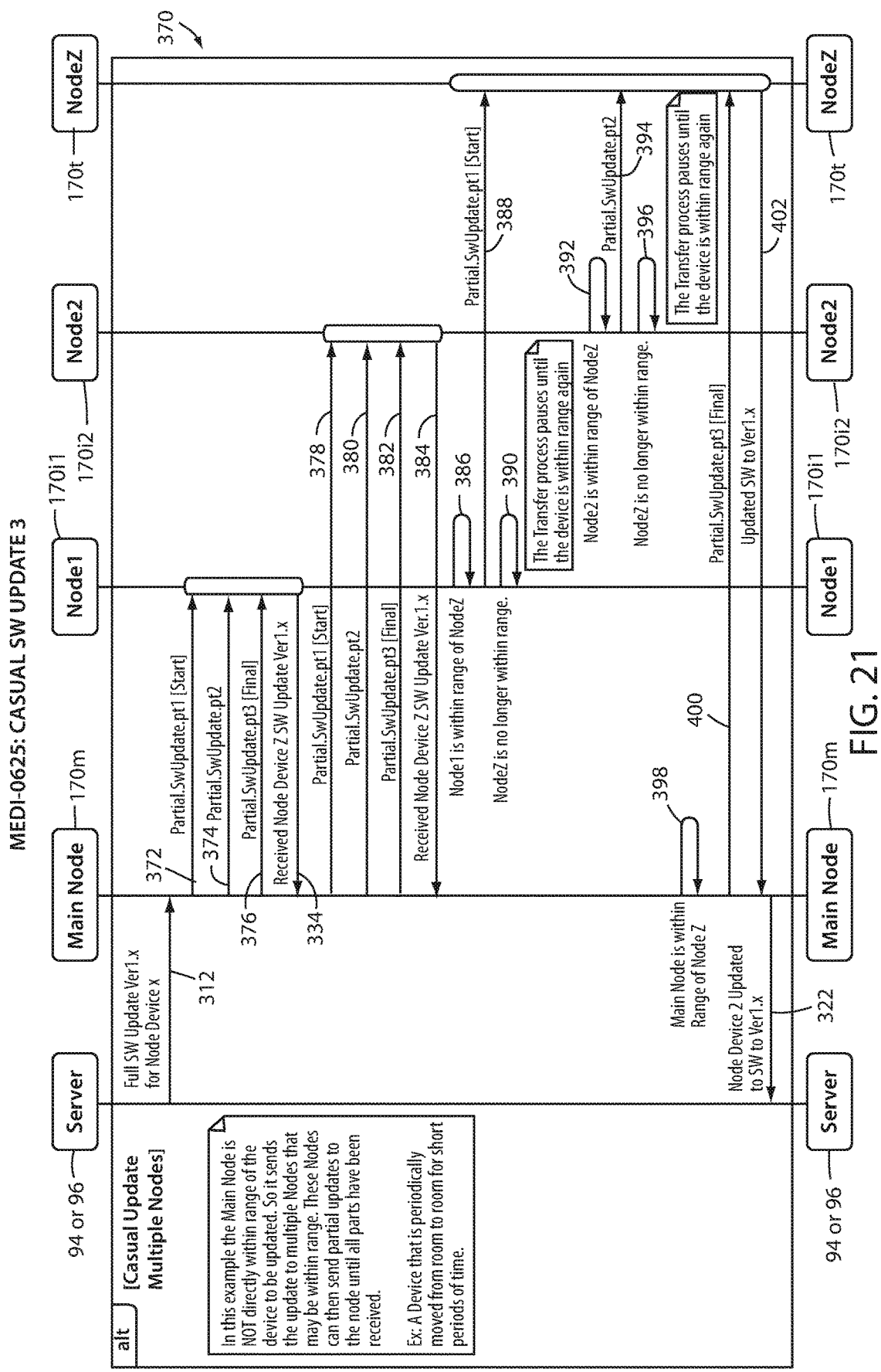
FIG. 21 is a flow diagram of a fifth method of using one of the communication systems disclosed herein for communicating a software update from a server to a medical device wherein the medical device is intermittently positioned within range of the main node and a plurality of different nodes at different times.

In all of the methods of FIGS. 17-21, the medical device 22 that is to receive the software update is referred to as "node 2" in the drawings (or "node Z" in FIG. 21). This medical device 22 has been assigned the reference number 170t in the drawings. The medical device 22 that is referred to as "node 1" in the drawings is a medical device 22 that is part of main mesh network 78 and in communication range with both the main node and node 2. As will be discussed, it serves as an intermediary device for relaying the software update to the target node (node 2) in some embodiments. Node 1 has been assigned the reference number 170i in the drawings.

Figure 17:
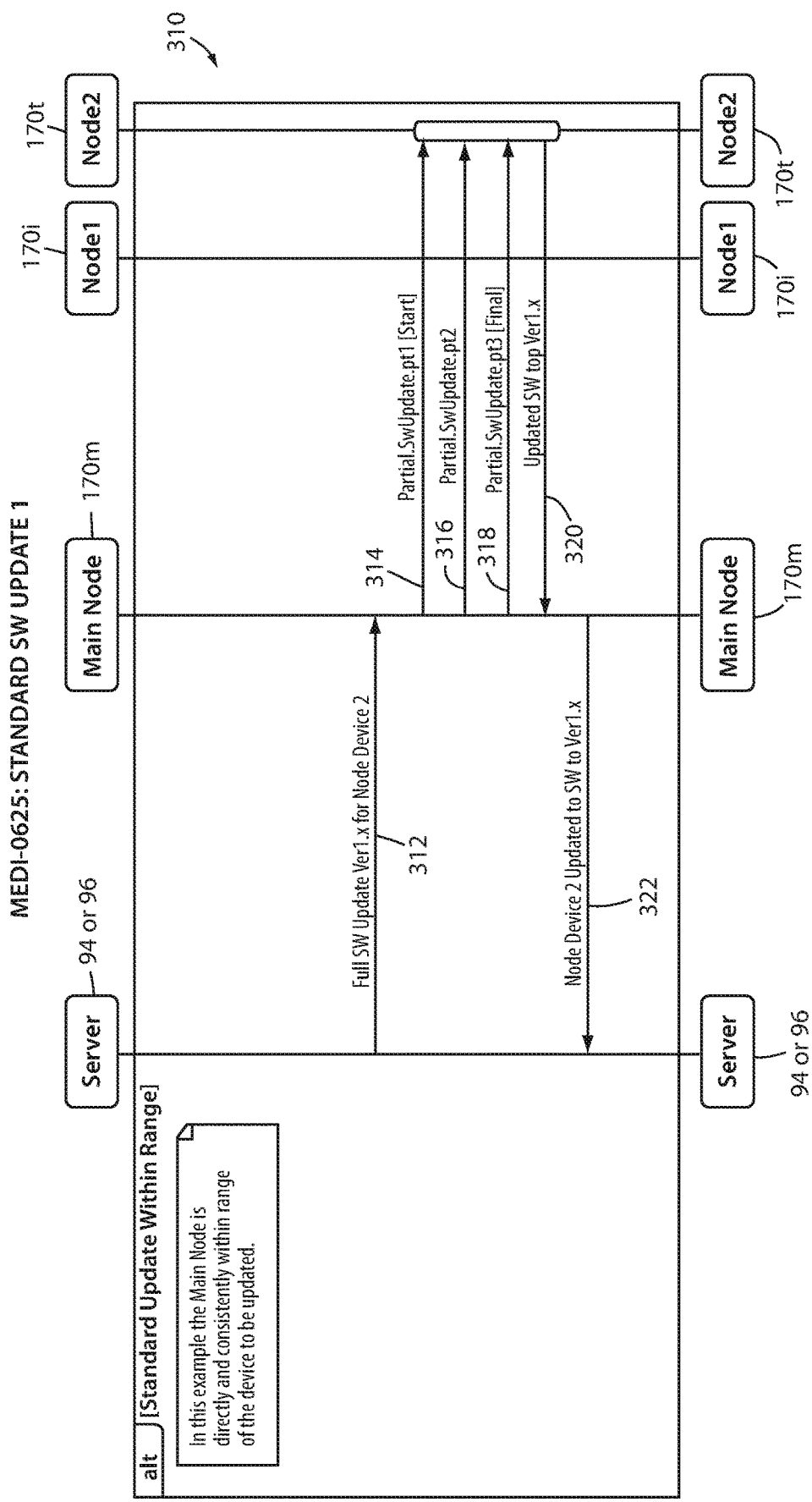
FIG. 17 is a flow diagram of a first method of using one of the communication systems disclosed herein for communicating a software update from a server to a medical device wherein the medical device is always positioned directly within range of a main node.

FIG. 17 illustrates a standard software update method 310. Standard software update method 310 is used when the target node 170t (node 2) is in communication range of the main node 170m such that the software update does not need to pass through any intermediary medical devices 22 (e.g. node 170i, a.k.a. node 1) that are positioned between the target node and the main node. Method 310 begins at step 312 when the server transfers the software update to the main node 170m. This happens over communication channel 164 (not shown in FIG. 17), or another communication channel that does not utilize main or provisioning mesh networks 76 or 78. At step 314, the main node 170m transfers via main mesh network 78 all or a portion of the software update directly to the target node 170t. In the example shown in FIG. 17, only a first portion of the software update is transferred at step 314. The remaining portions of the software update are transferred to the target node at steps 316 and 316. It will be understood, however, that depending upon the size of the software update, it may be possible to transfer the entire software update from main node 170m to target node 170t in a single software update message 146. It will also be understood that, depending upon the size of the software update, more than three messages 146 from main node 170m to target node 170t may be needed to complete the transfer of the software update to target node 170t.

After receiving the software updates at steps 314, 316, 318, etc. the target node responds with an acknowledgement message at step 320. The acknowledgement message indicates that the target node 170t successfully received the entire software update. The acknowledgement message may also indicate that the software update has been successfully installed, although in some embodiments the target node 170t is programmed to send a separate message after it is has successfully installed its update. After sending the acknowledgement message back to main node 170m at step 320, the main node 170m relays the acknowledgement message back to server 94 or server 96 at step 322. In this manner, server 94 or 96 receives confirmation that the software update has been successfully communicated to the proper medical device 22.

In all of the messages described with respect to method 310 of FIG. 17, the identity of the target node 170*t* may be included. Thus, for example, when main node 170*m* receives the software update, the message from server 94 or 96 may include an identification of which medical device 22 is the target node 170*t*. This identification may take on several forms, such as, but not limited to, a serial number, a MAC address, a device ID 136, and/or some other form. Further, when the target node 170*t* responds with its acknowledgement message indicating that it has successfully received the entire software update, it includes in the message an identifier of itself. The server 94, 96 and/or main node 170*m* uses this identification to maintain a list of which medical devices 22 have which software versions stored thereon, in at least some embodiments. Still further, the software update messages 146 themselves include the device ID of the target node 170*t*, as well as other information previously described and indicated in FIG. 3.

Figure 18:
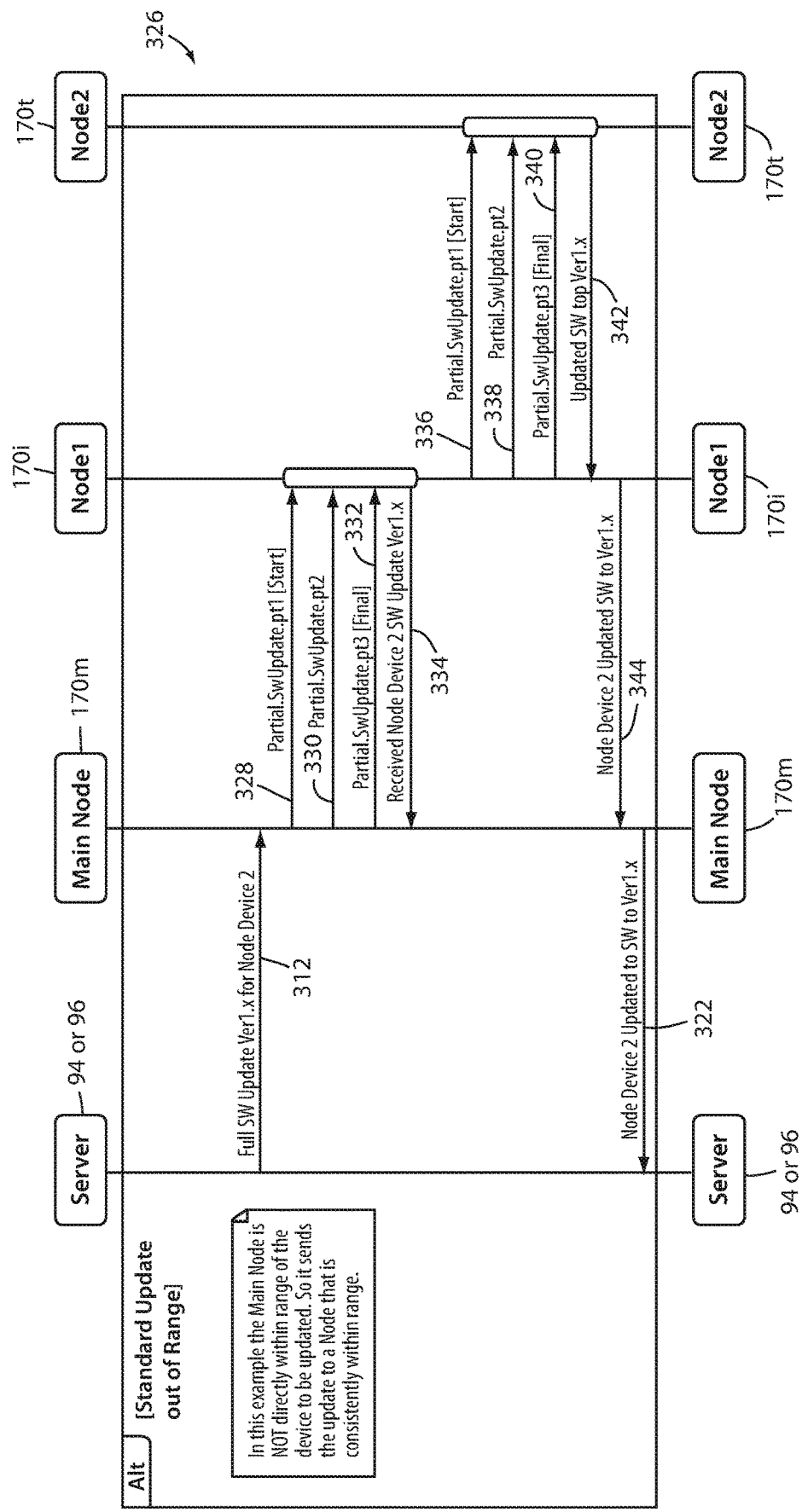
FIG. 18 is a flow diagram of a second method of using one of the communication systems disclosed herein for communicating a software update from a server to a medical device wherein the medical device is positioned out of range of the main node, but within range of another node on a mesh network.

FIG. 18 illustrates a first alternative software update method 326. Main node 170*m* uses method 326 when it is not within communication range of target node 170*t* and therefore not able to communicate the software update directly to target node 170*t*. Method 326 includes a number of steps that are the same as steps found in method 310 and previously described. Such common steps are provided with the same reference number.

Method 326 starts with main node 170*m* receiving the software update from server 94 or 96 at step 312. After receiving the software update from server 94 or 96, main node 170*m* transfers the software update to an intermediate node 170*i* at step 328. If the software update is large, this may involve transmitting several software update messages 146 to intermediate node 170*i*, as indicated by steps 330 and 332 in FIG. 18. Still more messages 146 may, of course, be required for this transfer.

After receiving the software update, intermediate node 170*i* sends an acknowledgement message back to main node 170*m* at step 334. Main node 170*m*, in at least some embodiments, keeps track of which nodes have received the software update, at least until the software update has been successfully received by the target node 170*t*. After receiving the software update, the intermediate node 170*i* transfers the software update to the target node 170*t* in one or more software update messages 146, as indicated by steps 336, 338, 340, etc. In some situations, the intermediate node 170*i* may have to relay the software update to one or more other intermediate nodes before the software update is able to be received by the target node 170*t*. This will depend upon the physical location of target node 170*t* relative to intermediate node 170*i* and the communication ranges of the nodes 170.

After successfully receiving the software update, the target node 170*t* sends an acknowledgement message at step 342 to the intermediate node 170*i*. The intermediate node 170*i* relays this message back to main node 170*m* at step 344, either directly or through other intermediate nodes, depending upon the current position of intermediate node 170*i* relative to main node 170*m* and its communication range. The main node 170*m*, after receiving the acknowledgment message, then forwards the acknowledgement message back to server 94 or 96 at step 322. The server uses the acknowledgement to update its master list of which medical devices 22 within healthcare facility 80 have which software versions.

FIG. 19 illustrates a second alternative software update method 350. Main node 170*m* uses method 350 when it is initially within communication range of target node 170*t* but then goes out of communication range for an interim time period during the update process. The movement of main node 170*m* out of range of target node 170*t* may be due to movement of main node 170*m*, movement of target node 170*t*, or a combination of both. Method 350 begins at step 312 where server 94 or 96 delivers the software update to main node 170*m*. Main node 170*m* starts forwarding the software update to target node 170*t* by sending a software update message 146 at step 314. Additional software update messages 146 may be sent at steps 316, 318, etc. if time permits before target node 170*t* and main node 170*m* move out of communication range with each other. In the example shown in FIG. 19, the main node 170*m* is able to deliver two software update messages 146 at steps 314 and 316 before communication is lost between main node 170*m* and target node 170*t* at moment 352. It will be understood that this is merely an arbitrary selection of software update messages 146 and that the interruption in the communication between main node 170*m* and target node 170*t* may occur at a different time.

When the direction communication between main node 170*m* and the target node 170*t* is no longer possible (moment 352), software update method 350 pauses. In some embodiments, the pause is limited by a threshold amount of time. That is, in some embodiments, if main node 170*m* is not able to re-establish direct communication with target node 170*t* within a set period of time, main node 170*m* switches to another method of updating the software on target node 170*t* (e.g. one of the other methods described herein). In the example shown in FIG. 19, the main node 170*m* and target node 170*t* re-establish direct communication at moment 354. Thereafter, main node 170*m* resumes sending one or more software update messages 146 to target node 170*t* via main mesh network 78. This is illustrated at step 318. At step 320, the target node 170*t* sends an acknowledgment message back to main node 170*m* and main node 170*m* forwards the acknowledgement to the server 94 or 96 at step 322, as has been previously described.

FIG. 20 illustrates a third alternative software update method 360. Method 360 is used when main node 170*m* is not within range of target node 170*t* and one or more intermediate nodes 170*i* go into and out of communication range of target node 170*t* during the software update process. Method 360 begins at step 312 where server 94 or 96 delivers the software update to main node 170*m*. After step 312, main node 170*m* transfers the software to intermediate node 170*i* in one or more software messages 146. This is shown in FIG. 20 taking place via steps 328, 330, and 332, although it will be understood that fewer or greater numbers of software update messages 146 may be needed, depending upon the size of the software update. After the software update is successfully transfer to intermediate node 170*i*, intermediate node 170*i* sends an acknowledgment message back to main node 170*m* at step 334. As noted previously, main node 170*m* uses the message sent at step 334 to keep track of where the software update is in the main mesh network 78.

After intermediate node 170*i* receives the software update, it proceeds to start forwarding the software update to target node 170*t* at step 336. In the example shown in FIG. 20, the forwarding of the software update from intermediate node 170*i* to target node 170*t* is interrupted after a single messages 146 at moment 362. It will be understood that this is an arbitrary example and that the interruption at moment 362 may occur at any time, including before intermediate node 170*i* has a chance to send a single update message 146 to target node 170*t*. At moment 364, the target node 170*t* comes back into communication range of intermediate node 170*i* and node 170*i* completes the software update by sending a series of software update messages 146 to the target node 170*t* via main mesh network 78. This is illustrated by steps 338 and 340. It will be understood that a different number of messages 146 may be used.

After receiving the full set of software update messages at step 340, target node 170*t* sends an acknowledgement message back to intermediate node 170*i* at step 342. Intermediate node 170*i* forwards the acknowledgement messages back to main node 170*m* at step 344, and the main node 170*m* forwards it to server 94 or 96 at step 322. Server 94 or 96 is thereby apprised of the successful communication of the software update to target node 170*t*.

FIG. 21 illustrates a fourth alternative software update method 370. Method 370 is used when main node 170*m* is not initially within range of target node 170*t* and a plurality of intermediate nodes (e.g. 170*i*1 and 170*i*2) are utilized to ensure the communication of the software update to target node 170*t* via main mesh network 78. Method 370 begins at step 312 where server 94 or 96 delivers the software update to main node 170*m*. After step 312, main node 170*m* transfers the software to a first intermediate node 170*i*1 in one or more software messages 146. In the example of FIG. 21, this takes place via three software update messages 146 that are sent at steps 372, 374, and 376. After the first intermediate node 170*i*1 receives the software update, it sends an acknowledgement message back to main node 170*m* at step 334.

After directly forwarding the software update to first intermediate node 170*i*1, main mode 170*m* also forwards the software update directly to a second intermediate node 170*i*2. In some embodiments, the forwarding of the software update to second intermediate node 170*i*2 is delayed until after a predetermined time has elapsed since forwarding the software update to first intermediate node 170*i*1. During this time period, if main mode 170*m* receives a message (e.g. step 322 or 344) indicating that the software update was able to be successfully transferred to target node 170*t* after forwarding it to only first intermediate node 170*i*1, method 370 terminates and the target node 170*t* updates its software. In other embodiments, the forwarding of the software update to the second intermediate node 170*i*2 occurs without waiting for such a predetermined time period to elapse.

Regardless of the delay or lack of delay in commencing with the forwarding of the software update from main node 170*m* to the second intermediate node 170*i*2, the actual forwarding to the second intermediate node 170*i*2 is shown to take place in FIG. 21 in steps 378, 380, and 382. After the second intermediate node 170*i*2 receives the software update, it sends an acknowledgement message back to main node 170*m* at step 384. At moment 386, the first intermediate node 170*i* comes into direct communication range of the target node 170*t* via main mesh network 78. In some embodiments, moment 386 may occur before the software update is sent to second intermediate node 170*i*2 and/or before the software is sent to first intermediate node 170*i*1. In either case, first intermediate node 170*i*1 begins relaying the software update to target node 170*t* at step 388. This relaying of the software update to target node 170*t* is shown to be interrupted at moment 390 after only a single software update message was sent at step 388. First intermediate node 170*i*1 therefore pauses its sending of software updates to target node 170*t*.

At moment 392 (FIG. 21), the second intermediate node 170*i*2 comes into communication range of the target node 170*t*. Second intermediate node 170*i*2 commences sending the software update to target node 170*t* at step 394. Prior to sending the software update at step 394, second intermediate node 170*i*2 may transmit one or more messages to target node 170*t* in order to find out how much, if any, of the software update target node 170*t* has already received from other sources (e.g. first intermediate node 170*i*1). In this manner, second intermediate node 170*i*2 avoids sending pieces of the software update that target node 170*t* has already received. In alternative embodiments, second intermediate node 170*i*2 relays the entire set of software updates to target node 170*t* regardless of which pieces the target node 170*t* has already received, and lets target node 170*t* discard pieces that were received in duplicate (or triplicate, etc.).

At moment 396, the second intermediate node 170*i*2 moves out of direct communication range of target node 170*t*. This pauses the sending of further software update messages 146 from second intermediate node 170*i*2 to target node 170*t*. At moment 398, however, the main node 170*m* comes into direct communication range of target node 170*t*. Main node 170*m* therefore sends software update messages 146 to the target node 170*t* at step 400. As with the software update messages sent by second intermediate node 170*i*2 at step 394, the sending of software update messages 146 at step 400 may involve one or more pre-communication messages between main node 170*m* and target node 170*t* in order to determine what pieces of the software update the target node has already received. Alternatively, the main node 170*m* may send all of the pieces of the software update it has not previously sent to target node 170*t* (if any) at step 400.

Regardless of whether target node 170*t* has received any duplicate copies of the software update, at step 402 it sends an acknowledgement message back to whichever node 170 sent it the last portion of the software update. In the example of FIG. 21, this is main node 170*m*. Main node 170*m* relays the acknowledgment message to server 94 or 96 at step 322 and method 370 terminates.

It will be appreciated that any of the software update methods described above that utilize one or more intermediate nodes 170*i* may be modified to include additional intermediate nodes 170*i*, depending upon the physical distance between main node 170*m* and the target node 170*t*, as well as the communication range of each of the nodes of main mesh network 78. It will also be appreciated that the intermediate nodes 170*i* may be programmed to delete software messages 146 that they receive but are unable to forward to another node 170 on the main mesh network 78 within a predetermined time period. The predetermined time period may corresponds to the age 158 of the message 146, as discussed previously with respect to FIG. 3. The deletion of software update messages after a certain amount of time enables the intermediate nodes 170*i* to clear out their memory buffers.

It will also be appreciated that any of the steps of the software update methods described above (310, 326, 350, 360, and 370) may be modified to include one or more of the steps of one or more of the other methods. In other words, methods 310, 326, 350, 360, and 370 may be combined, either wholly or in portions, with each other. For example, in some modified embodiments, main node 170*m* may start a particular method and switch to another method after failing to update the target node 170*t* within a predetermined time period. The predetermined time period may be set large enough to allow a reasonable opportunity for the software update to occur, but not so large as to unduly delay the updating of the software on the target node 170t. When the communication system uses more than one of the software update methods described above, the switching between methods (or the starting of one or more additional methods) may be based upon one or more of the nodes 170 moving into, or out of, communication with other nodes 170 of the main mesh network 78, the expiration of one or more predetermined time periods, a combination of the two, and/or other factors.

Finally, it will be appreciated that the selection of a particular method to use for a given software update may be carried out by main mode 170m, or it may be carried out via individual programming of the nodes 170, or a combination of both. Thus, for example, in some embodiments, each node 170 is programmed to forward any software update message 146 to any other node of main mesh network 78 that is within its communication range and that has not already received the software update. This is then repeated by each node 170 until the target node receives the software update. Further, in some embodiments, the target node 170t's acknowledgment message may be distributed throughout the nodes 170 of main mesh network 78 so that the nodes 170 know not only when to stop forwarding the software updates, but also when to delete any portions of that software update that they have stored in memory. Still other variations may be implemented.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:
a base;
a plurality of wheels coupled to the base;
an adjustable height litter supported on the base,
a patient support surface supported on the adjustable height litter and adapted to support a patient thereon;
a plurality of siderails coupled to the adjustable height litter and adapted to move between raised and lowered positions;
a memory having a first key stored therein;
a transceiver adapted to wirelessly communicate with a first medical device over a first mesh network using the first key; and
a controller adapted to transmit a request message over the first mesh network to the first medical device via the transceiver, the request message including an identifier identifying the patient support apparatus and a request to join a second mesh network different from the first mesh network, the controller further adapted to receive a second key input over the first mesh network, to use the second key input to generate a second key, to use the second key to communicate over the second mesh network, to receive a software update over the second mesh network, the software update being received from a second medical device and intended for updating software on-board a third medical device, and to forward the software update to the third medical device over the second mesh network;
wherein the first medical device is a second patient support apparatus.

2. The patient support apparatus of claim 1 wherein the controller is further adapted to receive the software update over the second mesh network but not the first mesh network.

3. The patient support apparatus of claim 1 wherein the transceiver is adapted to communicate over the first and second mesh networks using a common communication frequency and a common communication protocol, and wherein the controller is adapted to encrypt messages transmitted over the first mesh network using the first key and to encrypt messages transmitted over the second mesh network using the second key.

4. The patient support apparatus of claim 1 wherein the controller is adapted to receive a second request message over the first mesh network from a fourth medical device, the second request message including a second identifier identifying the fourth medical device and a second request by the fourth medical device to join the second mesh network, and the controller is further adapted to forward the second identifier and the second request using the second mesh network to a fifth medical device via the transceiver.

5. The patient support apparatus of claim 1 wherein the controller is further adapted to receive a validation message from a fourth medical device over the second mesh network, the validation message including data indicating that a fifth medical device is a valid device for joining the second mesh network, the controller further adapted to forward to the fifth medical device the second key input in response to the validation message.

6. The patient support apparatus of claim 1 wherein the controller is further adapted to communicate with a remote server via an Internet connection and to receive a validation message from the remote server via the Internet connection, the validation message including data indicating that a fourth medical device is a valid device for joining the second mesh network, and the controller being further adapted to forward to the fourth medical device the second key input in response to the validation message.

7. A patient support apparatus comprising:
a base;
a plurality of wheels coupled to the base;
an adjustable height litter supported on the base,
a patient support surface supported on the adjustable height litter and adapted to support a patient thereon;
a plurality of siderails coupled to the adjustable height litter and adapted to move between raised and lowered positions;
a memory having a first key, a second key, and a second key input stored therein;
a first transceiver adapted to wirelessly communicate with a set of medical devices over a first mesh network using the first key and to wirelessly communicate with a subset of the medical devices over a second mesh network using the second key; and
a controller adapted to receive a validation message via the first transceiver indicating an individual one of the medical devices in the set of medical devices has been validated for inclusion in the subset of the medical devices, the controller further adapted to transmit the second key input to the individual one of the medical devices in response to the validation message in order to enable the individual one of the medical devices to generate the second key from the second key input and to use the second key to communicate over the second mesh network, the controller further adapted to receive a software update over the second mesh network, the software update being received from a first medical device in the subset of medical devices and intended for updating software on-board the individual one of the medical devices, and to forward the software update to the individual one of the medical devices over the second mesh network.

8. The patient support apparatus of claim 7 wherein the controller receives the validation message over the second mesh network from the first medical device in the subset of the medical devices.

9. The patient support apparatus of claim 7 further comprising a second transceiver adapted to communicate directly with an access point of a healthcare computer network, and wherein the controller receives the validation message from a server in communication with the access point, the server being located outside of a healthcare facility in which the patient support apparatus and the set of medical devices are located.

10. The patient support apparatus of claim 7 wherein the controller is adapted to receive the software update via the first transceiver and the second mesh network but not via the first mesh network, and the controller is further adapted to transmit the software update via the first transceiver and the second mesh network but not via the first mesh network.

11. The patient support apparatus of claim 7 wherein the first mesh network and the second mesh network both use Bluetooth communications but do not require the patient support apparatus and medical devices to be paired with each other before communicating with each other.

12. The patient support apparatus of claim 7 wherein the controller is further adapted to encrypt messages transmitted over the first mesh network using the first key and to encrypt messages transmitted over the second mesh network using the second key.

13. The patient support apparatus of claim 7 wherein the controller is adapted to receive a request message from the individual one of the medical devices prior to receiving the validation message, the request message including a request for the individual one of the medical devices to be validated for inclusion in the subset of the medical devices, and the controller is further adapted to forward the request message to a validation node of the second mesh network.

14. A patient support apparatus comprising:
a base;
a plurality of wheels coupled to the base;
an adjustable height litter supported on the base,
a patient support surface supported on the adjustable height litter and adapted to support a patient thereon;
a plurality of siderails coupled to the adjustable height litter and adapted to move between raised and lowered positions;
a memory having a first key stored therein;
a first transceiver adapted to wirelessly communicate with a set of medical devices over a first mesh network using the first key; and
a controller adapted to send a request message over the first mesh network, the request message including a request for a second key input enabling the patient support apparatus to generate a second key for communicating over a second mesh network using the first transceiver, and wherein the controller is further adapted to receive a validation message with the second key input if a validation node on the second mesh network approves of the request, the controller further adapted to receive a software update over the second mesh network, the software update being received from a first medical device of the set of medical devices and intended for updating software on-board a second medical device of the set of medical devices, and to forward the software update to the second medical device over the second mesh network.

15. The patient support apparatus of claim 14 wherein the controller is further adapted to use the second key to receive a second software update for the patient support apparatus over the second mesh network, and wherein the controller is adapted to implement the second software update on the patient support apparatus.

16. The patient support apparatus of claim 14 further comprising a second transceiver adapted to communicate directly with a hospital computer network having a plurality of nodes and access points, wherein the second mesh network does not include any of the nodes or access points of the hospital computer network, and the software update is able to be delivered from the patient support apparatus to the second medical device without using the hospital computer network.

17. The patient support apparatus of claim 14 wherein the validation node is in communication with a remote server via the Internet.

* * * * *